(12) United States Patent
Conn et al.

(10) Patent No.: US 9,676,782 B2
(45) Date of Patent: Jun. 13, 2017

(54) SUBSTITUTED PYRAZOLO[1,5-A]PYRAZINES AS NEGATIVE ALLOSTERIC MODULATORS OF METABOTROPIC GLUTAMATE RECEPTOR 3

(71) Applicant: Vanderbilt University, Nashville, TN (US)

(72) Inventors: P. Jeffrey Conn, Nashville, TN (US); Craig W. Lindsley, Brentwood, TN (US); Kyle A. Emmitte, Spring Hill, TN (US); Julie L. Engers, Nashville, TN (US); Leah C. Konkol, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 75 days.

(21) Appl. No.: 14/738,222

(22) Filed: Jun. 12, 2015

(65) Prior Publication Data

US 2015/0361081 A1    Dec. 17, 2015

Related U.S. Application Data

(60) Provisional application No. 62/012,016, filed on Jun. 13, 2014.

(51) Int. Cl.
*A61K 31/4985* (2006.01)
*C07D 487/04* (2006.01)

(52) U.S. Cl.
CPC ................. *C07D 487/04* (2013.01)

(58) Field of Classification Search
CPC .......................... A61K 31/4985; C07D 487/04
USPC .......................................... 514/249; 544/350
See application file for complete search history.

(56) References Cited

U.S. PATENT DOCUMENTS 8,592,422 B2   11/2013   Conn et al.
2014/0057870 A1   2/2014   Conn et al.

FOREIGN PATENT DOCUMENTS

WO   2012/083224   6/2012

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

*Primary Examiner* — Douglas M Willis
(74) *Attorney, Agent, or Firm* — Michael Best & Friedrich LLP

(57) ABSTRACT

Described are negative allosteric modulators of metabotropic glutamate receptor 3 ($mGlu_3$), pharmaceutical compositions including the compounds, and methods of using the compounds and compositions for treating depression, cognitive disorders, schizophrenia, Alzheimer's disease, or cancer in a subject. Exemplary negative allosteric modulators of metabotropic glutamate receptor 3 include pyrazolo[1,5-α]pyrazine compounds, such as those of the following formula:

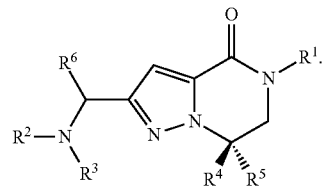

20 Claims, No Drawings

SUBSTITUTED PYRAZOLO[1,5-A]PYRAZINES AS NEGATIVE ALLOSTERIC MODULATORS OF METABOTROPIC GLUTAMATE RECEPTOR 3

CROSS-REFERENCE TO RELATED APPLICATION

This application is a non-provisional of and claims priority to U.S. Provisional Application No. 62/012,016, filed Jun. 13, 2014, the entire contents of which is incorporated herein by reference.

STATEMENT OF GOVERNMENT INTEREST

This invention was made with government support under Grant number 1 R01 MH99269-01 awarded by the National Institute of Mental Health (NIMH). The government has certain rights in the invention.

TECHNICAL FIELD

The present disclosure relates to compounds, compositions, and methods for treating metabotropic glutamate receptor 3 related diseases and/or disorders, such as depression, cognitive disorders, schizophrenia, Alzheimer's disease, and cancer.

BACKGROUND

Metabotropic glutamate receptors (mGlus), a class of G-protein coupled receptor (GPCR) family C, have recently emerged as targets of potential therapeutic value. They bind glutamate, an amino acid that is the most prominent excitatory neurotransmitter in the human central nervous system (CNS). mGlus are known to activate biochemical cascades, leading to the modification of other proteins. For example, this can lead to changes in a synapse's excitability by presynaptic inhibition of neurotransmission, or modulation and even induction of postsynaptic responses.

Metabotropic glutamate receptor 3 (mGlu3) is one of eight mGlus that have been identified, and, along with mGlu2, is classified as a group II mGlu. Group II mGlus play an important role is synaptic plasticity, which directly effects cognitive function (including learning and memory), among other things. The effects of group II mGlus occur primarily presynaptically via their inhibition of glutamate release. These effects can also be due to the inhibition of non-vesicular glutamate release from glia. However, group II receptors are known to also reduce the activity of postsynaptic potentials, both excitatory and inhibitory, in the cortex. It is also suggested that mGlu3 is involved with regulating non-synaptic glutamate since it is localized away from active synaptic zones.

Dysfunction of mGlu3 has been implicated in many diseases and/or disorders. Hence, targeting mGlu3 activity has been the subject of much investigation. Several reports have highlighted its link to a variety of diseases, such as cognitive disorders, schizophrenia, depression, Alzheimer's disease, and cancer. Accordingly, there exists a need for modulators of mGlu3.

SUMMARY OF THE INVENTION

In one aspect, disclosed is a compound of formula (I):

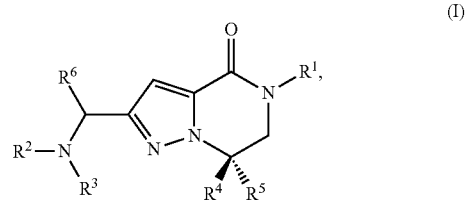

or a pharmaceutically acceptable salt thereof,
wherein
$R^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl;
$R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring;
$R^3$ is selected from the group consisting of hydrogen, $C_1$-$C_3$ alkyl, and $C_1$-$C_3$ fluoroalkyl;
$R^4$ and $R^5$ are each independently selected from the group consisting of hydrogen and $C_1$-$C_3$ alkyl; and
$R^6$ is selected from the group consisting of hydrogen, $C_1$-$C_3$ alkyl, and $C_1$-$C_3$ fluoroalkyl.

In certain embodiments, $R^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl; $R^2$ is selected from the group consisting of phenyl and pyridinyl, each optionally substituted with one to five substituents independently selected from halogen, cyano, alkoxy, fluoroalkoxy, hydroxyalkyl, hydroxyfluoroalkyl, alkoxyalkyl, alkoxyfluoroalkyl, cyanoalkyl, and cyanofluoroalkyl; $R^3$ is selected from the group consisting of $C_1$-$C_3$ alkyl and $C_1$-$C_3$ fluoroalkyl; $R^4$ and $R^5$ are each independently selected from the group consisting of hydrogen and $C_1$-$C_3$ alkyl; and $R^6$ is hydrogen.

In certain embodiments, $R^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$ is hydrogen; $R^4$ is $C_1$-$C_3$ alkyl; $R^5$ is hydrogen; and $R^6$ is hydrogen.

In certain embodiments, $R^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$ is hydrogen; $R^4$ is hydrogen; $R^5$ is hydrogen; and $R^6$ is hydrogen.

In certain embodiments, $R^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$ is hydrogen; $R^4$ is hydrogen; $R^5$ is hydrogen; and $R^6$ is selected from the group consisting of $C_1$-$C_3$ alkyl and $C_1$-$C_3$ fluoroalkyl.

In another aspect, disclosed are methods for treating a disease or disorder associated with dysfunction of metabotropic glutamate receptor 3 ($mGlu_3$), comprising administration of a therapeutically effective amount of a compound of formula (I) or a pharmaceutically acceptable salt thereof to a subject in need thereof.

In another aspect, disclosed is a compound of formula (I) or a pharmaceutically acceptable salt thereof, wherein the compound is a negative allosteric modulator of $mGlu_3$.

In another aspect, disclosed is a pharmaceutical composition comprising a therapeutically effective amount of a compound of formula (I) or a pharmaceutically acceptable salt thereof, in combination with one or more pharmaceutically acceptable carriers.

DETAILED DESCRIPTION

Disclosed herein are negative allosteric modulators (NAMs) of $mGlu_3$. The modulators can have formula (I). Compounds of formula (I) exhibit selectivity for $mGlu_3$ over other mGlu receptors, and in particular, $mGlu_5$. Compounds of formula (I) can be used to treat or prevent diseases and disorders associated with $mGlu_3$ by modulating $mGlu_3$ activity. $mGlu_3$ has been implicated in a number of different diseases and disorders including, but not limited to, depression, cognitive disorders, schizophrenia, Alzheimer's disease, and cancer, such as glioma.

Since the orthosteric binding sites of the mGlu isoforms are highly conserved, very few selective modulators of the mGlus that bind at the orthosteric site have been identified. One strategy to selectively bind and modulate the mGlus includes identifying allosteric sites which may be amenable to modulation by a small molecule. In particular, negative allosteric modulation of $mGlu_3$ can result in inhibition of processes governed by $mGlu_3$ and provide therapeutic benefits for disorders caused by $mGlu_3$ dysfunction.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkoxyalkyl" as used herein, refers to an alkoxy group, as defined herein, appended to the parent molecular moiety through an alkylene group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "alkyloxy" as used herein, means at least one alkyl group, as defined herein, is appended to the parent molecular moiety through an oxygen atom. Representative examples of alkyloxy include, but are not limited to, methoxy, ethoxy, and isopropoxy.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "cyanoalkyl" as used herein, means at least one —CN group, is appended to the parent molecular moiety through an alkylene group, as defined herein.

The term "cyanofluoroalkyl" as used herein, means at least one —CN group, is appended to the parent molecular moiety through a fluoroalkyl group, as defined herein.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. The cycloalkyl groups of this invention may be optionally substituted with 1, 2 or 3 alkyl substituents.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkyloxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" as used herein, means Cl, Br, I, or F.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, thiazolyl, and quinolinyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$] decane), and oxa-adamantane (2-oxatricyclo[3.3.1.1$^{3,7}$] decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy" as used herein, means an —OH group.

The term "hydroxyalkyl" as used herein, means at least one —OH group, is appended to the parent molecular moiety through an alkylene group, as defined herein.

The term "hydroxyfluoroalkyl" as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

In one aspect, disclosed is a compound of formula (I):

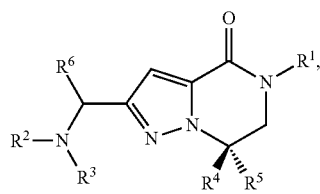

(I)

or a pharmaceutically acceptable salt thereof. $R^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl. $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring. $R^3$ is selected from the group consisting of hydrogen, $C_1$-$C_3$ alkyl, and $C_1$-$C_3$ fluoroalkyl. $R^4$ and $R^5$ are each independently selected from the group consisting of hydrogen and $C_1$-$C_3$ alkyl. $R^6$ is selected from the group consisting of hydrogen, $C_1$-$C_3$ alkyl, and $C_1$-$C_3$ fluoroalkyl.

In certain embodiments, $R^1$ is phenyl, optionally substituted with one to three substituents independently selected from halogen, cyano, alkyl, alkoxy, alkoxyalkyl, and fluoroalkoxy. In certain embodiments, $R^1$ is phenyl, optionally substituted with one to three substituents independently selected from fluoro, chloro, cyano, $C_1$-$C_3$-alkyl, $C_1$-$C_3$-alkoxy, $C_1$-$C_3$-alkoxy-$C_1$-$C_3$-alkyl, and fluoro-$C_1$-$C_3$-alkoxy. In certain embodiments, $R^1$ is 2-fluorophenyl, 2,3-difluorophenyl, 2,4-difluorophenyl, 2,5-difluorophenyl, 2,6-difluorophenyl, 2-fluoro-4-methylphenyl, 3-fluorophenyl, 3,4-difluorophenyl, 3,5-difluorophenyl, 3-fluoro-5-methoxyphenyl, 4-fluorophenyl, 4-fluoro-2-methylphenyl, 4-(difluoromethoxy)phenyl, 2-chlorophenyl, 3-chlorophenyl, 4-chlorophenyl, 2-chloro-3-fluorophenyl, 2-chloro-4-fluorophenyl, 2-chloro-5-fluorophenyl, 3-chloro-2-fluorophenyl, 3-chloro-4-fluorophenyl, 3-chloro-5-fluorophenyl, 3-chloro-5-methoxyphenyl, 4-chloro-2-fluorophenyl, 4-chloro-3-fluorophenyl, 4-chloro-2,6-difluorophenyl, 5-chloro-2-fluorophenyl, 2-cyanophenyl, 3-cyanophenyl, 5-cyanophenyl, 2-methylphenyl, 4-methylphenyl, 2-methoxyphenyl, 3-methoxyphenyl, 4-methoxyphenyl, or 4-(methoxymethyl)phenyl.

In certain embodiments, $R^1$ is pyridinyl, optionally substituted with one substituent selected from halogen and alkyl. In certain embodiments, $R^1$ is pyridinyl, optionally substituted with one substituent selected from fluoro, chloro, and $C_1$-$C_3$-alkyl. In certain embodiments, $R^1$ is pyridin-2-yl, pyridin-3-yl, 3-fluoropyridin-2-yl, 5-fluoropyridin-2-yl, 6-fluoropyridin-2-yl, 4-chloropyridin-2-yl, 5-chloropyridin-2-yl, or 5-methylpyridin-2-yl.

In certain embodiments, $R^1$ is thiazolyl, optionally substituted with one substituent selected from alkyl. In certain embodiments, $R^1$ is thiazolyl, optionally substituted with one substituent selected from $C_1$-$C_3$-alkyl. In certain embodiments, $R^1$ is 2-methylthiazol-4-yl, or 5-methylthiazol-2-yl.

In certain embodiments, $R^2$ is phenyl, optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring. In certain embodiments, $R^2$ is phenyl, optionally substituted with one to five substituents independently selected from fluoro, chloro, bromo, cyano, $C_1$-$C_3$-alkyl, fluoro-$C_1$-$C_3$-alkyl, $C_1$-$C_3$-alkoxy, fluoro-$C_1$-$C_3$-alkoxy, hydroxy-$C_1$-$C_3$-alkyl, hydroxyfluoro-$C_1$-$C_3$-alkyl, $C_1$-$C_3$-alkoxy-$C_1$-$C_3$-alkyl, $C_1$-$C_3$-alkoxyfluoro-$C_1$-$C_3$-alkyl, cyano-$C_1$-$C_3$-alkyl, and cyanofluoro-$C_1$-$C_3$-alkyl, or 2 of the substituents on adjacent carbons can together form a 2,2-difluorodioxolanyl. In certain embodiments, $R^2$ is phenyl, 2-fluorophenyl, 2,2-difluorobenzo[d][1,3]dioxol-5-yl, 2,3-difluorophenyl, 2,4-difluorophenyl, 2,5-difluorophenyl, 2,6-difluorophenyl, 2-fluoro-4-methylphenyl, 2,4,6-trifluorophenyl, 3-fluorophenyl, 3,4-difluorophenyl, 3,5-difluorophenyl, 3-(difluoromethoxy)phenyl, 4-fluorophenyl, 4-fluoro-3-methylphenyl, 4-(difluoromethoxy)phenyl, 4-(difluoromethoxy)-2-fluorophenyl, 4-(difluoromethoxy)-3-fluorophenyl, 4-trifluoromethyl, 4-(trifluoromethoxy)phenyl, 2-chlorophenyl, 3-chlorophenyl, 4-chlorophenyl, 4-chloro-2-fluorophenyl, 4-bromophenyl, 3-cyanophenyl, 4-cyanophenyl, 4-(cyanomethyl)phenyl, 2-methoxyphenyl, 3-methoxyphenyl, 4-methoxyphenyl, 2-methylphenyl, 3-methylphenyl, 4-methylphenyl, 4-ethylphenyl, 4-isopropylphenyl, 4-(tert-butyl)phenyl, or 4-(methyl sulfonyl)phenyl.

In certain embodiments, $R^2$ is pyridinyl, optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring. In certain embodiments, $R^2$ is pyridinyl, optionally substituted with one to five substituents independently selected from fluoro, chloro, bromo, cyano, $C_1$-$C_3$-alkyl, fluoro-$C_1$-$C_3$-alkyl, $C_1$-$C_3$-alkoxy, fluoro-$C_1$-$C_3$-alkoxy, hydroxy-$C_1$-$C_3$-alkyl, hydroxyfluoro-$C_1$-$C_3$-alkyl, $C_1$-$C_3$-alkoxy-$C_1$-$C_3$-alkyl, $C_1$-$C_3$-alkoxyfluoro-$C_1$-$C_3$-alkyl, cyano-$C_1$-$C_3$-alkyl, and cyanofluoro-$C_1$-$C_3$-alkyl, or 2 of the substituents on adjacent carbons can together form a 2,2-difluorodioxolanyl. In certain embodiments, $R^2$ is pyridin-2-yl, 3-fluoropyridin-2-yl, 5-fluoropyridin-2-yl, 3-(trifluoromethyl)pyridin-2-yl, 6-(trifluoromethyl)pyridin-2-yl, 3-chloropyridin-2-yl, 4-chloropyridin-2-yl, 5-chloropyridin-2-yl, 6-chloropyridin-2-yl, 3-methylpyridin-2-yl, 4-methylpyridin-2-yl, 5-methylpyridin-2-yl, or 6-methylpyridin-2-yl.

In certain embodiments, $R^3$ is hydrogen or methyl. In certain embodiments, $R^3$ is hydrogen. In certain embodiments, $R^3$ is methyl.

In certain embodiments, $R^4$ is hydrogen or methyl. In certain embodiments, $R^4$ is hydrogen. In certain embodiments, $R^4$ is methyl.

In certain embodiments, $R^5$ is hydrogen or methyl. In certain embodiments, $R^5$ is hydrogen. In certain embodiments, $R^5$ is methyl.

In certain embodiments, $R^6$ is hydrogen or methyl. In certain embodiments, $R^6$ is hydrogen. In certain embodiments, $R^6$ is methyl.

In certain embodiments, $R^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl; $R^2$ is selected from the group consisting of phenyl and pyridinyl, each optionally substituted with one to five substituents independently selected from halogen, cyano, alkoxy, fluoroalkoxy, hydroxyalkyl, hydroxyfluoroalkyl, alkoxyalkyl, alkoxyfluoroalkyl, cyanoalkyl, and cyanofluoroalkyl; $R^3$ is selected from the group consisting of $C_1$-$C_3$ alkyl and $C_1$-$C_3$ fluoroalkyl; $R^4$ and $R^5$ are each independently selected from the group consisting of hydrogen and $C_1$-$C_3$ alkyl; and $R^6$ is hydrogen. Representative compounds include, but are not limited to:

5-(4-fluorophenyl)-2-((methyl(phenyl)amino)methyl)-6,7-dihydropyrazolo[1,5-a]pyrazin-4(5H)-one;
5-(4-fluorophenyl)-2-(((2-fluorophenyl)(methyl)amino) methyl)-6,7-dihydropyrazolo[1,5-a]pyrazin-4(5H)-one;
2-(((2-chlorophenyl)(methyl)amino)methyl)-5-(4-fluorophenyl)-6,7-dihydropyrazolo[1,5-a]pyrazin-4(5H)-one;
5-(4-fluorophenyl)-2-(((2-methoxyphenyl)(methyl)amino) methyl)-6,7-dihydropyrazolo[1,5-a]pyrazin-4(5H)-one;
5-(4-fluorophenyl)-2-(((3-fluorophenyl)(methyl)amino) methyl)-6,7-dihydropyrazolo[1,5-a]pyrazin-4(5H)-one;
2-(((3-chlorophenyl)(methyl)amino)methyl)-5-(4-fluorophenyl)-6,7-dihydropyrazolo[1,5-a]pyrazin-4(5H)-one;
5-(4-fluorophenyl)-2-(((3-methoxyphenyl)(methyl)amino) methyl)-6,7-dihydropyrazolo[1,5-a]pyrazin-4(5H)-one;
5-(4-fluorophenyl)-2-(((4-fluorophenyl)(methyl)amino) methyl)-6,7-dihydropyrazolo[1,5-a]pyrazin-4(5H)-one;
2-(((4-chlorophenyl)(methyl)amino)methyl)-5-(4-fluorophenyl)-6,7-dihydropyrazolo[1,5-a]pyrazin-4(5H)-one;
2-(((4-bromophenyl)(methyl)amino)methyl)-5-(4-fluorophenyl)-6,7-dihydropyrazolo[1,5-a]pyrazin-4(5H)-one;
5-(4-fluorophenyl)-2-(((4-methoxyphenyl)(methyl)amino) methyl)-6,7-dihydropyrazolo[1,5-a]pyrazin-4(5H)-one;
4-(((5-(4-fluorophenyl)-4-oxo-4,5,6,7-tetrahydropyrazolo [1,5-a]pyrazin-2-yl)methyl)(methyl)amino)benzonitrile;
2-(((3,5-difluorophenyl)(methyl)amino)methyl)-5-(4-fluorophenyl)-6,7-dihydropyrazolo[1,5-a]pyrazin-4(5H)-one;
5-(4-chlorophenyl)-2-(((4-methoxyphenyl)(methyl)amino) methyl)-6,7-dihydropyrazolo[1,5-a]pyrazin-4(5H)-one;
5-(3,4-difluorophenyl)-2-(((4-methoxyphenyl)(methyl) amino)methyl)-6,7-dihydropyrazolo[1,5-a]pyrazin-4 (5H)-one;
5-(3-chlorophenyl)-2-(((4-methoxyphenyl)(methyl)amino) methyl)-6,7-dihydropyrazolo[1,5-a]pyrazin-4(5H)-one;
2-(((4-methoxyphenyl)(methyl)amino)methyl)-5-(p-tolyl)-6,7-dihydropyrazolo[1,5-a]pyrazin-4(5H)-one;
5-(2-chlorophenyl)-2-(((4-methoxyphenyl)(methyl)amino) methyl)-6,7-dihydropyrazolo[1,5-a]pyrazin-4(5H)-one;
5-(3-fluorophenyl)-2-(((4-methoxyphenyl)(methyl)amino) methyl)-6,7-dihydropyrazolo[1,5-a]pyrazin-4(5H)-one;
2-(((4-methoxyphenyl)(methyl)amino)methyl)-5-(2,4,6-trifluorophenyl)-6,7-dihydropyrazolo[1,5-a]pyrazin-4(5H)-one;
2-(((4-methoxyphenyl)(methyl)amino)methyl)-5-(m-tolyl)-6,7-dihydropyrazolo[1,5-a]pyrazin-4(5H)-one;
5-(3,5-difluorophenyl)-2-(((4-methoxyphenyl)(methyl) amino)methyl)-6,7-dihydropyrazolo[1,5-a]pyrazin-4 (5H)-one;
5-(2-fluorophenyl)-2-(((4-methoxyphenyl)(methyl)amino) methyl)-6,7-dihydropyrazolo[1,5-a]pyrazin-4(5H)-one;
5-(2,5-difluorophenyl)-2-(((4-methoxyphenyl)(methyl) amino)methyl)-6,7-dihydropyrazolo[1,5-a]pyrazin-4 (5H)-one;
5-(2,3-difluorophenyl)-2-(((4-methoxyphenyl)(methyl) amino)methyl)-6,7-dihydropyrazolo[1,5-a]pyrazin-4 (5H)-one;
5-(2-fluoro-4-methylphenyl)-2-(((4-methoxyphenyl) (methyl)amino)methyl)-6,7-dihydropyrazolo[1,5-a] pyrazin-4(5H)-one;
5-(4-fluoro-2-methylphenyl)-2-(((4-methoxyphenyl) (methyl)amino)methyl)-6,7-dihydropyrazolo[1,5-a] pyrazin-4(5H)-one;
5-(2,6-difluorophenyl)-2-(((4-methoxyphenyl)(methyl) amino)methyl)-6,7-dihydropyrazolo[1,5-a]pyrazin-4 (5H)-one;
2-(((4-methoxyphenyl)(methyl)amino)methyl)-5-(o-tolyl)-6,7-dihydropyrazolo[1,5-a]pyrazin-4(5H)-one;
2-(2-(((4-methoxyphenyl)(methyl)amino)methyl)-4-oxo-6, 7-dihydropyrazolo[1,5-a]pyrazin-5(4H)-yl)benzonitrile;
5-(3-methoxyphenyl)-2-(((4-methoxyphenyl)(methyl) amino)methyl)-6,7-dihydropyrazolo[1,5-a]pyrazin-4 (5H)-one;
5-(4-methoxyphenyl)-2-(((4-methoxyphenyl)(methyl) amino)methyl)-6,7-dihydropyrazolo[1,5-a]pyrazin-4 (5H)-one;
2-(((4-methoxyphenyl)(methyl)amino)methyl)-5-(2-methylthiazol-4-yl)-6,7-dihydropyrazolo[1,5-a]pyrazin-4 (5H)-one;
3-(2-(((4-methoxyphenyl)(methyl)amino)methyl)-4-oxo-6, 7-dihydropyrazolo[1,5-a]pyrazin-5(4H)-yl)benzonitrile;
2-(((4-methoxyphenyl)(methyl)amino)methyl)-5-(pyridin-2-yl)-6,7-dihydropyrazolo[1,5-a]pyrazin-4(5H)-one;
4-(2-(((4-methoxyphenyl)(methyl)amino)methyl)-4-oxo-6, 7-dihydropyrazolo[1,5-a]pyrazin-5(4H)-yl)benzonitrile;
5-(2-methoxyphenyl)-2-(((4-methoxyphenyl)(methyl) amino)methyl)-6,7-dihydropyrazolo[1,5-a]pyrazin-4 (5H)-one;
5-(4-(methoxymethyl)phenyl)-2-(((4-methoxyphenyl) (methyl)amino)methyl)-6,7-dihydropyrazolo[1,5-a] pyrazin-4(5H)-one;
2-(((4-methoxyphenyl)(methyl)amino)methyl)-5-(pyridin-3-yl)-6,7-dihydropyrazolo[1,5-a]pyrazin-4(5H)-one;

5-(5-fluoropyridin-2-yl)-2-(((4-methoxyphenyl)(methyl)amino)methyl)-6,7-dihydropyrazolo[1,5-a]pyrazin-4(5H)-one;
5-(4-(difluoromethoxy)phenyl)-2-(((4-methoxyphenyl)(methyl)amino)methyl)-6,7-dihydropyrazolo[1,5-a]pyrazin-4(5H)-one;
5-(5-chloropyridin-2-yl)-2-(((4-methoxyphenyl)(methyl)amino)methyl)-6,7-dihydropyrazolo[1,5-a]pyrazin-4(5H)-one;
5-(3,4-difluorophenyl)-2-((ethyl(4-methoxyphenyl)amino)methyl)-6,7-dihydropyrazolo[1,5-a]pyrazin-4(5H)-one;
5-(3,4-difluorophenyl)-2-(((4-methoxyphenyl)(propyl)amino)methyl)-6,7-dihydropyrazolo[1,5-a]pyrazin-4(5H)-one;
5-(4-chloro-2-fluorophenyl)-2-(((4-methoxyphenyl)(methyl)amino)methyl)-6,7-dihydropyrazolo[1,5-a]pyrazin-4(5H)-one;
5-(2-chloro-3-fluorophenyl)-2-(((4-methoxyphenyl)(methyl)amino)methyl)-6,7-dihydropyrazolo[1,5-a]pyrazin-4(5H)-one;
5-(5-chloro-2-fluorophenyl)-2-(((4-methoxyphenyl)(methyl)amino)methyl)-6,7-dihydropyrazolo[1,5-a]pyrazin-4(5H)-one;
5-(4-chloro-2,6-difluorophenyl)-2-(((4-methoxyphenyl)(methyl)amino)methyl)-6,7-dihydropyrazolo[1,5-a]pyrazin-4(5H)-one;
5-(2-chloro-5-fluorophenyl)-2-(((4-methoxyphenyl)(methyl)amino)methyl)-6,7-dihydropyrazolo[1,5-a]pyrazin-4(5H)-one;
5-(2-chloro-4-fluorophenyl)-2-(((4-methoxyphenyl)(methyl)amino)methyl)-6,7-dihydropyrazolo[1,5-a]pyrazin-4(5H)-one;
5-(3-chloro-5-fluorophenyl)-2-(((4-methoxyphenyl)(methyl)amino)methyl)-6,7-dihydropyrazolo[1,5-a]pyrazin-4(5H)-one;
5-(3-fluoro-5-methoxyphenyl)-2-(((4-methoxyphenyl)(methyl)amino)methyl)-6,7-dihydropyrazolo[1,5-a]pyrazin-4(5H)-one;
5-(3-chloro-4-fluorophenyl)-2-(((4-methoxyphenyl)(methyl)amino)methyl)-6,7-dihydropyrazolo[1,5-a]pyrazin-4(5H)-one;
5-(3-chloro-5-methoxyphenyl)-2-(((4-methoxyphenyl)(methyl)amino)methyl)-6,7-dihydropyrazolo[1,5-a]pyrazin-4(5H)-one;
5-(3-chloro-2-fluorophenyl)-2-(((4-methoxyphenyl)(methyl)amino)methyl)-6,7-dihydropyrazolo[1,5-a]pyrazin-4(5H)-one; and
5-(4-chloro-3-fluorophenyl)-2-(((4-methoxyphenyl)(methyl)amino)methyl)-6,7-dihydropyrazolo[1,5-a]pyrazin-4(5H)-one;
and pharmaceutically acceptable salts thereof.

In certain embodiments, $R^1$ is phenyl, optionally substituted with one to three substituents independently selected from halogen, cyano, alkyl, alkoxy, alkoxyalkyl, fluoroalkoxy; $R^2$ is selected from the group consisting of phenyl and pyridinyl, each optionally substituted with one to five substituents independently selected from halogen, cyano, alkoxy, fluoroalkoxy, hydroxyalkyl, hydroxyfluoroalkyl, alkoxyalkyl, alkoxyfluoroalkyl, cyanoalkyl, and cyanofluoroalkyl; $R^3$ is selected from the group consisting of $C_1$-$C_3$ alkyl and $C_1$-$C_3$ fluoroalkyl; $R^4$ and $R^5$ are each independently selected from the group consisting of hydrogen and $C_1$-$C_3$ alkyl; and $R^6$ is hydrogen.

In certain embodiments, $R^1$ is pyridinyl, optionally substituted with one substituent selected from halogen and alkyl; $R^2$ is selected from the group consisting of phenyl and pyridinyl, each optionally substituted with one to five substituents independently selected from halogen, cyano, alkoxy, fluoroalkoxy, hydroxyalkyl, hydroxyfluoroalkyl, alkoxyalkyl, alkoxyfluoroalkyl, cyanoalkyl, and cyanofluoroalkyl; $R^3$ is selected from the group consisting of $C_1$-$C_3$ alkyl and $C_1$-$C_3$ fluoroalkyl; $R^4$ and $R^5$ are each independently selected from the group consisting of hydrogen and $C_1$-$C_3$ alkyl; and $R^6$ is hydrogen.

In certain embodiments, $R^1$ is thiazolyl, optionally substituted with one substituent selected from alkyl; $R^2$ is selected from the group consisting of phenyl and pyridinyl, each optionally substituted with one to five substituents independently selected from halogen, cyano, alkoxy, fluoroalkoxy, hydroxyalkyl, hydroxyfluoroalkyl, alkoxyalkyl, alkoxyfluoroalkyl, cyanoalkyl, and cyanofluoroalkyl; $R^3$ is selected from the group consisting of $C_1$-$C_3$ alkyl and $C_1$-$C_3$ fluoroalkyl; $R^4$ and $R^5$ are each independently selected from the group consisting of hydrogen and $C_1$-$C_3$ alkyl; and $R^6$ is hydrogen.

In a preferred embodiment, $R^2$ is

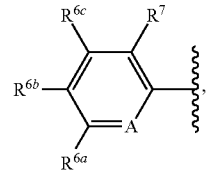

wherein
A is selected from the group consisting of N, CH, and CF; $R^{6a-c}$ are independently selected from the group consisting of hydrogen, fluorine, chlorine, bromine, cyano, methoxy, difluoromethoxy, —$CR^8R^9OH$, —$CR^8R^9OCH_3$, and —$CR^8R^9CN$; $R^8$ and $R^9$ are each independently selected from hydrogen, fluorine, and methyl; $R^7$ is selected from the group consisting of hydrogen, fluorine, and chlorine; and $R^1$, $R^3$, $R^4$, $R^5$, and $R^6$ are as defined according to any of the previous embodiments. Representative compounds include, but are not limited to:
5-(4-fluorophenyl)-2-((methyl(phenyl)amino)methyl)-6,7-dihydropyrazolo[1,5-a]pyrazin-4(5H)-one;
5-(4-fluorophenyl)-2-(((2-fluorophenyl)(methyl)amino)methyl)-6,7-dihydropyrazolo[1,5-a]pyrazin-4(5H)-one;
2-(((2-chlorophenyl)(methyl)amino)methyl)-5-(4-fluorophenyl)-6,7-dihydropyrazolo[1,5-a]pyrazin-4(5H)-one;
5-(4-fluorophenyl)-2-(((3-fluorophenyl)(methyl)amino)methyl)-6,7-dihydropyrazolo[1,5-a]pyrazin-4(5H)-one;
2-(((3-chlorophenyl)(methyl)amino)methyl)-5-(4-fluorophenyl)-6,7-dihydropyrazolo[1,5-a]pyrazin-4(5H)-one;
5-(4-fluorophenyl)-2-(((3-methoxyphenyl)(methyl)amino)methyl)-6,7-dihydropyrazolo[1,5-a]pyrazin-4(5H)-one;
5-(4-fluorophenyl)-2-(((4-fluorophenyl)(methyl)amino)methyl)-6,7-dihydropyrazolo[1,5-a]pyrazin-4(5H)-one;
2-(((4-chlorophenyl)(methyl)amino)methyl)-5-(4-fluorophenyl)-6,7-dihydropyrazolo[1,5-a]pyrazin-4(5H)-one;
2-(((4-bromophenyl)(methyl)amino)methyl)-5-(4-fluorophenyl)-6,7-dihydropyrazolo[1,5-a]pyrazin-4(5H)-one;
5-(4-fluorophenyl)-2-(((4-methoxyphenyl)(methyl)amino)methyl)-6,7-dihydropyrazolo[1,5-a]pyrazin-4(5H)-one;
4-(((5-(4-fluorophenyl)-4-oxo-4,5,6,7-tetrahydropyrazolo[1,5-a]pyrazin-2-yl)methyl)(methyl)amino)benzonitrile;
2-(((3,5-difluorophenyl)(methyl)amino)methyl)-5-(4-fluorophenyl)-6,7-dihydropyrazolo[1,5-a]pyrazin-4(5H)-one;
5-(4-chlorophenyl)-2-(((4-methoxyphenyl)(methyl)amino)methyl)-6,7-dihydropyrazolo[1,5-a]pyrazin-4(5H)-one;

5-(3,4-difluorophenyl)-2-(((4-methoxyphenyl)(methyl)amino)methyl)-6,7-dihydropyrazolo[1,5-a]pyrazin-4(5H)-one;
5-(3-chlorophenyl)-2-(((4-methoxyphenyl)(methyl)amino)methyl)-6,7-dihydropyrazolo[1,5-a]pyrazin-4(5H)-one;
2-(((4-methoxyphenyl)(methyl)amino)methyl)-5-(p-tolyl)-6,7-dihydropyrazolo[1,5-a]pyrazin-4(5H)-one;
5-(2-chlorophenyl)-2-(((4-methoxyphenyl)(methyl)amino)methyl)-6,7-dihydropyrazolo[1,5-a]pyrazin-4(5H)-one;
5-(3-fluorophenyl)-2-(((4-methoxyphenyl)(methyl)amino)methyl)-6,7-dihydropyrazolo[1,5-a]pyrazin-4(5H)-one;
2-(((4-methoxyphenyl)(methyl)amino)methyl)-5-(2,4,6-trifluorophenyl)-6,7-dihydropyrazolo[1,5-a]pyrazin-4(5H)-one;
2-(((4-methoxyphenyl)(methyl)amino)methyl)-5-(m-tolyl)-6,7-dihydropyrazolo[1,5-a]pyrazin-4(5H)-one;
5-(3,5-difluorophenyl)-2-(((4-methoxyphenyl)(methyl)amino)methyl)-6,7-dihydropyrazolo[1,5-a]pyrazin-4(5H)-one;
5-(2-fluorophenyl)-2-(((4-methoxyphenyl)(methyl)amino)methyl)-6,7-dihydropyrazolo[1,5-a]pyrazin-4(5H)-one;
5-(2,5-difluorophenyl)-2-(((4-methoxyphenyl)(methyl)amino)methyl)-6,7-dihydropyrazolo[1,5-a]pyrazin-4(5H)-one;
5-(2,3-difluorophenyl)-2-(((4-methoxyphenyl)(methyl)amino)methyl)-6,7-dihydropyrazolo[1,5-a]pyrazin-4(5H)-one;
5-(2-fluoro-4-methylphenyl)-2-(((4-methoxyphenyl)(methyl)amino)methyl)-6,7-dihydropyrazolo[1,5-a]pyrazin-4(5H)-one;
5-(4-fluoro-2-methylphenyl)-2-(((4-methoxyphenyl)(methyl)amino)methyl)-6,7-dihydropyrazolo[1,5-a]pyrazin-4(5H)-one;
5-(2,6-difluorophenyl)-2-(((4-methoxyphenyl)(methyl)amino)methyl)-6,7-dihydropyrazolo[1,5-a]pyrazin-4(5H)-one;
2-(((4-methoxyphenyl)(methyl)amino)methyl)-5-(o-tolyl)-6,7-dihydropyrazolo[1,5-a]pyrazin-4(5H)-one;
2-(2-(((4-methoxyphenyl)(methyl)amino)methyl)-4-oxo-6,7-dihydropyrazolo[1,5-a]pyrazin-5(4H)-yl)benzonitrile;
5-(3-methoxyphenyl)-2-(((4-methoxyphenyl)(methyl)amino)methyl)-6,7-dihydropyrazolo[1,5-a]pyrazin-4(5H)-one;
5-(4-methoxyphenyl)-2-(((4-methoxyphenyl)(methyl)amino)methyl)-6,7-dihydropyrazolo[1,5-a]pyrazin-4(5H)-one;
2-(((4-methoxyphenyl)(methyl)amino)methyl)-5-(2-methylthiazol-4-yl)-6,7-dihydropyrazolo[1,5-a]pyrazin-4(5H)-one;
3-(2-(((4-methoxyphenyl)(methyl)amino)methyl)-4-oxo-6,7-dihydropyrazolo[1,5-a]pyrazin-5(4H)-yl)benzonitrile;
2-(((4-methoxyphenyl)(methyl)amino)methyl)-5-(pyridin-2-yl)-6,7-dihydropyrazolo[1,5-a]pyrazin-4(5H)-one;
4-(2-(((4-methoxyphenyl)(methyl)amino)methyl)-4-oxo-6,7-dihydropyrazolo[1,5-a]pyrazin-5(4H)-yl)benzonitrile;
5-(2-methoxyphenyl)-2-(((4-methoxyphenyl)(methyl)amino)methyl)-6,7-dihydropyrazolo[1,5-a]pyrazin-4(5H)-one;
5-(4-(methoxymethyl)phenyl)-2-(((4-methoxyphenyl)(methyl)amino)methyl)-6,7-dihydropyrazolo[1,5-a]pyrazin-4(5H)-one;
2-(((4-methoxyphenyl)(methyl)amino)methyl)-5-(pyridin-3-yl)-6,7-dihydropyrazolo[1,5-a]pyrazin-4(5H)-one;
5-(5-fluoropyridin-2-yl)-2-(((4-methoxyphenyl)(methyl)amino)methyl)-6,7-dihydropyrazolo[1,5-a]pyrazin-4(5H)-one;
5-(4-(difluoromethoxy)phenyl)-2-(((4-methoxyphenyl)(methyl)amino)methyl)-6,7-dihydropyrazolo[1,5-a]pyrazin-4(5H)-one;
5-(5-chloropyridin-2-yl)-2-(((4-methoxyphenyl)(methyl)amino)methyl)-6,7-dihydropyrazolo[1,5-a]pyrazin-4(5H)-one;
5-(3,4-difluorophenyl)-2-((ethyl(4-methoxyphenyl)amino)methyl)-6,7-dihydropyrazolo[1,5-a]pyrazin-4(5H)-one;
5-(3,4-difluorophenyl)-2-(((4-methoxyphenyl)(propyl)amino)methyl)-6,7-dihydropyrazolo[1,5-a]pyrazin-4(5H)-one;
5-(4-chloro-2-fluorophenyl)-2-(((4-methoxyphenyl)(methyl)amino)methyl)-6,7-dihydropyrazolo[1,5-a]pyrazin-4(5H)-one;
5-(2-chloro-3-fluorophenyl)-2-(((4-methoxyphenyl)(methyl)amino)methyl)-6,7-dihydropyrazolo[1,5-a]pyrazin-4(5H)-one;
5-(5-chloro-2-fluorophenyl)-2-(((4-methoxyphenyl)(methyl)amino)methyl)-6,7-dihydropyrazolo[1,5-a]pyrazin-4(5H)-one;
5-(4-chloro-2,6-difluorophenyl)-2-(((4-methoxyphenyl)(methyl)amino)methyl)-6,7-dihydropyrazolo[1,5-a]pyrazin-4(5H)-one;
5-(2-chloro-5-fluorophenyl)-2-(((4-methoxyphenyl)(methyl)amino)methyl)-6,7-dihydropyrazolo[1,5-a]pyrazin-4(5H)-one;
5-(2-chloro-4-fluorophenyl)-2-(((4-methoxyphenyl)(methyl)amino)methyl)-6,7-dihydropyrazolo[1,5-a]pyrazin-4(5H)-one;
5-(3-chloro-5-fluorophenyl)-2-(((4-methoxyphenyl)(methyl)amino)methyl)-6,7-dihydropyrazolo[1,5-a]pyrazin-4(5H)-one;
5-(3-fluoro-5-methoxyphenyl)-2-(((4-methoxyphenyl)(methyl)amino)methyl)-6,7-dihydropyrazolo[1,5-a]pyrazin-4(5H)-one;
5-(3-chloro-4-fluorophenyl)-2-(((4-methoxyphenyl)(methyl)amino)methyl)-6,7-dihydropyrazolo[1,5-a]pyrazin-4(5H)-one;
5-(3-chloro-5-methoxyphenyl)-2-(((4-methoxyphenyl)(methyl)amino)methyl)-6,7-dihydropyrazolo[1,5-a]pyrazin-4(5H)-one;
5-(3-chloro-2-fluorophenyl)-2-(((4-methoxyphenyl)(methyl)amino)methyl)-6,7-dihydropyrazolo[1,5-a]pyrazin-4(5H)-one; and
5-(4-chloro-3-fluorophenyl)-2-(((4-methoxyphenyl)(methyl)amino)methyl)-6,7-dihydropyrazolo[1,5-a]pyrazin-4(5H)-one;
and pharmaceutically acceptable salts thereof.

In certain embodiments, $R^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$ is hydrogen; $R^4$ is $C_1$-$C_3$ alkyl; and $R^5$ and $R^6$ are hydrogen. In certain embodiments, $R^4$ is methyl. Representative compounds include, but are not limited to:

(R)-5-(4-fluorophenyl)-7-methyl-2-((phenylamino)methyl)-6,7-dihydropyrazolo[1,5-a]pyrazin-4(5H)-one;
(R)-5-(4-fluorophenyl)-2-(((2-fluorophenyl)amino)methyl)-7-methyl-6,7-dihydropyrazolo[1,5-a]pyrazin-4(5H)-one;
(R)-5-(4-fluorophenyl)-7-methyl-2-((o-tolylamino)methyl)-6,7-dihydropyrazolo[1,5-a]pyrazin-4(5H)-one;
(R)-5-(4-fluorophenyl)-2-(((3-fluorophenyl)amino)methyl)-7-methyl-6,7-dihydropyrazolo[1,5-a]pyrazin-4(5H)-one;
(R)-2-(((3-chlorophenyl)amino)methyl)-5-(4-fluorophenyl)-7-methyl-6,7-dihydropyrazolo[1,5-a]pyrazin-4(5H)-one;
(R)-5-(4-fluorophenyl)-7-methyl-2-((m-tolylamino)methyl)-6,7-dihydropyrazolo[1,5-a]pyrazin-4(5H)-one;
(R)-5-(4-fluorophenyl)-2-(((3-methoxyphenyl)amino)methyl)-7-methyl-6,7-dihydropyrazolo[1,5-a]pyrazin-4(5H)-one;
(R)-2-(((3-(difluoromethoxy)phenyl)amino)methyl)-5-(4-fluorophenyl)-7-methyl-6,7-dihydropyrazolo[1,5-a]pyrazin-4(5H)-one;
(R)-5-(4-fluorophenyl)-2-(((4-fluorophenyl)amino)methyl)-7-methyl-6,7-dihydropyrazolo[1,5-a]pyrazin-4(5H)-one;
(R)-5-(4-fluorophenyl)-7-methyl-2-((p-tolylamino)methyl)-6,7-dihydropyrazolo[1,5-a]pyrazin-4(5H)-one;
(R)-2-(((4-chlorophenyl)amino)methyl)-5-(4-fluorophenyl)-7-methyl-6,7-dihydropyrazolo[1,5-a]pyrazin-4(5H)-one;
(R)-5-(4-fluorophenyl)-2-(((4-methoxyphenyl)amino)methyl)-7-methyl-6,7-dihydropyrazolo[1,5-a]pyrazin-4(5H)-one;
(R)-2-(((4-(difluoromethoxy)phenyl)amino)methyl)-5-(4-fluorophenyl)-7-methyl-6,7-dihydropyrazolo[1,5-a]pyrazin-4(5H)-one;
(R)-2-(4-(((5-(4-fluorophenyl)-7-methyl-4-oxo-4,5,6,7-tetrahydropyrazolo[1,5-a]pyrazin-2-yl)methyl)amino)phenyl)acetonitrile;
(R)-2-(((2,3-difluorophenyl)amino)methyl)-5-(4-fluorophenyl)-7-methyl-6,7-dihydropyrazolo[1,5-a]pyrazin-4(5H)-one;
(R)-2-(((2,5-difluorophenyl)amino)methyl)-5-(4-fluorophenyl)-7-methyl-6,7-dihydropyrazolo[1,5-a]pyrazin-4(5H)-one;
(R)-2-(((2,6-difluorophenyl)amino)methyl)-5-(4-fluorophenyl)-7-methyl-6,7-dihydropyrazolo[1,5-a]pyrazin-4(5H)-one;
(R)-2-(((2,4-difluorophenyl)amino)methyl)-5-(4-fluorophenyl)-7-methyl-6,7-dihydropyrazolo[1,5-a]pyrazin-4(5H)-one;
(R)-2-(((3,4-difluorophenyl)amino)methyl)-5-(4-fluorophenyl)-7-methyl-6,7-dihydropyrazolo[1,5-a]pyrazin-4(5H)-one; and
(R)-5-(4-fluorophenyl)-7-methyl-2-(((2,4,6-trifluorophenyl)amino)methyl)-6,7-dihydropyrazolo[1,5-a]pyrazin-4(5H)-one;
and pharmaceutically acceptable salts thereof.

In certain embodiments, $R^1$ is phenyl, optionally substituted with one to three substituents independently selected from halogen, cyano, alkyl, alkoxy, alkoxyalkyl, fluoroalkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$ is hydrogen; $R^4$ is $C_1$-$C_3$ alkyl; and $R^5$ and $R^6$ are hydrogen. In certain embodiments, $R^4$ is methyl.

In certain embodiments, $R^1$ is pyridinyl, optionally substituted with one substituent selected from halogen and alkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$ is hydrogen; $R^4$ is $C_1$-$C_3$ alkyl; and $R^5$ and $R^6$ are hydrogen. In certain embodiments, $R^4$ is methyl.

In certain embodiments, $R^1$ is thiazolyl, optionally substituted with one substituent selected from alkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$ is hydrogen; $R^4$ is $C_1$-$C_3$ alkyl; and $R^5$ and $R^6$ are hydrogen. In certain embodiments, $R^4$ is methyl.

In a preferred embodiment, $R^2$ is

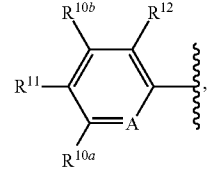

wherein
A is selected from the group consisting of N, CH, and CF; $R^{10a}$ and $R^{10b}$ are independently selected from the group consisting of hydrogen, fluorine, chlorine, cyano, methyl, and methoxy; $R^{11}$ is selected from the group consisting of hydrogen, fluorine, chlorine, cyano, methyl, ethyl, methoxy, difluoromethoxy, —$CR^{13}R^{14}OH$, —$CR^{13}R^{14}OCH_3$, and —$CR^{13}R^{14}CN$; $R^{13}$ and $R^{14}$ are each independently selected from hydrogen, fluorine, and methyl; $R^{12}$ is selected from the group consisting of hydrogen, fluorine, and chlorine; and $R^1$, $R^3$, $R^4$, $R^5$, and $R^6$ are as defined according to any of the previous embodiments; wherein $R^2$ is not unsubstituted phenyl or unsubstituted pyridinyl. Representative compounds include, but are not limited to:
(R)-5-(4-fluorophenyl)-2-(((2-fluorophenyl)amino)methyl)-7-methyl-6,7-dihydropyrazolo[1,5-a]pyrazin-4(5H)-one;
(R)-5-(4-fluorophenyl)-2-(((3-fluorophenyl)amino)methyl)-7-methyl-6,7-dihydropyrazolo[1,5-a]pyrazin-4(5H)-one;
(R)-2-(((3-chlorophenyl)amino)methyl)-5-(4-fluorophenyl)-7-methyl-6,7-dihydropyrazolo[1,5-a]pyrazin-4(5H)-one;
(R)-5-(4-fluorophenyl)-7-methyl-2-((m-tolylamino)methyl)-6,7-dihydropyrazolo[1,5-a]pyrazin-4(5H)-one;
(R)-5-(4-fluorophenyl)-2-(((3-methoxyphenyl)amino)methyl)-7-methyl-6,7-dihydropyrazolo[1,5-a]pyrazin-4(5H)-one;
(R)-2-(((3-(difluoromethoxy)phenyl)amino)methyl)-5-(4-fluorophenyl)-7-methyl-6,7-dihydropyrazolo[1,5-a]pyrazin-4(5H)-one;
(R)-5-(4-fluorophenyl)-2-(((4-fluorophenyl)amino)methyl)-7-methyl-6,7-dihydropyrazolo[1,5-a]pyrazin-4(5H)-one;
(R)-5-(4-fluorophenyl)-7-methyl-2-((p-tolylamino)methyl)-6,7-dihydropyrazolo[1,5-a]pyrazin-4(5H)-one;

(R)-2-(((4-chlorophenyl)amino)methyl)-5-(4-fluorophenyl)-7-methyl-6,7-dihydropyrazolo[1,5-a]pyrazin-4(5H)-one;
(R)-5-(4-fluorophenyl)-2-(((4-methoxyphenyl)amino)methyl)-7-methyl-6,7-dihydropyrazolo[1,5-a]pyrazin-4(5H)-one;
(R)-2-(((4-(difluoromethoxy)phenyl)amino)methyl)-5-(4-fluorophenyl)-7-methyl-6,7-dihydropyrazolo[1,5-a]pyrazin-4(5H)-one;
(R)-2-(4-(((5-(4-fluorophenyl)-7-methyl-4-oxo-4,5,6,7-tetrahydropyrazolo[1,5-a]pyrazin-2-yl)methyl)amino)phenyl)acetonitrile;
(R)-2-(((2,3-difluorophenyl)amino)methyl)-5-(4-fluorophenyl)-7-methyl-6,7-dihydropyrazolo[1,5-a]pyrazin-4(5H)-one;
(R)-2-(((2,5-difluorophenyl)amino)methyl)-5-(4-fluorophenyl)-7-methyl-6,7-dihydropyrazolo[1,5-a]pyrazin-4(5H)-one;
(R)-2-(((2,6-difluorophenyl)amino)methyl)-5-(4-fluorophenyl)-7-methyl-6,7-dihydropyrazolo[1,5-a]pyrazin-4(5H)-one;
(R)-2-(((2,4-difluorophenyl)amino)methyl)-5-(4-fluorophenyl)-7-methyl-6,7-dihydropyrazolo[1,5-a]pyrazin-4(5H)-one;
(R)-2-(((3,4-difluorophenyl)amino)methyl)-5-(4-fluorophenyl)-7-methyl-6,7-dihydropyrazolo[1,5-a]pyrazin-4(5H)-one; and
(R)-5-(4-fluorophenyl)-7-methyl-2-(((2,4,6-trifluorophenyl)amino)methyl)-6,7-dihydropyrazolo[1,5-a]pyrazin-4(5H)-one;
and pharmaceutically acceptable salts thereof.

In certain embodiments, $R^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; and $R^3$, $R^4$, $R^5$, and $R^6$ are hydrogen. Representative compounds include, but are not limited to:
5-(4-fluorophenyl)-2-((phenylamino)methyl)-6,7-dihydropyrazolo[1,5-a]pyrazin-4(5H)-one;
5-(4-fluorophenyl)-2-(((2-fluorophenyl)amino)methyl)-6,7-dihydropyrazolo[1,5-a]pyrazin-4(5H)-one;
5-(4-fluorophenyl)-2-((o-tolylamino)methyl)-6,7-dihydropyrazolo[1,5-a]pyrazin-4(5H)-one;
2-(((2-chlorophenyl)amino)methyl)-5-(4-fluorophenyl)-6,7-dihydropyrazolo[1,5-a]pyrazin-4(5H)-one;
5-(4-fluorophenyl)-2-(((2-methoxyphenyl)amino)methyl)-6,7-dihydropyrazolo[1,5-a]pyrazin-4(5H)-one;
5-(4-fluorophenyl)-2-(((3-fluorophenyl)amino)methyl)-6,7-dihydropyrazolo[1,5-a]pyrazin-4(5H)-one;
5-(4-fluorophenyl)-2-((m-tolylamino)methyl)-6,7-dihydropyrazolo[1,5-a]pyrazin-4(5H)-one;
2-(((3-chlorophenyl)amino)methyl)-5-(4-fluorophenyl)-6,7-dihydropyrazolo[1,5-a]pyrazin-4(5H)-one;
5-(4-fluorophenyl)-2-(((3-methoxyphenyl)amino)methyl)-6,7-dihydropyrazolo[1,5-a]pyrazin-4(5H)-one;
3-(((5-(4-fluorophenyl)-4-oxo-4,5,6,7-tetrahydropyrazolo[1,5-a]pyrazin-2-yl)methyl)amino)benzonitrile;
2-(((3-(difluoromethoxy)phenyl)amino)methyl)-5-(4-fluorophenyl)-6,7-dihydropyrazolo[1,5-a]pyrazin-4(5H)-one;
5-(4-fluorophenyl)-2-(((4-fluorophenyl)amino)methyl)-6,7-dihydropyrazolo[1,5-a]pyrazin-4(5H)-one;
5-(4-fluorophenyl)-2-((p-tolylamino)methyl)-6,7-dihydropyrazolo[1,5-a]pyrazin-4(5H)-one;
2-(((4-chlorophenyl)amino)methyl)-5-(4-fluorophenyl)-6,7-dihydropyrazolo[1,5-a]pyrazin-4(5H)-one;
2-(((4-bromophenyl)amino)methyl)-5-(4-fluorophenyl)-6,7-dihydropyrazolo[1,5-a]pyrazin-4(5H)-one;
5-(4-fluorophenyl)-2-(((4-methoxyphenyl)amino)methyl)-6,7-dihydropyrazolo[1,5-a]pyrazin-4(5H)-one;
4-(((5-(4-fluorophenyl)-4-oxo-4,5,6,7-tetrahydropyrazolo[1,5-a]pyrazin-2-yl)methyl)amino)benzonitrile;
5-(4-fluorophenyl)-2-(((4-(trifluoromethyl)phenyl)amino)methyl)-6,7-dihydropyrazolo[1,5-a]pyrazin-4(5H)-one;
2-(((4-(difluoromethoxy)phenyl)amino)methyl)-5-(4-fluorophenyl)-6,7-dihydropyrazolo[1,5-a]pyrazin-4(5H)-one;
5-(4-fluorophenyl)-2-(((4-(trifluoromethoxy)phenyl)amino)methyl)-6,7-dihydropyrazolo[1,5-a]pyrazin-4(5H)-one;
2-(((4-ethylphenyl)amino)methyl)-5-(4-fluorophenyl)-6,7-dihydropyrazolo[1,5-a]pyrazin-4(5H)-one;
5-(4-fluorophenyl)-2-(((4-isopropylphenyl)amino)methyl)-6,7-dihydropyrazolo[1,5-a]pyrazin-4(5H)-one;
2-(((4-(tert-butyl)phenyl)amino)methyl)-5-(4-fluorophenyl)-6,7-dihydropyrazolo[1,5-a]pyrazin-4(5H)-one;
5-(4-fluorophenyl)-2-(((4-(methylsulfonyl)phenyl)amino)methyl)-6,7-dihydropyrazolo[1,5-a]pyrazin-4(5H)-one;
2-(4-(((5-(4-fluorophenyl)-4-oxo-4,5,6,7-tetrahydropyrazolo[1,5-a]pyrazin-2-yl)methyl)amino)phenyl)acetonitrile;
2-(((2,3-difluorophenyl)amino)methyl)-5-(4-fluorophenyl)-6,7-dihydropyrazolo[1,5-a]pyrazin-4(5H)-one;
2-(((2,4-difluorophenyl)amino)methyl)-5-(4-fluorophenyl)-6,7-dihydropyrazolo[1,5-a]pyrazin-4(5H)-one;
2-(((2,5-difluorophenyl)amino)methyl)-5-(4-fluorophenyl)-6,7-dihydropyrazolo[1,5-a]pyrazin-4(5H)-one;
2-(((3,5-difluorophenyl)amino)methyl)-5-(4-fluorophenyl)-6,7-dihydropyrazolo[1,5-a]pyrazin-4(5H)-one;
2-(((3,4-difluorophenyl)amino)methyl)-5-(4-fluorophenyl)-6,7-dihydropyrazolo[1,5-a]pyrazin-4(5H)-one;
2-(((2,6-difluorophenyl)amino)methyl)-5-(4-fluorophenyl)-6,7-dihydropyrazolo[1,5-a]pyrazin-4(5H)-one;
5-(4-fluorophenyl)-2-(((2,4,6-trifluorophenyl)amino)methyl)-6,7-dihydropyrazolo[1,5-a]pyrazin-4(5H)-one;
2-(((4-chloro-2-fluorophenyl)amino)methyl)-5-(4-fluorophenyl)-6,7-dihydropyrazolo[1,5-a]pyrazin-4(5H)-one;
2-(((2-fluoro-4-methylphenyl)amino)methyl)-5-(4-fluorophenyl)-6,7-dihydropyrazolo[1,5-a]pyrazin-4(5H)-one;
2-(((4-fluoro-3-methylphenyl)amino)methyl)-5-(4-fluorophenyl)-6,7-dihydropyrazolo[1,5-a]pyrazin-4(5H)-one;
2-(((4-(difluoromethoxy)-2-fluorophenyl)amino)methyl)-5-(4-fluorophenyl)-6,7-dihydropyrazolo[1,5-a]pyrazin-4(5H)-one;
2-(((4-(difluoromethoxy)-3-fluorophenyl)amino)methyl)-5-(4-fluorophenyl)-6,7-dihydropyrazolo[1,5-a]pyrazin-4(5H)-one;
2-(((2,2-difluorobenzo[d][1,3]dioxol-5-yl)amino)methyl)-5-(4-fluorophenyl)-6,7-dihydropyrazolo[1,5-a]pyrazin-4(5H)-one;
5-(4-fluorophenyl)-2-(((5-fluoropyridin-2-yl)amino)methyl)-6,7-dihydropyrazolo[1,5-a]pyrazin-4(5H)-one;
5-(4-fluorophenyl)-2-((pyridin-2-ylamino)methyl)-6,7-dihydropyrazolo[1,5-a]pyrazin-4(5H)-one;
5-(4-fluorophenyl)-2-(((6-methylpyridin-2-yl)amino)methyl)-6,7-dihydropyrazolo[1,5-a]pyrazin-4(5H)-one;

2-(((5-chloropyridin-2-yl)amino)methyl)-5-(4-fluorophenyl)-6,7-dihydropyrazolo[1,5-a]pyrazin-4(5H)-one;
5-(4-fluorophenyl)-2-(((5-methylpyridin-2-yl)amino)methyl)-6,7-dihydropyrazolo[1,5-a]pyrazin-4(5H)-one;
5-(4-fluorophenyl)-2-(((3-methylpyridin-2-yl)amino)methyl)-6,7-dihydropyrazolo[1,5-a]pyrazin-4(5H)-one;
5-(4-fluorophenyl)-2-(((4-methylpyridin-2-yl)amino)methyl)-6,7-dihydropyrazolo[1,5-a]pyrazin-4(5H)-one;
5-(4-fluorophenyl)-2-(((3-(trifluoromethyl)pyridin-2-yl)amino)methyl)-6,7-dihydropyrazolo[1,5-a]pyrazin-4(5H)-one;
2-(((6-chloropyridin-2-yl)amino)methyl)-5-(4-fluorophenyl)-6,7-dihydropyrazolo[1,5-a]pyrazin-4(5H)-one;
2-(((4-chloropyridin-2-yl)amino)methyl)-5-(4-fluorophenyl)-6,7-dihydropyrazolo[1,5-a]pyrazin-4(5H)-one;
2-(((3-chloropyridin-2-yl)amino)methyl)-5-(4-fluorophenyl)-6,7-dihydropyrazolo[1,5-a]pyrazin-4(5H)-one;
5-(4-fluorophenyl)-2-(((3-fluoropyridin-2-yl)amino)methyl)-6,7-dihydropyrazolo[1,5-a]pyrazin-4(5H)-one;
5-(4-fluorophenyl)-2-(((6-(trifluoromethyl)pyridin-2-yl)amino)methyl)-6,7-dihydropyrazolo[1,5-a]pyrazin-4(5H)-one;
5-(3,4-difluorophenyl)-2-(((4-methoxyphenyl)amino)methyl)-6,7-dihydropyrazolo[1,5-a]pyrazin-4(5H)-one;
5-(4-chlorophenyl)-2-(((4-methoxyphenyl)amino)methyl)-6,7-dihydropyrazolo[1,5-a]pyrazin-4(5H)-one;
2-(((4-(difluoromethoxy)-2-fluorophenyl)amino)methyl)-5-(5-methylthiazol-2-yl)-6,7-dihydropyrazolo[1,5-a]pyrazin-4(5H)-one;
2-(((4-(difluoromethoxy)-2-fluorophenyl)amino)methyl)-5-(6-fluoropyridin-2-yl)-6,7-dihydropyrazolo[1,5-a]pyrazin-4(5H)-one;
5-(4-chloropyridin-2-yl)-2-(((4-(difluoromethoxy)-2-fluorophenyl)amino)methyl)-6,7-dihydropyrazolo[1,5-a]pyrazin-4(5H)-one;
2-(((4-(difluoromethoxy)-2-fluorophenyl)amino)methyl)-5-(2-methylthiazol-4-yl)-6,7-dihydropyrazolo[1,5-a]pyrazin-4(5H)-one;
2-(((4-(difluoromethoxy)-2-fluorophenyl)amino)methyl)-5-(2,4-difluorophenyl)-6,7-dihydropyrazolo[1,5-a]pyrazin-4(5H)-one;
2-(((4-(difluoromethoxy)-2-fluorophenyl)amino)methyl)-5-(3-methoxyphenyl)-6,7-dihydropyrazolo[1,5-a]pyrazin-4(5H)-one;
2-(((4-(difluoromethoxy)-2-fluorophenyl)amino)methyl)-5-(3-fluoropyridin-2-yl)-6,7-dihydropyrazolo[1,5-a]pyrazin-4(5H)-one;
2-(((4-(difluoromethoxy)-2-fluorophenyl)amino)methyl)-5-(5-methylpyridin-2-yl)-6,7-dihydropyrazolo[1,5-a]pyrazin-4(5H)-one;
2-(((4-(difluoromethoxy)-2-fluorophenyl)amino)methyl)-5-(3-fluorophenyl)-6,7-dihydropyrazolo[1,5-a]pyrazin-4(5H)-one;
2-(((4-(difluoromethoxy)-2-fluorophenyl)amino)methyl)-5-(3,4-difluorophenyl)-6,7-dihydropyrazolo[1,5-a]pyrazin-4(5H)-one;
2-(((4-(difluoromethoxy)-2-fluorophenyl)amino)methyl)-5-(5-fluoropyridin-2-yl)-6,7-dihydropyrazolo[1,5-a]pyrazin-4(5H)-one;
2-(((4-(difluoromethoxy)-2-fluorophenyl)amino)methyl)-5-(3-fluoro-5-methoxyphenyl)-6,7-dihydropyrazolo[1,5-a]pyrazin-4(5H)-one;
5-(5-chloropyridin-2-yl)-2-(((4-(difluoromethoxy)-2-fluorophenyl)amino)methyl)-6,7-dihydropyrazolo[1,5-a]pyrazin-4(5H)-one;
5-(4-chloro-2-fluorophenyl)-2-(((4-(difluoromethoxy)-2-fluorophenyl)amino)methyl)-6,7-dihydropyrazolo[1,5-a]pyrazin-4(5H)-one;
5-(3-chlorophenyl)-2-(((4-(difluoromethoxy)-2-fluorophenyl)amino)methyl)-6,7-dihydropyrazolo[1,5-a]pyrazin-4(5H)-one;
2-(((4-(difluoromethoxy)-2-fluorophenyl)amino)methyl)-5-(pyridin-2-yl)-6,7-dihydropyrazolo[1,5-a]pyrazin-4(5H)-one;
2-(((4-(difluoromethoxy)-2-fluorophenyl)amino)methyl)-5-(3,5-difluorophenyl)-6,7-dihydropyrazolo[1,5-a]pyrazin-4(5H)-one; and
2-(((4-(difluoromethoxy)-2-fluorophenyl)amino)methyl)-5-(2-fluorophenyl)-6,7-dihydropyrazolo[1,5-a]pyrazin-4(5H)-one;
and pharmaceutically acceptable salts thereof.

In certain embodiments, $R^1$ is phenyl, optionally substituted with one to three substituents independently selected from halogen, cyano, alkyl, alkoxy, alkoxyalkyl, fluoroalkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; and $R^3$, $R^4$, $R^5$, and $R^6$ are hydrogen.

In certain embodiments, $R^1$ is pyridinyl, optionally substituted with one substituent selected from halogen and alkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; and $R^3$, $R^4$, $R^5$, and $R^6$ are hydrogen.

In certain embodiments, $R^1$ is thiazolyl, optionally substituted with one substituent selected from alkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; and $R^3$, $R^4$, $R^5$, and $R^6$ are hydrogen.

In a preferred embodiment, $R^2$ is selected from the group consisting of:

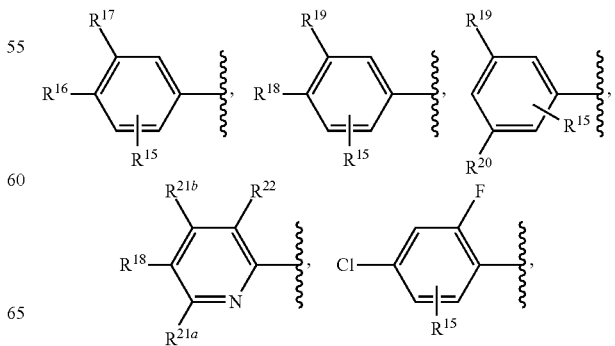

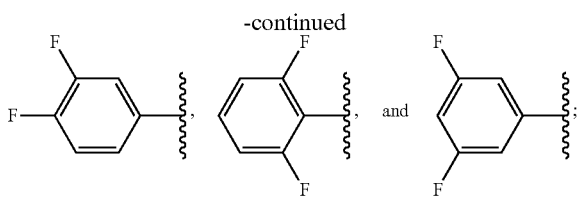

$R^{15}$ is selected from the group consisting of hydrogen and fluorine; $R^{16}$ is selected from the group consisting of cyano, methyl, ethyl, methoxy, difluoromethoxy, —$CR^{23}R^{24}OH$, —$CR^{23}R^{24}OCH_3$, and —$CR^{23}R^{24}CN$; $R^{17}$ is selected from the group consisting of hydrogen, fluorine, cyano, methyl, methoxy, and difluoromethoxy; $R^{18}$ is selected from the group consisting of hydrogen, fluorine, cyano, methyl, ethyl, methoxy, difluoromethoxy, —$CR^{23}R^{24}OH$, —$CR^{23}R^{24}OCH_3$, and —$CR^{23}R^{24}CN$; $R^{19}$ is selected from the group consisting of cyano, methyl, ethyl, methoxy, difluoromethoxy, —$CR^{23}R^{24}OH$, —$CR^{23}R^{24}OCH_3$, and —$CR^{23}R^{24}CN$; $R^{20}$ is selected from the group consisting of hydrogen, fluorine, chlorine, cyano, methyl, ethyl, methoxy, difluoromethoxy, —$CR^{23}R^{24}OH$, —$CR^{23}R^{24}OCH_3$, and —$CR^{23}R^{24}CN$; $R^{21a}$ and $R^{21b}$ are independently selected from the group consisting of hydrogen, fluorine, chlorine, cyano, methyl, methoxy, difluoromethoxy, —$CR^{23}R^{24}OH$, —$CR^{23}R^{24}OCH_3$, and —$CR^{23}R^{24}CN$; $R^{22}$ is selected from the group consisting of hydrogen, fluorine, and chlorine; $R^{23}$ and $R^{24}$ are independently selected from the group consisting of hydrogen, fluorine, and methyl; and $R^1$, $R^3$, $R^4$, $R^5$, and $R^6$ are as defined according to any of the previous embodiments; wherein $R^2$ is not unsubstituted pyridinyl, 3-methylphenyl, or 4-(difluoromethoxy)-3-fluorophenyl. Representative compounds include, but are not limited to:

5-(4-fluorophenyl)-2-((m-tolylamino)methyl)-6,7-dihydropyrazolo[1,5-a]pyrazin-4(5H)-one;
5-(4-fluorophenyl)-2-(((3-methoxyphenyl)amino)methyl)-6,7-dihydropyrazolo[1,5-a]pyrazin-4(5H)-one;
3-(((5-(4-fluorophenyl)-4-oxo-4,5,6,7-tetrahydropyrazolo[1,5-a]pyrazin-2-yl)methyl)amino)benzonitrile;
2-(((3-(difluoromethoxy)phenyl)amino)methyl)-5-(4-fluorophenyl)-6,7-dihydropyrazolo[1,5-a]pyrazin-4(5H)-one;
5-(4-fluorophenyl)-2-((p-tolylamino)methyl)-6,7-dihydropyrazolo[1,5-a]pyrazin-4(5H)-one;
5-(4-fluorophenyl)-2-(((4-methoxyphenyl)amino)methyl)-6,7-dihydropyrazolo[1,5-a]pyrazin-4(5H)-one;
4-(((5-(4-fluorophenyl)-4-oxo-4,5,6,7-tetrahydropyrazolo[1,5-a]pyrazin-2-yl)methyl)amino)benzonitrile;
2-(((4-(difluoromethoxy)phenyl)amino)methyl)-5-(4-fluorophenyl)-6,7-dihydropyrazolo[1,5-a]pyrazin-4(5H)-one;
2-(((4-ethylphenyl)amino)methyl)-5-(4-fluorophenyl)-6,7-dihydropyrazolo[1,5-a]pyrazin-4(5H)-one;
2-(4-(((5-(4-fluorophenyl)-4-oxo-4,5,6,7-tetrahydropyrazolo[1,5-a]pyrazin-2-yl)methyl)amino)phenyl)acetonitrile;
2-(((3,5-difluorophenyl)amino)methyl)-5-(4-fluorophenyl)-6,7-dihydropyrazolo[1,5-a]pyrazin-4(5H)-one;
2-(((3,4-difluorophenyl)amino)methyl)-5-(4-fluorophenyl)-6,7-dihydropyrazolo[1,5-a]pyrazin-4(5H)-one;
2-(((2,6-difluorophenyl)amino)methyl)-5-(4-fluorophenyl)-6,7-dihydropyrazolo[1,5-a]pyrazin-4(5H)-one;
2-(((4-chloro-2-fluorophenyl)amino)methyl)-5-(4-fluorophenyl)-6,7-dihydropyrazolo[1,5-a]pyrazin-4(5H)-one;
2-(((2-fluoro-4-methylphenyl)amino)methyl)-5-(4-fluorophenyl)-6,7-dihydropyrazolo[1,5-a]pyrazin-4(5H)-one;
2-(((4-fluoro-3-methylphenyl)amino)methyl)-5-(4-fluorophenyl)-6,7-dihydropyrazolo[1,5-a]pyrazin-4(5H)-one;
2-(((4-(difluoromethoxy)-2-fluorophenyl)amino)methyl)-5-(4-fluorophenyl)-6,7-dihydropyrazolo[1,5-a]pyrazin-4(5H)-one;
5-(4-fluorophenyl)-2-(((5-fluoropyridin-2-yl)amino)methyl)-6,7-dihydropyrazolo[1,5-a]pyrazin-4(5H)-one;
5-(4-fluorophenyl)-2-(((6-methylpyridin-2-yl)amino)methyl)-6,7-dihydropyrazolo[1,5-a]pyrazin-4(5H)-one;
5-(4-fluorophenyl)-2-(((5-methylpyridin-2-yl)amino)methyl)-6,7-dihydropyrazolo[1,5-a]pyrazin-4(5H)-one;
5-(4-fluorophenyl)-2-(((4-methylpyridin-2-yl)amino)methyl)-6,7-dihydropyrazolo[1,5-a]pyrazin-4(5H)-one;
2-(((6-chloropyridin-2-yl)amino)methyl)-5-(4-fluorophenyl)-6,7-dihydropyrazolo[1,5-a]pyrazin-4(5H)-one;
2-(((4-chloropyridin-2-yl)amino)methyl)-5-(4-fluorophenyl)-6,7-dihydropyrazolo[1,5-a]pyrazin-4(5H)-one;
2-(((3-chloropyridin-2-yl)amino)methyl)-5-(4-fluorophenyl)-6,7-dihydropyrazolo[1,5-a]pyrazin-4(5H)-one;
5-(4-fluorophenyl)-2-(((3-fluoropyridin-2-yl)amino)methyl)-6,7-dihydropyrazolo[1,5-a]pyrazin-4(5H)-one;
5-(3,4-difluorophenyl)-2-(((4-methoxyphenyl)amino)methyl)-6,7-dihydropyrazolo[1,5-a]pyrazin-4(5H)-one;
5-(4-chlorophenyl)-2-(((4-methoxyphenyl)amino)methyl)-6,7-dihydropyrazolo[1,5-a]pyrazin-4(5H)-one;
2-(((4-(difluoromethoxy)-2-fluorophenyl)amino)methyl)-5-(5-methylthiazol-2-yl)-6,7-dihydropyrazolo[1,5-a]pyrazin-4(5H)-one;
2-(((4-(difluoromethoxy)-2-fluorophenyl)amino)methyl)-5-(6-fluoropyridin-2-yl)-6,7-dihydropyrazolo[1,5-a]pyrazin-4(5H)-one;
5-(4-chloropyridin-2-yl)-2-(((4-(difluoromethoxy)-2-fluorophenyl)amino)methyl)-6,7-dihydropyrazolo[1,5-a]pyrazin-4(5H)-one;
2-(((4-(difluoromethoxy)-2-fluorophenyl)amino)methyl)-5-(2-methylthiazol-4-yl)-6,7-dihydropyrazolo[1,5-a]pyrazin-4(5H)-one;
2-(((4-(difluoromethoxy)-2-fluorophenyl)amino)methyl)-5-(2,4-difluorophenyl)-6,7-dihydropyrazolo[1,5-a]pyrazin-4(5H)-one;
2-(((4-(difluoromethoxy)-2-fluorophenyl)amino)methyl)-5-(3-methoxyphenyl)-6,7-dihydropyrazolo[1,5-a]pyrazin-4(5H)-one;
2-(((4-(difluoromethoxy)-2-fluorophenyl)amino)methyl)-5-(3-fluoropyridin-2-yl)-6,7-dihydropyrazolo[1,5-a]pyrazin-4(5H)-one;
2-(((4-(difluoromethoxy)-2-fluorophenyl)amino)methyl)-5-(5-methylpyridin-2-yl)-6,7-dihydropyrazolo[1,5-a]pyrazin-4(5H)-one;
2-(((4-(difluoromethoxy)-2-fluorophenyl)amino)methyl)-5-(3-fluoropyridin-2-yl)-6,7-dihydropyrazolo[1,5-a]pyrazin-4(5H)-one;
2-(((4-(difluoromethoxy)-2-fluorophenyl)amino)methyl)-5-(3,4-difluorophenyl)-6,7-dihydropyrazolo[1,5-a]pyrazin-4(5H)-one;
2-(((4-(difluoromethoxy)-2-fluorophenyl)amino)methyl)-5-(5-fluoropyridin-2-yl)-6,7-dihydropyrazolo[1,5-a]pyrazin-4(5H)-one;
2-(((4-(difluoromethoxy)-2-fluorophenyl)amino)methyl)-5-(3-fluoro-5-methoxyphenyl)-6,7-dihydropyrazolo[1,5-a]pyrazin-4(5H)-one;
5-(5-chloropyridin-2-yl)-2-(((4-(difluoromethoxy)-2-fluorophenyl)amino)methyl)-6,7-dihydropyrazolo[1,5-a]pyrazin-4(5H)-one;
5-(4-chloro-2-fluorophenyl)-2-(((4-(difluoromethoxy)-2-fluorophenyl)amino)methyl)-6,7-dihydropyrazolo[1,5-a]pyrazin-4(5H)-one;

5-(3-chlorophenyl)-2-(((4-(difluoromethoxy)-2-fluorophenyl)amino)methyl)-6,7-dihydropyrazolo[1,5-a]pyrazin-4(5H)-one;

2-(((4-(difluoromethoxy)-2-fluorophenyl)amino)methyl)-5-(pyridin-2-yl)-6,7-dihydropyrazolo[1,5-a]pyrazin-4(5H)-one;

2-(((4-(difluoromethoxy)-2-fluorophenyl)amino)methyl)-5-(3,5-difluorophenyl)-6,7-dihydropyrazolo[1,5-a]pyrazin-4(5H)-one; and 2-(((4-(difluoromethoxy)-2-fluorophenyl)amino)methyl)-5-(2-fluorophenyl)-6,7-dihydropyrazolo[1,5-a]pyrazin-4(5H)-one;

and pharmaceutically acceptable salts thereof.

In certain embodiments, $R^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$, $R^4$, and $R^5$ are hydrogen; and $R^6$ is selected from the group consisting of $C_1$-$C_3$ alkyl and $C_1$-$C_3$ fluoroalkyl. Representative compounds include, but are not limited to:

5-(4-fluorophenyl)-2-(1-(phenylamino)ethyl)-6,7-dihydropyrazolo[1,5-a]pyrazin-4(5H)-one;

5-(4-fluorophenyl)-2-(1-((4-fluorophenyl)amino)ethyl)-6,7-dihydropyrazolo[1,5-a]pyrazin-4(5H)-one;

2-(1-((4-chlorophenyl)amino)ethyl)-5-(4-fluorophenyl)-6,7-dihydropyrazolo[1,5-a]pyrazin-4(5H)-one; and 5-(4-fluorophenyl)-2-(1-((4-methoxyphenyl)amino)ethyl)-6,7-dihydropyrazolo[1,5-a]pyrazin-4(5H)-one;

and pharmaceutically acceptable salts thereof.

In certain embodiments, $R^1$ is phenyl, optionally substituted with one to three substituents independently selected from halogen, cyano, alkyl, alkoxy, alkoxyalkyl, fluoroalkoxy; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$, $R^4$, and $R^5$ are hydrogen; and $R^6$ is selected from the group consisting of $C_1$-$C_3$ alkyl and $C_1$-$C_3$ fluoroalkyl.

In certain embodiments, $R^1$ is pyridinyl, optionally substituted with one substituent selected from halogen and alkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$, $R^4$, and $R^5$ are hydrogen; and $R^6$ is selected from the group consisting of $C_1$-$C_3$ alkyl and $C_1$-$C_3$ fluoroalkyl.

In certain embodiments, $R^1$ is thiazolyl, optionally substituted with one substituent selected from alkyl; $R^2$ is selected from the group consisting of phenyl and pyridinyl, each optionally substituted with one to five substituents independently selected from halogen, cyano, alkyl, fluoroalkyl, alkoxy, fluoroalkoxy, hydroxyalkyl, hydroxyfluoroalkyl, alkoxyalkyl, alkoxyfluoroalkyl, cyanoalkyl, and cyanofluoroalkyl, wherein 2 of the substituents on adjacent carbons can together form a 5 or 6 membered ring; $R^3$, $R^4$, and $R^5$ are hydrogen; and $R^6$ is selected from the group consisting of $C_1$-$C_3$ alkyl and $C_1$-$C_3$ fluoroalkyl.

In a preferred embodiment, $R^1$ is aryl, optionally substituted with halogen; $R^2$ is phenyl, optionally substituted with halogen and alkoxy; $R^3$ is selected from the group consisting of hydrogen, $C_1$-$C_3$ alkyl, and $C_1$-$C_3$ fluoroalkyl; $R^4$ and $R^5$ are each independently selected from the group consisting of hydrogen and $C_1$-$C_3$ alkyl; and $R^6$ is $C_1$-$C_3$ alkyl. Representative compounds include, but are not limited to:

5-(4-fluorophenyl)-2-(1-(phenylamino)ethyl)-6,7-dihydropyrazolo[1,5-a]pyrazin-4(5H)-one;

5-(4-fluorophenyl)-2-(1-((4-fluorophenyl)amino)ethyl)-6,7-dihydropyrazolo[1,5-a]pyrazin-4(5H)-one;

2-(1-((4-chlorophenyl)amino)ethyl)-5-(4-fluorophenyl)-6,7-dihydropyrazolo[1,5-a]pyrazin-4(5H)-one; and 5-(4-fluorophenyl)-2-(1-((4-methoxyphenyl)amino)ethyl)-6,7-dihydropyrazolo[1,5-a]pyrazin-4(5H)-one;

and pharmaceutically acceptable salts thereof.

Compound names are assigned by using Struct=Name naming algorithm as part of CHEMDRAW® ULTRA v. 12.0.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present invention also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Allosteric Modulation of mGlu$_3$

The disclosed compounds may act or function as non-competitive antagonists, allosteric inhibitors, allosteric antagonists, or negative allosteric modulators (NAM) of mGlu$_3$. The compounds may be procognitive and neuroprotective even in the presence of mGlu$_3$ dysfunction.

Compounds of formula (I) can inhibit mGlu$_3$ with an IC$_{50}$ ranging from about 100 nM to about 30 The compounds may have an IC$_{50}$ of about 30 μM, about 29 μM, about 28 μM, about 27 μM, about 26 μM, about 25 μM, about 24 μM, about 23 μM, about 22 μM, about 21 μM, about 20 μM, about 19 μM, about 18 μM, about 17 μM, about 16 μM, about 15 μM, about 14 μM, about 13 μM, about 12 μM, about 11 μM, about 10 μM, about 9 μM, about 8 μM, about 7 μM, about 6 μM, about 5 μM, about 4 μM, about 3 μM, about 2 μM, about 1 μM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, or about 1 nM. Compounds of formula (I) can inhibit mGlu$_3$ with an IC50 of less than 30 μM, less than 29 μM, less than 28 μM, less than 27 μM, less than 26 μM, less than 25 μM, less than 24 μM, less than 23 μM, less than 22 μM, less than 21 μM, less than 20 μM, less than 19 μM, less than 18 μM, less than 17 μM, less than 16 μM, less than 15 μM, less than 14 μM, less than 13 μM, less than 12 μM, less than 11 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, or less than 1 nM.

Compounds of formula (I) may be selective modulators of mGlu$_3$ over mGlu$_5$. The compounds may have a ratio of mGlu$_3$ IC$_{50}$ to mGlu5 EC$_{50}$ of at least 100, at least 95, at least 90, at least 85, at least 80, at least 75, at least 70, at least 64, at least 60, at least 55, at least 50, at least 45, at least 40, at least 35, at least 33, at least 31, at least 30, at least 29, at least 28, at least 27, at least 26, at least 25, at least 24, at least 23, at least 22, at least 21, at least 20, at least 19, at least 18, at least 17, at least 16, at least 15, at least 14, at least 13, at least 12, at least 11, at least 10, at least 9, at least 8, at least 7, at least 6, at least 5, at least 4, at least 3, or at least 2. Compounds of formula (I) may have a ratio of mGlu$_3$ IC$_{50}$ to mGlu5 EC$_{50}$ of about 100, about 95, about 90, about 85, about 80, about 75, about 70, about 64, about 60, about 55, about 50, about 45, about 40, about 35, about 33, about 31, about 30, about 29, about 28, about 27, about 26, about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, or about 2.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

B. General Synthesis

Compounds of formula (I) may be prepared by synthetic processes or by metabolic processes. Preparation of the compounds by metabolic processes includes those occurring in the human or animal body (in vivo) or processes occurring in vitro.

Compounds of formula (I), wherein the groups $R^1$, $R^2$, $R^3$, $R^4$, $R^5$, and $R^6$ have the meanings as set forth in the Summary of the Invention section unless otherwise noted, can be synthesized as shown in Schemes 1-10.

Abbreviations which have been used in the descriptions of the Schemes that follow are: D$^t$BAD for di-tert-butylazodicarboxylate; BOC for tert-butoxycarbonyl; BOC$_2$O for di-tert-butylcarbonate; DMF for dimethylformamide; PMB for para-methoxybenzyl; Ms for methanesulfonyl; TEA for triethylamine; TFAA for trifluoroacetic anhydride; CAN for ceric ammonium nitrate; NMP for N-methyl-2-pyrrolidone; KOAc for potassium acetate; and HOAc for acetic acid.

Scheme 1. Synthesis of intermediate v

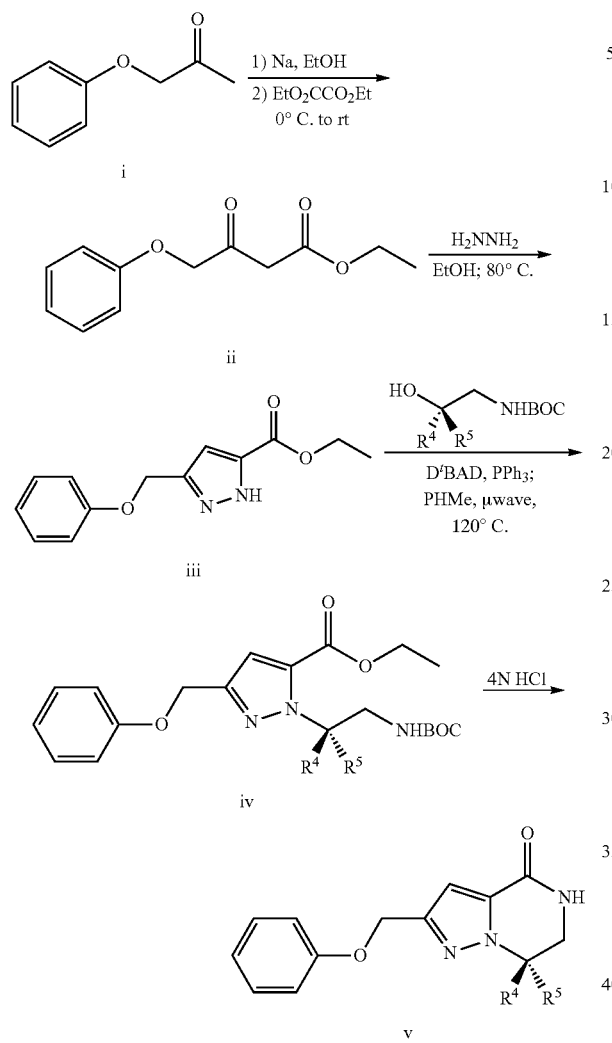

Scheme 2. Synthesis of intermediate vii

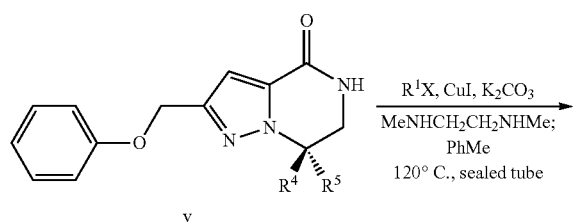

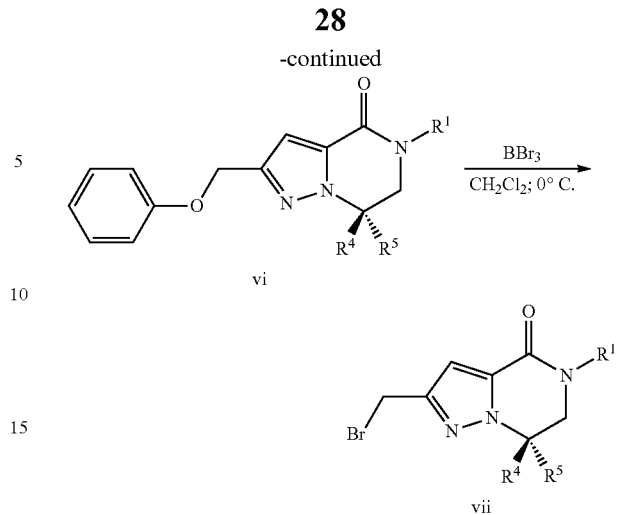

As shown in Scheme 1, intermediate v, wherein $R^4$ and $R^5$ are as defined in the Summary of the Invention, can be prepared from phenoxy-2-propanone, i. Treatment of i with sodium in ethanol, followed by addition of diethyl oxalate, can result in formation of β-ketoester ii. β-ketoester ii can be treated with hydrazine to provide the disubstituted pyrazole iii. Pyrazole iii may then be coupled with a N—BOC-protected aminoethanol via Mitsunobu conditions to yield compound iv. Under acidic conditions, compound iv can be converted to intermediate v.

Scheme 2 illustrates the conversion of intermediate v to intermediate vii. Intermediate v can be coupled to an aryl or heteroaryl group ($R^1$) by a copper-mediated coupling reaction to yield compound vi. Conversion of the benzyloxy group of compound vi to the corresponding bromide can be achieved by treatment with boron tribromide, yielding intermediate vii.

Scheme 3. Synthesis of intermediate ix

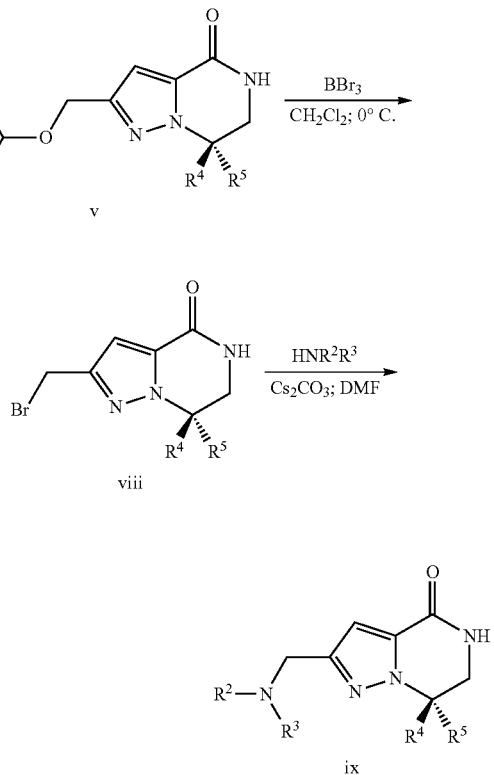

Intermediate v can also be converted to intermediate ix by the two-step sequence shown in Scheme 3. Bromination of intermediate v to give compound viii can be followed by addition of an amine, wherein $R^2$ and $R^3$ are as defined in the Summary of the Invention, to provide intermediate ix.

Scheme 4. Synthesis of intermediate xi

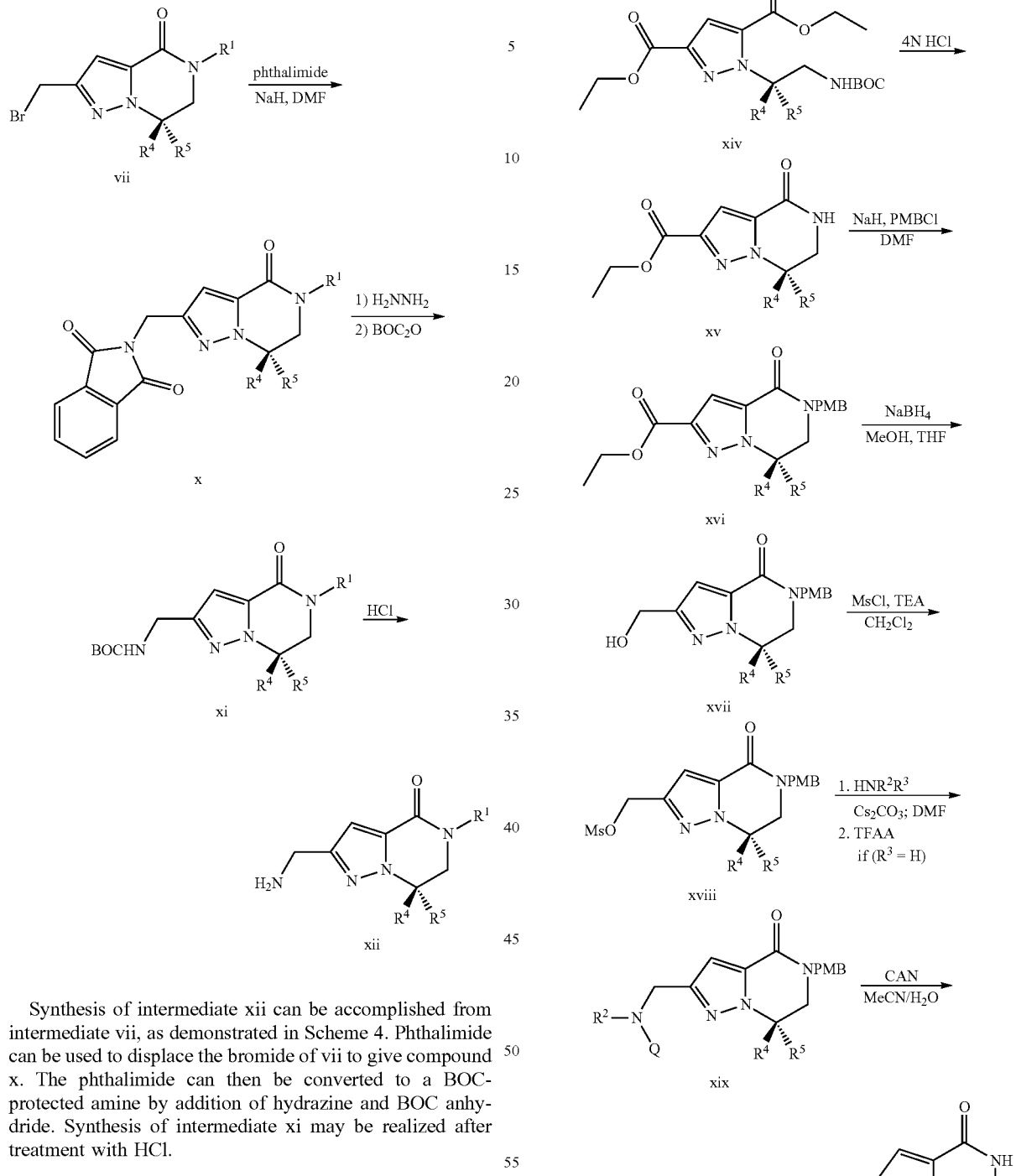

Synthesis of intermediate xii can be accomplished from intermediate vii, as demonstrated in Scheme 4. Phthalimide can be used to displace the bromide of vii to give compound x. The phthalimide can then be converted to a BOC-protected amine by addition of hydrazine and BOC anhydride. Synthesis of intermediate xi may be realized after treatment with HCl.

Scheme 5. Synthesis of intermediate xx

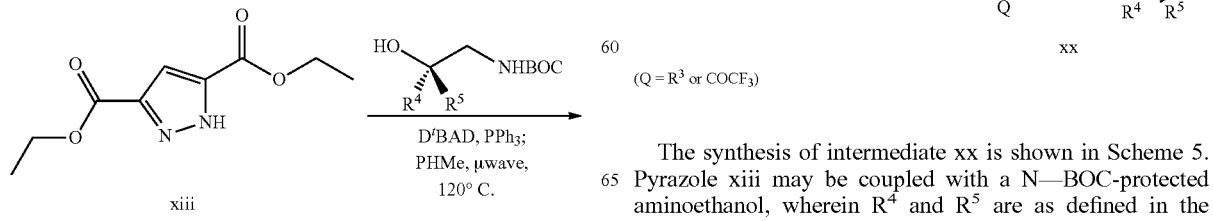

The synthesis of intermediate xx is shown in Scheme 5. Pyrazole xiii may be coupled with a N—BOC-protected aminoethanol, wherein $R^4$ and $R^5$ are as defined in the Summary of the Invention, via Mitsunobu conditions to yield compound xiv. Cyclization under acidic conditions can provide compound xv. The resulting amide nitrogen can be protected with a p-methoxybenzyl group to give compound xvi. Reduction of the ethyl ester in xvi can be followed by conversion of the resulting hydroxyl group to the mesylate in compound xviii. Displacement of the mesylate with an amine, wherein $R^2$ and $R^3$ are as defined in the Summary of the Invention, can provide compound xix. If $R^3$ is hydrogen, then the nitrogen can further be protected as the TFA amide. The p-methoxybenzyl group can be removed under reducing conditions to supply intermediate xx.

defined in the Summary of the Invention. When Q is the TFA amide, then it can be cleaved by subsequent treatment with base to provide the compound of formula (I).

Scheme 6. Synthesis of the compound of formula (I)

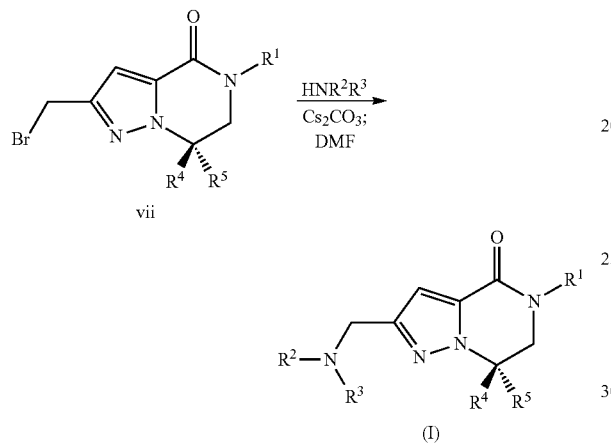

As illustrated in Scheme 6, the compound of formula (I) can be constructed from intermediate vii. The synthesis of compounds of formula (I) can be achieved by the displacement of the bromide in intermediate vii with an amine, wherein $R^2$ and $R^3$ are as defined in the Summary of the Invention, to give compounds of formula (I).

Scheme 7. Synthesis of the compound of formula (I)

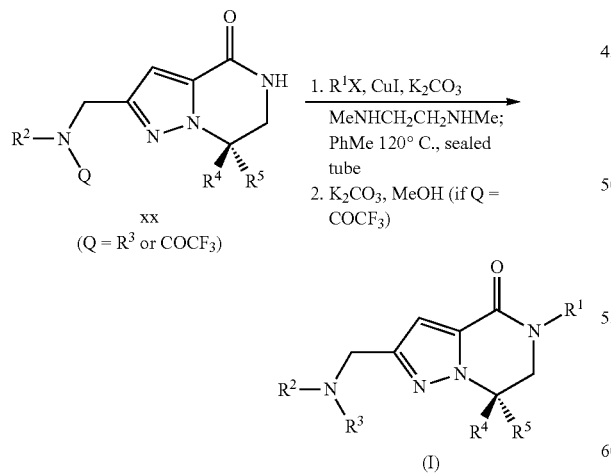

Shown in Scheme 7 is an alternative synthesis of the compound of formula (I) from intermediate xx. When Q is an alkyl group, the synthesis of the compound of formula (I) can be achieved by a copper-mediated coupling reaction with the aryl or heteroaryl group represented by $R^1$ and Scheme 8. Synthesis of the compound of formula (I)

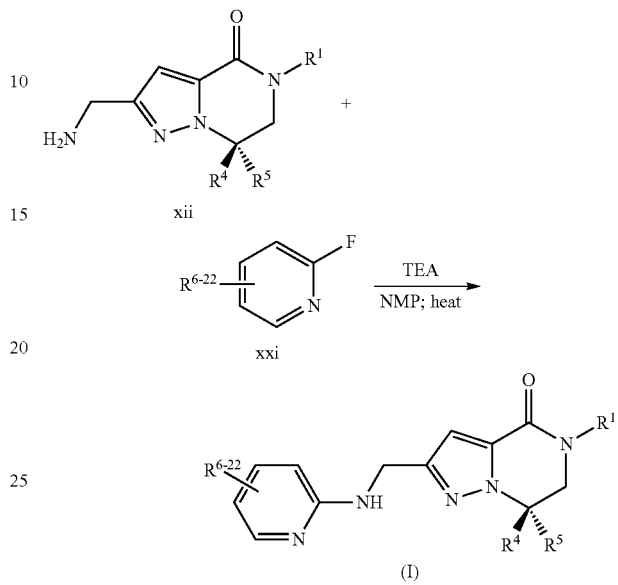

An additional method for the synthesis of the compound of formula (I) is shown in Scheme 8. For compounds in which $R^2$ is a 2-pyridinyl group, intermediate xii can be coupled to substituted 2-fluoropyridines xxi, that have substitution as defined in the Summary of the Invention, and yields the compound of formula (I), wherein $R^2$ is a 2-pyridinyl group.

Scheme 9. Alternative synthesis of the compound of formula (I)

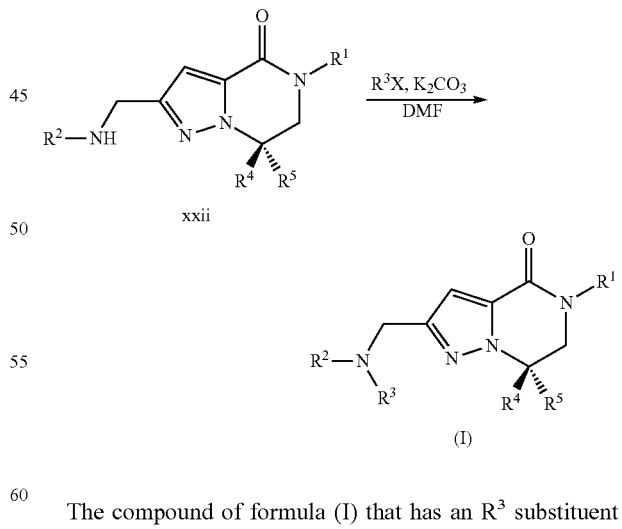

The compound of formula (I) that has an $R^3$ substituent other than hydrogen, can also be prepared by the route shown in Scheme 9. Compound xxii, wherein $R^1$, $R^2$, $R^4$, and $R^5$ are as defined in the Summary of the Invention, which can be prepared by the disclosed methods, can be alkylated under basic conditions with an alkyl or fluoroalkyl halide to give the compound of formula (I).

Scheme 10. Synthesis of the compound of formula (I)

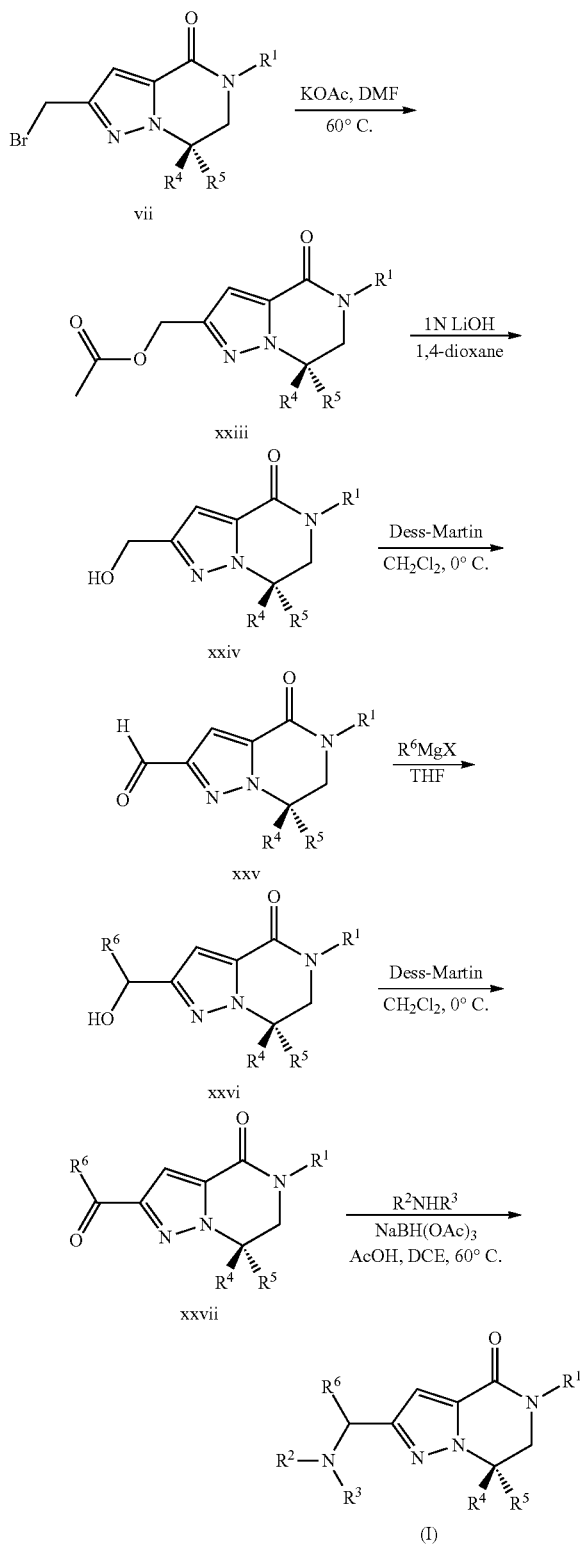

Scheme 10 depicts a synthetic route that may be implemented for the synthesis of the compound of formula (I) that has an alkyl or fluoroalkyl substituent as $R^6$. The bromide of intermediate vii can be converted to the acetate of compound xxiii. Subsequent saponification of the acetate can reveal the primary alcohol of compound xxiv, which can be oxidized to the corresponding aldehyde of compound xxv. Addition of an appropriate Grignard reagent can provide the secondary alcohol of compound xxvi. Oxidation with Dess-Martin periodinane can yield the ketone of compound xxvii, which can subsequently be converted to the compound of formula (I) by way of reductive amination.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4th ed.), John Wiley & Sons, NY (2006), which is incorporated herein by reference in its entirety.

Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. PHARMACEUTICAL COMPOSITIONS

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. METHODS OF TREATMENT

The disclosed compounds and compositions may be used in methods for treatment of $mGlu_3$ related medical disorders and/or diseases. The methods of treatment may comprise administering to a subject in need of such treatment a composition comprising a therapeutically effective amount of the compound of formula (I).

The compositions can be administered to a subject in need thereof to modulate $mGlu_3$, for a variety of diverse biological processes. The present disclosure is directed to methods for administering the composition to inhibit $mGlu_3$, a GPCR that plays a role in synaptic plasticity, which directly effects cognitive function and memory, for example.

The compositions may be useful for treating and preventing certain diseases and disorders in humans and animals related to $mGlu_3$ dysfunction. Treatment or prevention of such diseases and disorders can be effected by selectively modulating $mGlu_3$ in a subject, by administering a compound or composition of the invention, either alone or in combination with another active agent as part of a therapeutic regimen to a subject in need thereof a. Depression Campo, B. et al. *J. Neurogenetics* 2011, 25, 152-166, demonstrated a group II selective negative allosteric modulator (RO4491533) to be effective in several in vitro biochemical assays and in vivo models of depression. RO4491533 was shown to engage the central $mGlu_2$ and $mGlu_3$ receptors as the compound reversed the hypolocomotor effect of an $mGlu_{2/3}$ orthosteric agonist (LY379268) in a target-specific manner. The known group II orthosteric $mGlu_{2/3}$ antagonist LY341495 achieved the same result. RO4491533 and LY341495 dose-dependently reduced immobility time of C57Bl6/J mice in the forced swim test. RO4491533 and LY341495 were also active in the tail suspension test in a line of Helpless (H) mice, a putative genetic model of depression. Campo and coworker's data suggest that $mGlu_3$ receptors are viable targets for treating depression with $mGlu_3$ modulators.

b. Cognitive Disorders

Woltering et al. *Bioorg. Med. Chem. Lett.* 2010, 20, 6969-74, demonstrated that a negative allosteric modulator of $mGlu_{2/3}$ reversed $mGlu_{2/3}$ agonist or scopolamine-induced working memory deficits in the delayed match to position (DMTP) task in rodents, a measure of working memory. Additionally, Woltering demonstrated a synergistic reversal of scopolamine-induced deficits in DMTP when low doses of a negative allosteric modulator of $mGlu_{2/3}$ were combined with a threshold dose of the acetylcholinesterase inhibitor donezepil. Given the efficacy of donepezil and other acetylcholinesterase inhibitors in the treatment of the cognitive impairments in Alzheimer's disease, negative allosteric modulators of $mGlu_3$ may have efficacy as cognitive enhancers.

c. Schizophrenia

Numerous studies have implicated glutamate neurotransmission, specifically aberrant N-methyl-D-aspartate receptor (NMDA) receptor function, as a key element in the pathophysiology of the schizophrenia (Kim J. et al. Neurosci. Lett. 1980, 20, 379-382.; Javitt, D. C; Zukin, S. R. *Am. J. Psychiatry* 1991, 148, 1301-1308.; Harrison, P. J.; Owen, M. J. *Lancet* 2003, 361, 417-419). According to this glutamate hypothesis of schizophrenia, a drug that can correct or modulate dysfunctional glutamatergic neurotransmission may be an effective therapeutic agent for schizophrenia.

The ability of $mGlu_3$ modulators to treat schizophrenia is demonstrated by Patil, S. et al. *Nature Medicine* 2007, 13, 1102-1107. Patil and coworkers report that LY404039 (an $mGlu_{2/3}$ modulator) was evaluated in schizophrenic patients in a randomized, three-armed, double-blind, placebo-controlled study. Treated patients showed statistically significant improvements in both positive and negative symptoms of schizophrenia compared to placebo (P<0.001 at week 4). These results suggest that modulators of $mGlu_3$ can have antipsychotic properties and can be used for the treatment of schizophrenia.

d. Alzheimer's Disease

Caraci, F. et al *Mol. Pharmacol.* 2011, 79, 618-626, showed that a positive allosteric modulator of $mGlu_2$ (LY566332) amplified Aβ-induced neurodegeneration, but this effect was prevented by the $mGlu_{2/3}$ receptor antagonist, LY341495. An additional $mGlu_3$ modulator, LY379268, showed neuroprotective activity. Further studies indicated that protection against Aβ neurotoxicity was mediated entirely by glial mGlu3 receptors. Overall, Caraci suggests and demonstrates that modulators of $mGlu_3$ may be helpful in treating Alzheimer's disease and/or symptoms of Alzheimer's disease.

Additional studies by Durand et al. (*Neuropharmacology* 2014, 180-189) suggest that the pathophysiology of Alzheimer's disease is influenced by the $mGlu_3$ receptor. They demonstrated that α-secretase cleavage generates a soluble and neuroprotective fragment (sAPPα) which precludes the production of Aβ peptides. The $mGlu_3$ modulator, LY379268, incremented sAPPα release from cultured astrocytes by inducing α-secretase expression. As such, $mGlu_3$ modulation may be an effective treatment for Alzheimer's disease.

e. Cancer

Inhibition of $mGlu_3$ can lead to treatment and reduction of cancer or tumor growth, and/or reduce metastasis of cancerous or tumor cells. Accordingly, the disclosed compositions can be used in methods that treat and/or prevent cancer or tumors in a subject administered the composition. The method can treat cancer or tumor based growth and can be any type of cancer such as, but not limited to, glioma, melanoma, blood cancers (e.g., leukemia, lymphoma, myeloma, B cell acute lymphoblastic leukemia, hepatocellular carcinoma, B cell chronic lymphocytic lymphoma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer, multiple myeloma, astrocytoma, and stomach cancer.

In some embodiments, the administered composition to a subject in need thereof can mediate reduction, clearance or prevention of additional growth of tumor cells by inhibiting $mGlu_3$, thereby reducing growth/proliferation of tumor cells, but does not have an effect on normal cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

Zhou et al. *Cell Biol. Int.* 2014, 38, 426-434, characterized, using both in vivo and in vitro methods, the effects of an $mGlu_3$ antagonist (LY341495) on the proliferation and differentiation of glioma stem cells (GSC). In vitro studies showed that the proliferation rates and proportion of cells in S phase within the LY341495 treated group decreased in a time-dependent manner. The growth rate and volume of tumors injected into nude mice was reduced in LY341495 treated mice compared with controls. Thus pharmacological blockade of $mGlu_3$ receptor signaling pathway significantly inhibits the growth and proliferation of GSCs both in vitro and in vivo while promoting differentiation to astrocytes. These results further implicate $mGlu_3$ in the biology of glioma and distinguish it as a cancer target.

f. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

g. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I. The above combinations include combinations of a compound of the present invention not only with one other active compound, but also with two or more other active compounds. For example, the compound of Formula I can be combined with a variety of antidepressants, Alzheimer's disease medications, anxiolytics, anti-cancer drugs and chemotherapeutics.

The compound of Formula I can be combined with the following antidepressants, but not limited to: Selective serotonin reuptake inhibitors (SSRIs) such as citalopram, dapoxetine, escitalopram, fluoxetine, fluvoxamine, indalpine, paroxetine, sertraline, and zimelidine; Serotonin-norepinephrine reuptake inhibitors (SNRIs) such as venlafaxine, desvenlafaxine, duloxetine, milnacipran, levomilnacipran, and sibutramine; Noradrenergic and specific serotonergic antidepressants (NaSSAs) or tetracyclic antidepressants (TeCAs) such as aptazapine, esmirtazapine, mianserin, mirtazapine, and setiptiline; Serotonin antagonist and reuptake inhibitors (SARIs) such as etoperidone, lorpiprazole, mepiprazole, nefazodone, trazodone, vilazodone, and niaprazine; Norepinephrine-dopamine reuptake inhibitors (NDRIs) such as armodafinil, bupropion, desoxypipradrol, dexmethylphenidate, methylphenidate, modafinil, prolintane, and tametraline; Serotonin-norepinephrine-dopamine reuptake inhibitors (SNDRIs) such as nefopam, amitifadine, tesofensine, and tedatioxetine; Tricyclic antidepressants (TCAs) such as clomipramine, desipramine, imipramine, dibenzepin, lofepramine, nortriptyline, protriptyline, amitriptyline, amitriptylinoxide, amoxapine, butriptyline, demexiptiline, dimetacrine, dosulepin, doxepin, imipraminoxide, melitracen, metapramine, nitroxazepine, noxiptiline, pipofezine, propizepine, quinupramine, amineptine, iprindole, opipramol, tianeptine, and trimipramine; and Negative allosteric modulators of metabotropic glutamate receptor 5 (mGlu$_5$) such as mavoglurant, basimglurant, dipraglurant, STX107, and N-(5-fluoropyridin-2-yl)-6-methyl-4-(pyrimidin-5-yloxy)picolinamide.

The compound of Formula I can be combined with the following Alzheimer's disease medications, but not limited to: Acetylcholinesterase inhibitors such as tacrine, rivastigmine, galantamine, donepezil, edrophonium, physostigmine, pyridostigmine, ambenonium, rivastigmine, ladostigil, and ungeremine; and NMDA receptor antagonists such as memantine, amantadine, delucemine, and ketamine.

The compound of Formula I can be combined with the following anxiolytics, but not limited to: buspirone, tandosprione, gepirone, adaptol, afobazole, hyroxyzine, validol, melatonin, and benzodiazepines such as alprazolam, chlordiazepoxide, clonazepam, diazepam, etizolam, lorazepam, oxazepam, and tofisopam.

The compound of Formula I can be combined with the following chemotherapeutics or anti-cancer drugs, but not limited to: DNA alkylating agents such as temozolomide, cisplatin, carboplatin, nedaplatin, oxaliplatin, satraplatin, triplatin tetranitrate, procarbazine, altretamine, dacarbazine, and mitozolomide; and kinase inhibitors such as bevacizumab, enzastaurin, gefitinib, erlotinib, temsirolimus, everolimus, cilengitide, lapatinib, sunitinib, sorafenib, axitinib, pazopanib, vemurafenib, dabrafenib, and alisertib.

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

6. EXAMPLES

Examples 1-6 below give representative experimental procedures for the syntheses of intermediates useful for the synthesis of compounds of formula (I). Examples 7-11 give representative experimental procedures for completion of syntheses of compounds of formula (I). Example 12 reports the biological activity of compounds of formula (I).

All NMR spectra were recorded on a 400 MHz AMX Bruker NMR spectrometer. $^1$H chemical shifts are reported in δ values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostatted column compartment, C18 column, diode-array detector (DAD) and an Agilent 6150 MSD with the following parameters. The gradient conditions were 5% to 95% acetonitrile with the aqueous phase 0.1% TFA in water over 1.4 minutes. Samples were separated on a Waters Acquity UPLC BEH C18 column (1.7 μm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

Example 1. (R)-2-(bromomethyl)-5-(4-fluorophenyl)-7-methyl-6,7-dihydropyrazolo[1,5-c]pyrazin-4(5H)-one (G)

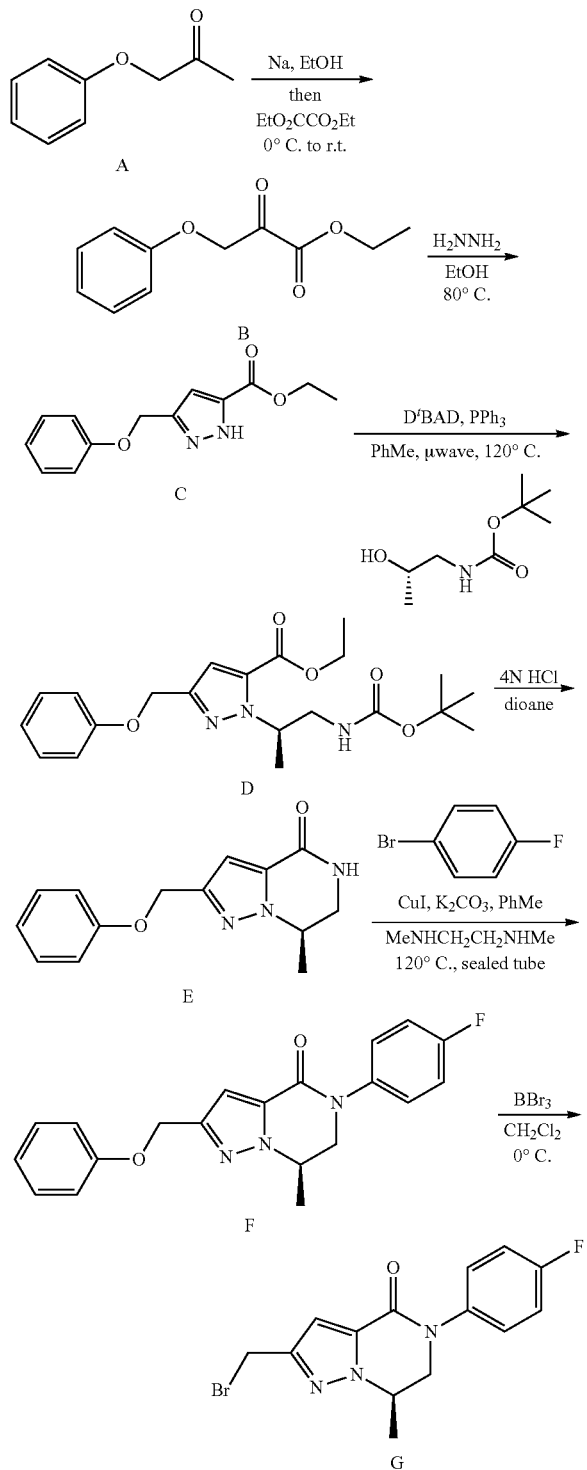

Ethyl 2-oxo-3-phenoxypropanoate (B)

To a flame-dried round bottom flask was added ethanol (121 mL) which was then cooled to 0° C. To this was added portion-wise sodium (1.83 g, 79.9 mmol, 1 eq.). The mixture was gradually warmed to room temperature and stirred until the sodium was completely consumed. The reaction was cooled back down to 0° C. and phenoxy acetone (10 mL, 72.6 mmol, 1 eq.) was added drop-wise. Reaction progress was monitored by LCMS and was complete within 1 hour. The crude reaction mixture was concentrated in vacuo to remove the ethanol and the crude residue was taken back up in DCM (100 mL). The solution was washed once with 1M HCl. The organic layer was washed once with brine, dried over $Na_2SO_4$ and concentrated in vacuo. The residue was purified via flash column chromatography hexanes/EtOAc, yielding the title compound as an impure mixture (4.5 g, ~18 mmol). This mixture was carried on without further purification. ES-MS $[M+1]^+$: 251.1.

Ethyl 3-(phenoxymethyl)-1H-pyrazole-5-carboxylate (C)

To a round bottom flask equipped with a reflux condenser was added impure B (4.5 g, ~18 mmol, 1 eq.) in ethanol. To this solution was added hydrazine hydrate (0.873 mL, 18 mmol, 1 eq.) and the reaction was heated to 80° C. overnight after which time the reaction was deemed complete by LCMS. The solvent was removed in vacuo and purified using flash column chromatography (hexanes/EtOAc), yielding the title compound as a pale yellow solid (2.27 g, 51% yield). $^1$H NMR (400 MHz, $CDCl_3$) δ 8.51 (bs, 1H), 7.32-7.29 (m, 2H), 7.00-6.96 (m, 2H), 6.92 (s, 1H), 5.17 (s, 2H), 4.38 (q, J=7.12 Hz, 2H), 1.39 (t, J=7.12 Hz, 3H). ES-MS $[M+1]^+$: 247.1.

Ethyl (R)-1-(1-((tert-butoxycarbonyl)amino)propan-2-yl)-3-(phenoxymethyl)-1H-pyrazole-5-carboxylate (D)

Split evenly among two microwave vials was combined C (1.13 g, 4.59 mmol, 1 eq.), tert-butyl (S)-(2-hydroxypropyl)carbamate (1.6 g, 9.13 mmol, 2 eq.), triphenyl phosphine (2.17 g, 8.26 mmol, 1.8 eq.) and THF (28 mL). To this was added di-tert-butyl azodicarboxylate (1.9 g, 8.26 mmol, 1.8 eq.). The mixture was heated under microwave irradiation at 120° C. for 20 minutes. The solvent was removed in vacuo, and the residue was purified using flash column chromatography (hexanes/EtOAc), yielding the title compound as a white solid (1.85 g, 99% yield) $^1$H NMR (400 MHz, MeOD) δ 7.30 (dd, J=8.7, 7.4 Hz, 2H), 7.01 (dd, J=8.7, 1 Hz, 2H), 6.96 (t, J=7.32 Hz, 1H), 6.91 (s, 1H), 5.56 (q, J=6.67 Hz, 1H), 5.51 (s, 1H), 4.34 (q, J=9.5 Hz, 2H), 3.44-3.43 (m, 2H), 1.48-1.36 (m, 15H). ES-MS $[M+1]^+$: 404.2.

(R)-7-Methyl-2-(phenoxymethyl)-6,7-dihydropyrazolo[1,5-a]pyrazin-4(5H)-one (E)

Compound D (1.85 g, 4.58 mmol, 1 eq.) was treated with a solution of 4N HCl in dioxane (20 mL). Boc deprotection was monitored by LCMS. Once deprotection was complete, the reaction mixture was carefully basified with saturated $NaHCO_3$ (verified by pH paper) and was allowed to stir at room temperature overnight. The mixture was diluted with DCM, and the aqueous layer was extracted with DCM (3×). The combined organic layers were washed with brine, dried over $Na_2SO_4$ and concentrated in vacuo. Purified using flash column chromatography (hexanes/EtOAc) provided the title compound as a white solid (980 mg, 83% yield). $^1$H NMR (400 MHz, $CDCl_3$) δ 7.44 (bs, 1H), 7.30-7.26 (m, 2H), 7.00-6.94 (m, 4H), 4.55-4.50 (m, 1H), 3.81-3.76 (m, 1H), 3.49-3.44 (m, 1H), 1.60 (d, J=6.5 Hz, 3H). ES-MS [M+1]⁺: 258.1.

(R)-5-(4-fluorophenyl)-7-methyl-2-(phenoxymethyl)-6,7-dihydropyrazolo[1,5-a]pyrazin-4(5H)-one (F)

To a round bottom flask equipped with a condenser was added E (980 mg, 3.81 mmol, 1 eq.), toluene (38 mL), 4-fluoro bromobenzene (2.25 mL, 20.9 mmol, 5.5 eq.), N,N'-dimethylethylenediamine (0.858 mL, 7.81 mmol, 2.05 eq.), and potassium carbonate (1.08 g, 7.81 mmol, 2.05 eq.). Lastly, copper iodide (1.49 g, 7.81 mmol, 2.05 eq.) was added. The reaction was refluxed overnight after which time the reaction was deemed complete by LCMS. The reaction was cooled to room temperature and filtered through celite, washing with EtOAc. The filtrate was concentrated in vacuo, and the residue was purified using flash column chromatography (hexanes/EtOAc), yielding the title compound as a white solid (1.33 g, 89% yield). ¹H NMR (400 MHz, CDCl₃) δ 7.33-7.28 (m, 4H), 7.15-7.11 (m, 2H), 7.04-6.96 (m, 4H), 5.13 (s, 2H), 4.72-4.67 (m, 1H), 4.16 (dd, J=12.8, 4.2 Hz, 1H), 3.88 (dd, J=12.8, 7.3 Hz, 1H), 1.69 (d, J=6.5 Hz, 3H). ES-MS [M+1]⁺: 352.1.

(R)-2-(bromomethyl)-5-(4-fluorophenyl)-7-methyl-6,7-dihydropyrazolo[1,5-a]pyrazin-4(5H)-one (G)

To a solution of F (619 mg, 1.76 mmol, 1.0 eq.) in DCM (8.8 mL) at 0° C. was added a solution of 1M BBr₃ in DCM (4.4 mL, 4.4 mmol, 2.5 eq.). The reaction was then warmed to room temperature and stirred for 2 h. The reaction was diluted with DCM (30 mL). The organic layers were washed sequentially with 1M HCl (40 mL), saturated aqueous NaHCO₃ (40 mL), 1M aqueous NaOH (40 mL), and brine (40 mL). The organic layer was dried over Na₂SO₄ and concentrated in vacuo providing the title compound as a light brown solid (584 mg, 98% yield) which was used without further purification. ¹H NMR (400 MHz, CDCl₃) δ 7.33-7.29 (m, 2H), 7.15-7.11 (m, 2H), 6.98 (s, 1H), 4.70-4.65 (m, 1H), 4.54, 4.50 (ABq, J_{AB}=11.0 Hz, 2H), 4.15 (dd, J=15.1, 4.3 Hz, 1H), 3.88 (dd, J=12.8, 7.2 Hz, 1H), 1.68 (d, J=6.7 Hz).

Example 2. 2-(((4-Methoxyphenyl)(methyl)amino)methyl)-6,7-dihydropyrazolo[1,5-a]pyrazin-4(5H)-one (J)

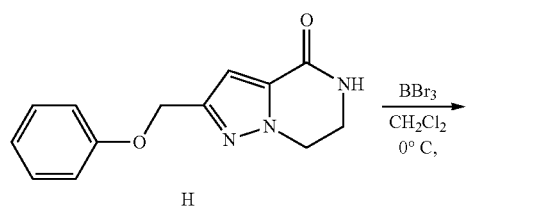

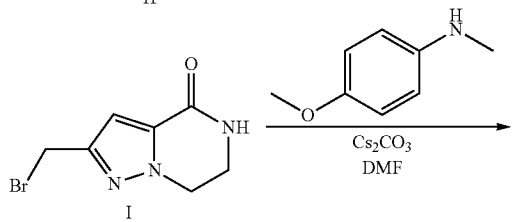

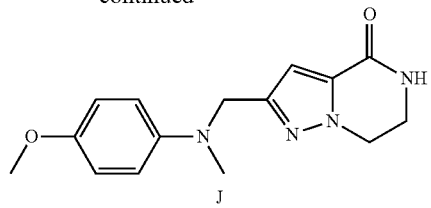

2-Bromomethyl)-6,7-dihydropyrazolo[1,5-a]pyrazin-4(5H)-one (I)

Compound H was prepared via a method analogous to that described in Example 1 for compound E. To a solution of H (1.0 g, 4.11 mmol, 1.00 eq.) in DCM (27.4 mL) at 0° C. was added a solution of 1M BBr₃ in DCM (12.33 mL, 12.33 mmol, 3.00 eq.). The reaction mixture was stirred at room temperature for 2 h, then diluted with CHCl₃/ⁿPrOH (3:1, v/v, 100 mL). The mixture was washed with saturated aqueous NaHCO₃ and 1M aqueous NaOH sequentially. The organic layer was dried over Na₂SO₄, filtered and concentrated in vacuo to provide the title compound (820 mg, 87%) as a tan solid which was used without further purification. ¹H NMR (400 MHz, DMSO-d₆) δ 8.24 (s, 1H), 6.77 (s, 1H), 4.64 (s, 2H), 4.30-427 (m, 2H), 3.62-3.58 (m, 2H). ES-MS [M+1]⁺: 230.1.

2-(((4-Methoxyphenyl)(methyl)amino)methyl)-6,7-dihydropyrazolo[1,5-a]pyrazin-4(5H)-one (J)

Compound I (690.18 mg, 3.00 mmol, 1.00 eq), 4-methoxy-N-methylaniline (720.20 mg, 5.25 mmol, 1.75 eq), Cs₂CO₃ (1.71 g, 5.25 mmol, 1.75 eq) and DMF (10.0 mL) were charged to a large reaction vial and stirred at 60° C. After 1 h, the reaction mixture was filtered through a pad of Celite which was washed with DMSO (5 mL). The crude material was purified using reverse phase HPLC to provide the title compound (491 mg, 57%) as an off-white powder: ¹H NMR (400 MHz, DMSO-d₆) δ 8.14 (s, 1H), 6.80-6.75 (m, 4H), 6.39 (s, 1H), 4.41 (s, 2H), 4.25-4.21 (m, 2H), 3.66 (s, 3H), 3.58-3.54 (m, 2H), 2.86 (s, 3H). ES-MS [M+1]⁺: 287.2

Example 3. 2-(Aminomethyl)-5-(4-fluorophenyl)-6,7-dihydropyrazolo[1,5-a]pyrazin-4(5H)-one hydrochloride (M)

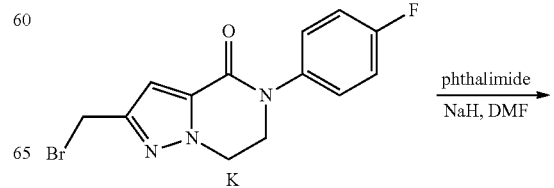

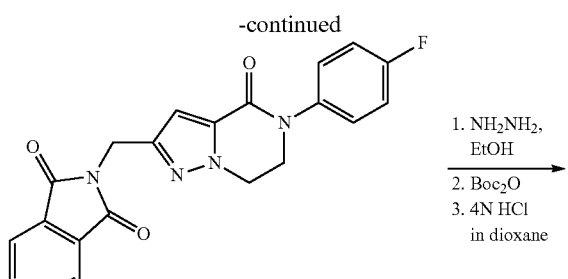

2-((5-(4-Fluorophenyl)-4-oxo-4,5,6,7-tetrahydropyrazolo[1,5-a]pyrazin-2-yl)methyl)isoindoline-1,3-dione (L)

Compound K was prepared via a method analogous to that described in Example 1. Phthalamide (330 mg, 2.24 mmol, 1.11 eq.) was taken up in DCM and dried over magnesium sulfate, filtered and concentrated. Freshly dried phthalamide was then taken up in DMF (5 mL). To this solution was added NaH (60 mg, 2.45 mmol, 1.2 eq.), and the mixture was allowed to stir for one hour. Compound K (660 mg, 2.04 mmol, 1 eq.) was then added. Reaction progress was monitored by LCMS and appeared complete within 1 hour. The reaction was diluted with water (20 mL) and was extracted with EtOAc (3×). The combined organic layers were washed with brine (3×). The organic layer was dried over $Na_2SO_4$ and concentrated in vacuo to afford the title compound as a yellow oil (584 mg, 69% yield) which was used without further purification. ES-MS [M+1]$^+$: 390.8.

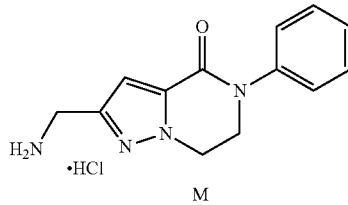

2-(Aminomethyl)-5-(4-fluorophenyl)-6,7-dihydropyrazolo[1,5-a]pyrazin-4(5H)-one hydrochloride (M)

Crude L (0.66 mmol, 1 eq.) was diluted with ethanol (10 mL). To this solution hydrazine hydrate (0.096 mL, 1.97 mmol, 3 eq.) was added. The reaction was refluxed until a white precipitate formed. The reaction was cooled to room temperature, filtered and concentrated. The crude residue was taken up in DCM (3 mL). To this was added triethylamine (0.457 mL, 3.28 mmol, 5 eq.), 4-dimethylaminopyridine (8 mg, 0.066 mmol, 0.1 eq.), and di-tert-butyl dicarbonate (0.151 mL, 0.66 mmol, 1.5 eq.). Once the BOC protection was deemed complete by LCMS, the reaction was concentrated in vacuo and purified via flash column chromatography (DCM/MeOH) to provide tert-butyl ((5-(4-fluorophenyl)-4-oxo-4,5,6,7-tetrahydropyrazolo[1,5-a]pyrazin-2-yl)methyl)carbamate. This intermediate was immediately treated with a 4N HCl solution in dioxane (2 mL). Reaction progress was monitored by LCMS and once deprotection was complete, the reaction was concentrated in vacuo, yielding the title compound (97 mg, 50% yield). $^1$H NMR (400 MHz, MeOD) δ 7.49-7.45 (m, 2H), 7.24 (t, J=8.7 Hz, 2H), 6.99 (s, 1H), 4.62-4.59 (m, 2H), 4.28-4.23 (m, 4H), 3.69 (s, 2H). ES-MS [M+1]$^+$: 261.0.

Example 4. 2-(Hydroxymethyl)-5-(4-methoxybenzyl)-6,7-dihydropyrazolo[1,5-a]pyrazin-4(5h)-one (R)

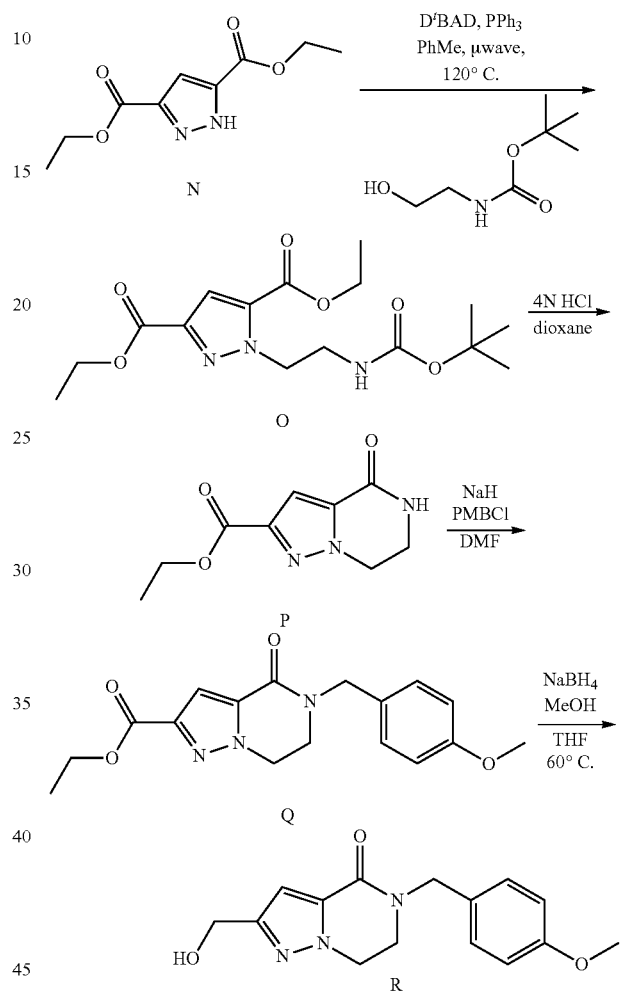

Diethyl 1-(2-((tert-butoxycarbonyl)amino)ethyl)-1h-pyrazole-3,5-dicarboxylate (O)

Diethyl 3,5-pyrazoledicarboxylate (2.12 g, 10.0 mmol, 1.00 eq) and N-Boc-ethanolamine (3.22 g, 20.0 mmol, 2.00 eq.) were dissolved in THF (72.0 mL) and triphenyl phosphine (4.72 g, 18.0 mmol, 1.80 eq.) was added. After 5 min, the mixture was cooled to 0° C. and di-tert-butyl azodicarboxylate (4.11 g, 18.0 mmol, 1.80 eq.) was added. The reaction mixture was then subjected to microwave irradiation for 20 min at 120° C. The mixture was cooled to room temperature and the solvent was removed in vacuo. Purification via flash chromatography on silica gel provided the title compound as a white powder (3.25 g, 91.5% yield). ES-MS [M+1]$^+$: 300.1.

Ethyl 4-oxo-4,5,6,7-tetrahydropyrazolo[1,5-a]pyrazine-2-carboxylate (P)

A solution of 4N HCl in 1,4-dioxane (36.6 mL, 9.15 mmol, 1.00 eq.) was added to compound O (3.25 g, 9.145 mmol, 1.00 eq.) at room temperature. After 1 h, saturated aqueous NaHCO₃ (~160 mL) was added. The mixture was stirred overnight and extracted with DCM (3×). The combined extracts were washed with brine, dried over Na₂SO₄, filtered, and concentrated in vacuo to provide the title compound (1.72 g, 77% yield) as a white powder which was used without further purification: ES-MS [M+1]⁺: 210.1.

Ethyl 5-(4-methoxybenzyl)-4-oxo-4,5,6,7-tetrahydropyrazolo[1,5-a]pyrazine-2-carboxylate (Q)

Compound P (1.50 g, 7.17 mmol, 1.00 eq.) was dissolved in DMF (36.0 mL), cooled to 0° C. and treated with 60% sodium hydride in mineral oil (345 mg, 1.20 mmol, 1.20 eq.) in five portions. The reaction mixture was stirred for 15 min and 4-methoxybenzyl chloride (1.17 mL, 1.20 mmol, 1.20 eq.) was added. After 2 h, the reaction mixture was diluted with water (50 mL) and extracted with EtOAc (3×). The combined extracts were washed with water, brine, dried over Na₂SO₄, filtered, and concentrated in vacuo. The crude material was purified by flash chromatography on silica gel (hexanes/EtOAc) to provide the title compound (2.25 g, 95% yield) as a pale yellow solid. ¹H NMR (400 MHz, CDCl₃) δ 7.28-7.25 (m, 3H), 6.91-6.89 (m, 2H), 4.71 (s, 2H), 4.43 (q, J=7.1 Hz, 2H), 4.41-4.38 (m, 2H), 3.82 (s, 3H), 3.69-3.66 (m, 2H), 1.42 (t, J=7.1 Hz, 3H). ES-MS [M+1]⁺: 329.9.

2-(Hydroxymethyl)-5-(4-methoxybenzyl)-6,7-dihydropyrazolo[1,5-a]pyrazin-4(5h)-one (R)

Sodium borohydride (1.29 g, 34.16 mmol, 5.00 eq.) was added slowly to a solution of compound Q (2.25 g, 6.83 mmol, 1.00 eq.) in THF (23 mL) and MeOH (6.83 mL) at 0° C. The reaction was heated to 60° C. and after 30 min at that temperature, the reaction mixture was diluted with water and extracted with DCM. The aqueous layer was acidified with a 1M aqueous HCl solution (~25 mL) and extracted with DCM (2×). The combined extracts were dried over Na₂SO₄ and concentrated in vacuo. Purification by flash chromatography on silica gel (DCM/MeOH) to provide of the title compound as a pale yellow solid (1.92 g, 98% yield). ¹H NMR (400 MHz, CDCl₃) δ 7.27-7.24 (m, 2H), 6.92-6.88 (m, 3H), 4.73 (s, 2H), 4.71 (s, 2H), 4.30-4.27 (m, 2H), 3.82 (s, 3H), 3.65-3.63 (m, 2H). ES-MS [M+1]⁺: 288.1.

Example 5. N-(4-(Difluoromethoxy)-2-fluorophenyl)-2,2,2-trifluoro-N-((4-oxo-4,5,6,7-tetrahydropyrazolo[1,5-a]pyrazin-2-yl)methyl)acetamide (V)

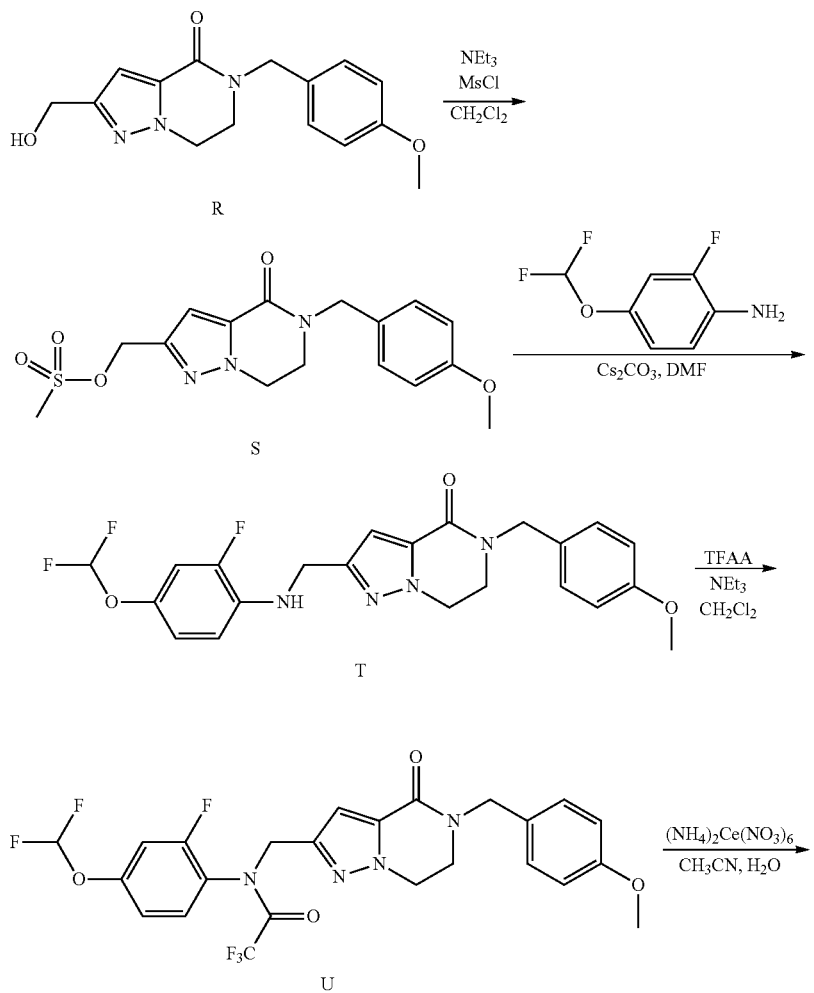

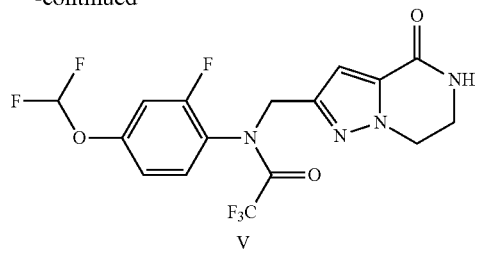

V

(5-(4-Methoxybenzyl)-4-oxo-4,5,6,7-tetrahydropyrazolo[1,5-a]pyrazin-2-yl)methyl methanesulfonate (S)

To a solution of compound R (1.40 g, 4.87 mmol, 1.00 eq.) in DCM (25 mL) at 0° C. was added triethylamine (1.02 mL, 7.31 mmol, 1.50 eq.) followed by methanesulfonyl chloride (0.57 mL, 7.31 mmol, 1.50 eq.). After 1 h, the mixture was diluted with water and extracted with EtOAc (3×). The combined organic extracts were washed with brine, dried over $Na_2SO_4$, filtered, and concentrated in vacuo. Purification by flash chromatography on silica gel (hexanes/EtOAc) provided a mixture of the title compound and the corresponding alkyl chloride, (2-(chloromethyl)-5-(4-methoxybenzyl)-6,7-dihydropyrazolo[1,5-c]pyrazin-4(5H)-one), as a pale yellow solid (1.58 g). ES-MS [M+1]$^+$: 366.2 and 306.2.

2-(((4-(Difluoromethoxy)-2-fluorophenyl)amino)methyl)-5-(4-methoxybenzyl)-6,7-dihydropyrazolo[1,5-a]pyrazin-4(5H)-one (T)

Compound S (1.58 g, 4.32 mmol, 1.00 eq), 4-(difluoromethoxy)-2-fluoro-aniline (3.83 mL, 21.6 mmol, 5.00 eq.), $Cs_2CO_3$ (2.11 g, 6.49 mmol, 1.50 eq.) and DMF (10.81 mL) were charged to a reaction vial. The mixture was stirred at 55° C. for 1 h. The mixture was then diluted with EtOAc (50 mL), washed with water (3×), brine, dried over $Na_2SO_4$ and concentrated in vacuo. Purification of the residue by flash chromatography on silica gel (hexanes/EtOAc) provided the title compound as a pale yellow oil (1.32 g, 68% yield). ES-MS [M+1]$^+$: 447.2.

N-(4-(Difluoromethoxy)-2-fluorophenyl)-2,2,2-trifluoro-N-((5-(4-methoxybenzyl)-4-oxo-4,5,6,7-tetrahydropyrazolo[1,5-c]pyrazin-2-yl)methyl)acetamide (U): Compound T (1.0 g, 2.24 mmol, 1.00 eq.) and triethylamine (0.468 mL, 3.36 mmol, 1.50 eq.) were dissolved in DCM (11.2 mL), cooled to 0° C. and trifluoroacetic anhydride (0.467 mL, 3.34 mmol, 1.50 eq.) was added slowly. After addition the reaction was removed from the ice bath. After 30 min at room temperature, the reaction mixture was diluted with DCM (25 mL) and saturated aqueous $NaHCO_3$ (10 mL) was added. The layers were separated, and the organic layer was washed with brine, dried over $Na_2SO_4$ and concentrated in vacuo. Purification of the residue by flash chromatography on silica gel (hexanes/EtOAc) provided the title compound (1.12 g, 90% yield). $^1$H NMR (400 MHz, CDCl$_3$) δ 7.27-7.24 (m, 2H), 7.14 (dd, J=8.6, 8.5 Hz, 1H), 6.99 (dd, J=10.2, 2.6 Hz, 1H), 6.91-6.87 (m, 3H), 6.84 (s, 1H), 6.56 (t, J=72.5 Hz, 1H), 5.32 (d, J=14.7 Hz, 1H), 4.71 (d, J=14.6 Hz, 1H), 4.66 (d, J=14.5 Hz, 1H), 4.47 (d, J=14.7 Hz, 1H), 4.25-4.22 (m, 2H), 3.82 (s, 3H), 3.65-3.61 (m, 2H). ES-MS [M+1]$^+$: 543.2.

N-(4-(Difluoromethoxy)-2-fluorophenyl)-2,2,2-trifluoro-N-((4-oxo-4,5,6,7-tetrahydropyrazolo[1,5-c]pyrazin-2-yl)methyl)acetamide (V): Compound U (650 mg, 1.2 mmol, 1.00 eq.) was dissolved in MeCN (11.53 mL) and a solution of ceric ammonium nitrate (2.63 g, 4.79 mmol, 4.00 eq.) in water (3.5 mL) was added. After 30 min at room temperature, solvents were removed in vacuo. Purification of the residue by flash chromatography on silica gel (DCM/MeOH) provided the title compound (480 mg, 95% yield) as a pale yellow powder. $^1$H NMR (400 MHz, DMSO-d$_6$) δ 8.22 (s, 1H), 7.49 (dd, J=8.8 Hz, 8.8 Hz, 1H), 7.37 (t, J=73.1 Hz, 1H), 7.34 (dd, J=10.8, 2.5 Hz, 1H), 7.09 (dd, J=8.8, 1.9 Hz, 1H), 6.57 (s, 1H), 4.99 (d, J=14.8 Hz, 1H), 4.73 (d, J=14.8 Hz, 1H), 4.24-4.20 (m, 2H), 3.58-3.55 (m, 2H). ES-MS [M+1]$^+$: 423.0.

Example 6. 2-Acetyl-5-(4-fluorophenyl)-6,7-dihydropyrazolo[1,5-a]pyrazin-4(5H)-one (AA)

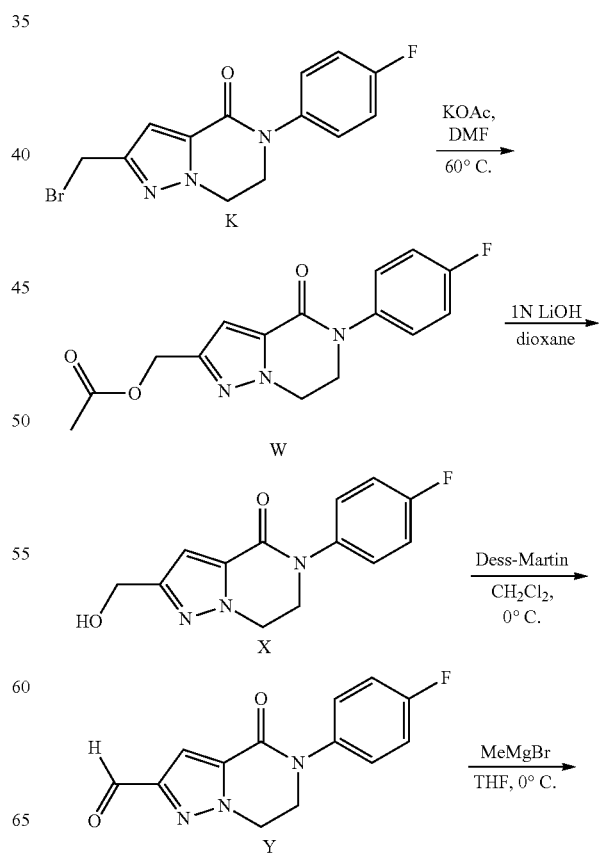

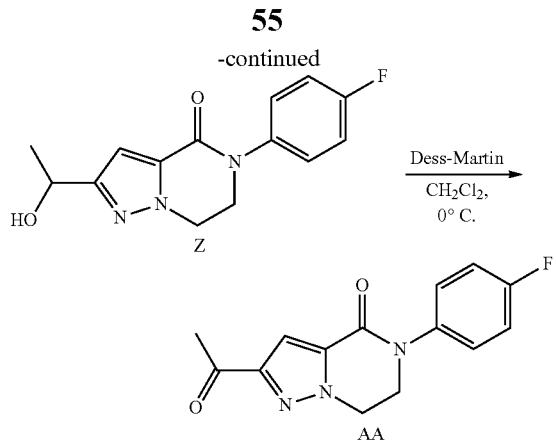

(5-(4-Fluorophenyl)-4-oxo-4,5,6,7-tetrahydropyrazolo[1,5-a]pyrazin-2-yl)methyl acetate (W)

Compound K was prepared via a method analogous to that described in Example 1. Potassium acetate (3.39 g, 34.55 mmol, 3.50 eq.) was added to a solution of K (3.2 g, 9.87 mmol, 1.00 eq.) in DMF (50 mL). The mixture was stirred at 60° C. for 2 h, then diluted with EtOAc (200 mL), washed with water, brine, dried over $Na_2SO_4$, and concentrated in vacuo. Purification by flash chromatography afforded the title compound (2.80 g, 93% yield) as a pale yellow crystalline solid. $^1$H NMR (400 MHz, CDCl$_3$) δ 7.34-7.29 (m, 2H), 7.17-7.11 (m, 2H), 6.9 (s, 1H), 5.2 (s, 2H), 4.55-4.52 (m, 2H), 4.19-4.16 (m, 2H), 2.12 (s, 3H). ES-MS [M+1]$^+$: 304.0.

5-(4-Fluorophenyl)-2-(hydroxymethyl)-6,7-dihydropyrazolo[1,5-a]pyrazin-4(5H)-one (X)

Compound W (2.80 g, 9.32 mmol, 1.00 eq.) was dissolved in MeOH (9.3 mL) and THF (9.3 mL). To this 1N aqueous LiOH (46.2 mL, 46.2 mmol, 5.0 eq.) was added. The mixture was stirred for 30 min, then diluted with water and extracted with EtOAc (3×). The combined organic extracts were washed with brine, dried over $Na_2SO_4$ and concentrated in vacuo. Purification by flash chromatography (hexanes/EtOAc) gave the title compound (2.19 g, 91% yield) as a white solid. $^1$H NMR (400 MHz, CDCl$_3$) δ 7.36-7.33 (m, 2H), 7.17-7.15 (m, 2H), 6.9 (s, 1H), 4.76 (d, J=5.9 Hz, 2H), 4.55-4.52 (m, 2H), 4.19-4.17 (m, 2H), 1.9 (t, J=5.9 Hz, 1H). ES-MS [M+1]$^+$: 262.0.

5-(4-Fluorophenyl)-4-oxo-4,5,6,7-tetrahydropyrazolo[1,5-a]pyrazine-2-carbaldehyde (Y)

Dess-Martin periodinane (2.23 g, 5.25 mmol, 1.50 eq.) was added to a solution of compound X (915 mg, 3.5 mmol, 1.00 eq.) in DCM (35 mL) at 0° C. After 2 h, saturated aqueous $Na_2S_2O_3$ (40 mL), and saturated aqueous NaHCO$_3$ (40 mL) were added. The mixture was stirred for 10 min and extracted with DCM (3×). The combined extracts were washed with brine, dried over $Na_2SO_4$, filtered and concentrated in vacuo. Purification by flash chromatography (hexanes/EtOAc) afforded the title compound (890 mg, 97% yield) as a white powder. ES-MS [M+1]$^+$: 260.0.

5-(4-Fluorophenyl)-2-(1-hydroxyethyl)-6,7-dihydropyrazolo[1,5-a]pyrazin-4(5H)-one (Z)

A solution of 3M methylmagnesium bromide in diethyl ether (1.31 mL, 3.94 mmol, 1.20 eq.) was added slowly to a solution of compound Y (850 mg, 3.28 mmol, 1.00 eq.) in THF (18.2 mL) at 0° C. After stirring at 0° C. for 45 min, the mixture was cooled to −20° C. and EtOH (2.0 mL) was added. The mixture was stirred for 10 min, saturated aqueous NH$_4$Cl (4 mL) was added. The mixture was warmed to room temperature and extracted with EtOAc (3×). The combined organic extracts were washed with brine, dried over $Na_2SO_4$ and concentrated in vacuo. Purification by flash chromatography (hexanes/EtOAc) to provide the title compound (827 mg, 91% yield) as a white powder. $^1$H NMR (400 MHz, DMSO-d$_6$) δ 7.47-7.42 (m, 2H), 7.31-7.26 (m, 2H), 6.7 (s, 1H), 5.18 (d, J=5.0 Hz, 1H), 4.74 (dq, J=6.4, 6.2 Hz, 1H), 4.47-4.44 (m, 2H), 4.17-4.14 (m, 2H), 1.39 (d, J=6.5 Hz, 3H). ES-MS [M+1]$^+$: 276.0.

2-Acetyl-5-(4-fluorophenyl)-6,7-dihydropyrazolo[1,5-a]pyrazin-4(5H)-one (AA)

Dess-Martin periodinane (318 mg, 0.75 mmol, 1.50 eq.) was added to a solution of 26 (137.64 mg, 0.5 mmol, 1.00 eq.) in DCM (5.0 mL) at 0° C. After 2 h, saturated aqueous $Na_2S_2O_3$ (10 mL) and saturated aqueous NaHCO$_3$ (10 mL) were added. The resulting mixture was stirred for 10 min and extracted with DCM (3×). The combined organic extracts were washed with brine, dried over $Na_2SO_4$ and concentrated in vacuo. Purification of the residue by flash chromatography (hexanes/EtOAc) gave the title compound (116 mg, 85% yield) as a white powder. $^1$H NMR (400 MHz, CDCl$_3$) δ 7.47 (s, 1H), 7.37-7.32 (m, 2H), 7.19-7.14 (m, 2H), 4.64-4.61 (m, 2H), 4.25-4.22 (m, 2H), 2.63 (s, 3H). ES-MS [M+1]$^+$: 274.2.

Example 7. 5-(3,4-Difluorophenyl)-2-(((4-methoxyphenyl)amino)methyl)-6,7-dihydropyrazolo[1,5-c]pyrazin-4(5H)-one (1)

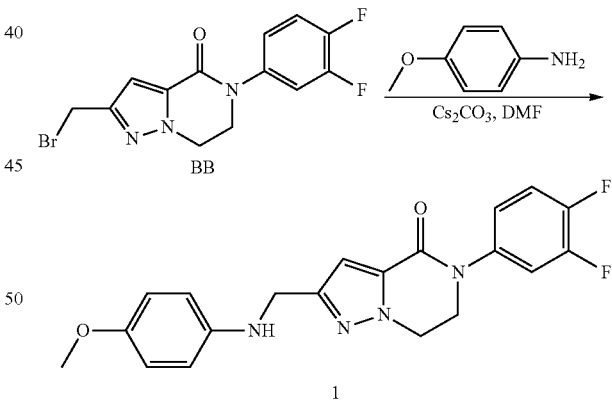

5-(3,4-Difluorophenyl)-2-(((4-methoxyphenyl)amino)methyl)-6,7-dihydropyrazolo[1,5-a]pyrazin-4(5H)-one (1)

Compound BB was prepared via a method analogous to that described in Example 1. Compound BB (257 mg, 0.75 mmol, 1.00 eq.) and Cs$_2$CO$_3$ (244 mg, 0.75 mmol, 1 eq.) were dissolved in DMF (3.5 mL) and p-anisidine (616 mg, 5.0 mmol, 6.67 eq.) was added. After 1 h, the mixture was diluted with EtOAc (20 mL) and washed with water (3×), brine, dried over $Na_2SO_4$ and concentrated in vacuo. Purification of the residue by flash chromatography on silica gel (hexanes/EtOAc) to provide the title compound (253 mg, 88% yield) as an off white powder. $^1$H NMR (400 MHz, CDCl$_3$) δ 7.27-7.21 (m, 2H), 7.11-7.08 (m, 1H), 2 Hz, 1H), 6.91 (s, 1H), 6.82-6.79 (m, 2H), 6.72-6.68 (m, 2H), 4.54-4.51 (m, 2H), 4.37 (s, 2H), 4.78-4.16 (m, 2H), 3.77 (s, 3H). ES-MS [M+1]$^+$: 385.0.

The following compounds were prepared in an analogous manner:

| No. | Name | ES-MS [M + 1]$^+$ |
|---|---|---|
| 2 | 5-(4-fluorophenyl)-2-((phenylamino)methyl)-6,7-dihydropyrazolo[1,5-a]pyrazin-4(5H)-one | 337.0 |
| 3 | 5-(4-fluorophenyl)-2-(((2-fluorophenyl)amino)methyl)-6,7-dihydropyrazolo[1,5-a]pyrazin-4(5H)-one | 355.0 |
| 4 | 5-(4-fluorophenyl)-2-((o-tolylamino)methyl)-6,7-dihydropyrazolo[1,5-a]pyrazin-4(5H)-one | 351.0 |
| 5 | 2-(((2-chlorophenyl)amino)methyl)-5-(4-fluorophenyl)-6,7-dihydropyrazolo[1,5-a]pyrazin-4(5H)-one | 371.0 |
| 6 | 5-(4-fluorophenyl)-2-(((2-methoxyphenyl)amino)methyl)-6,7-dihydropyrazolo[1,5-a]pyrazin-4(5H)-one | 367.0 |
| 7 | 5-(4-fluorophenyl)-2-(((3-fluorophenyl)amino)methyl)-6,7-dihydropyrazolo[1,5-a]pyrazin-4(5H)-one | 355.0 |
| 8 | 5-(4-fluorophenyl)-2-((m-tolylamino)methyl)-6,7-dihydropyrazolo[1,5-a]pyrazin-4(5H)-one | 351.0 |
| 9 | 2-(((3-chlorophenyl)amino)methyl)-5-(4-fluorophenyl)-6,7-dihydropyrazolo[1,5-a]pyrazin-4(5H)-one | 371.0 |
| 10 | 5-(4-fluorophenyl)-2-(((3-methoxyphenyl)amino)methyl)-6,7-dihydropyrazolo[1,5-a]pyrazin-4(5H)-one | 367.0 |
| 11 | 3-(((5-(4-fluorophenyl)-4-oxo-4,5,6,7-tetrahydropyrazolo[1,5-a]pyrazin-2-yl)methyl)amino)benzonitrile | 362.0 |
| 12 | 2-(((3-(difluoromethoxy)phenyl)amino)methyl)-5-(4-fluorophenyl)-6,7-dihydropyrazolo[1,5-a]pyrazin-4(5H)-one | 403.0 |
| 13 | 5-(4-fluorophenyl)-2-(((4-fluorophenyl)amino)methyl)-6,7-dihydropyrazolo[1,5-a]pyrazin-4(5H)-one | 355.0 |
| 14 | 5-(4-fluorophenyl)-2-((p-tolylamino)methyl)-6,7-dihydropyrazolo[1,5-a]pyrazin-4(5H)-one | 351.0 |
| 15 | 2-(((4-chlorophenyl)amino)methyl)-5-(4-fluorophenyl)-6,7-dihydropyrazolo[1,5-a]pyrazin-4(5H)-one | 371.0 |
| 16 | 2-(((4-bromophenyl)amino)methyl)-5-(4-fluorophenyl)-6,7-dihydropyrazolo[1,5-a]pyrazin-4(5H)-one | 415.0 |
| 17 | 5-(4-fluorophenyl)-2-(((4-methoxyphenyl)amino)methyl)-6,7-dihydropyrazolo[1,5-a]pyrazin-4(5H)-one | 367.0 |
| 18 | 4-(((5-(4-fluorophenyl)-4-oxo-4,5,6,7-tetrahydropyrazolo[1,5-a]pyrazin-2-yl)methyl)amino)benzonitrile | 362.0 |
| 19 | 5-(4-fluorophenyl)-2-(((4-(trifluoromethyl)phenyl)amino)methyl)-6,7-dihydropyrazolo[1,5-a]pyrazin-4(5H)-one | 405.0 |
| 20 | 2-(((4-(difluoromethoxy)phenyl)amino)methyl)-5-(4-fluorophenyl)-6,7-dihydropyrazolo[1,5-a]pyrazin-4(5H)-one | 403.0 |
| 21 | 5-(4-fluorophenyl)-2-(((4-(trifluoromethoxy)phenyl)amino)methyl)-6,7-dihydropyrazolo[1,5-a]pyrazin-4(5H)-one | 421.0 |
| 22 | 2-(((4-ethylphenyl)amino)methyl)-5-(4-fluorophenyl)-6,7-dihydropyrazolo[1,5-a]pyrazin-4(5H)-one | 365.0 |
| 23 | 5-(4-fluorophenyl)-2-(((4-isopropylphenyl)amino)methyl)-6,7-dihydropyrazolo[1,5-a]pyrazin-4(5H)-one | 379.0 |
| 24 | 2-(((4-(tert-butyl)phenyl)amino)methyl)-5-(4-fluorophenyl)-6,7-dihydropyrazolo[1,5-a]pyrazin-4(5H)-one | 393.0 |
| 25 | 5-(4-fluorophenyl)-2-(((4-(methylsulfonyl)phenyl)amino)methyl)-6,7-dihydropyrazolo[1,5-a]pyrazin-4(5H)-one | 415.0 |
| 26 | 2-(4-(((5-(4-fluorophenyl)-4-oxo-4,5,6,7-tetrahydropyrazolo[1,5-a]pyrazin-2-yl)methyl)amino)phenyl)acetonitrile | 376.0 |
| 27 | 2-(((2,3-difluorophenyl)amino)methyl)-5-(4-fluorophenyl)-6,7-dihydropyrazolo[1,5-a]pyrazin-4(5H)-one | 373.0 |
| 28 | 2-(((2,4-difluorophenyl)amino)methyl)-5-(4-fluorophenyl)-6,7-dihydropyrazolo[1,5-a]pyrazin-4(5H)-one | 373.0 |
| 29 | 2-(((2,5-difluorophenyl)amino)methyl)-5-(4-fluorophenyl)-6,7-dihydropyrazolo[1,5-a]pyrazin-4(5H)-one | 373.0 |
| 30 | 2-(((3,5-difluorophenyl)amino)methyl)-5-(4-fluorophenyl)-6,7-dihydropyrazolo[1,5-a]pyrazin-4(5H)-one | 373.0 |
| 31 | 2-(((3,4-difluorophenyl)amino)methyl)-5-(4-fluorophenyl)-6,7-dihydropyrazolo[1,5-a]pyrazin-4(5H)-one | 373.0 |
| 32 | 2-(((2,6-difluorophenyl)amino)methyl)-5-(4-fluorophenyl)-6,7-dihydropyrazolo[1,5-a]pyrazin-4(5H)-one | 373.0 |
| 33 | 5-(4-fluorophenyl)-2-(((2,4,6-trifluorophenyl)amino)methyl)-6,7-dihydropyrazolo[1,5-a]pyrazin-4(5H)-one | 391.0 |
| 34 | 2-(((4-chloro-2-fluorophenyl)amino)methyl)-5-(4-fluorophenyl)-6,7-dihydropyrazolo[1,5-a]pyrazin-4(5H)-one | 389.0 |
| 35 | 2-(((2-fluoro-4-methylphenyl)amino)methyl)-5-(4-fluorophenyl)-6,7-dihydropyrazolo[1,5-a]pyrazin-4(5H)-one | 369.0 |
| 36 | 2-(((4-fluoro-3-methylphenyl)amino)methyl)-5-(4-fluorophenyl)-6,7-dihydropyrazolo[1,5-a]pyrazin-4(5H)-one | 369.0 |
| 37 | 2-(((4-(difluoromethoxy)-2-fluorophenyl)amino)methyl)-5-(4-fluorophenyl)-6,7-dihydropyrazolo[1,5-a]pyrazin-4(5H)-one | 420.8 |
| 38 | 2-(((4-(difluoromethoxy)-3-fluorophenyl)amino)methyl)-5-(4-fluorophenyl)-6,7-dihydropyrazolo[1,5-a]pyrazin-4(5H)-one | 420.8 |
| 39 | 2-(((2,2-difluorobenzo[d][1,3]dioxol-5-yl)amino)methyl)-5-(4-fluorophenyl)-6,7-dihydropyrazolo[1,5-a]pyrazin-4(5H)-one | 417.0 |
| 40 | (R)-5-(4-fluorophenyl)-7-methyl-2-((phenylamino)methyl)-6,7-dihydropyrazolo[1,5-a]pyrazin-4(5H)-one | 350.9 |
| 41 | (S)-5-(4-fluorophenyl)-7-methyl-2-((phenylamino)methyl)-6,7-dihydropyrazolo[1,5-a]pyrazin-4(5H)-one | 350.9 |
| 42 | (R)-5-(4-fluorophenyl)-2-(((2-fluorophenyl)amino)methyl)-7-methyl-6,7-dihydropyrazolo[1,5-a]pyrazin-4(5H)-one | 368.9 |
| 43 | (S)-5-(4-fluorophenyl)-2-(((2-fluorophenyl)amino)methyl)-7-methyl-6,7-dihydropyrazolo[1,5-a]pyrazin-4(5H)-one | 368.9 |
| 44 | (R)-5-(4-fluorophenyl)-7-methyl-2-((o-tolylamino)methyl)-6,7-dihydropyrazolo[1,5-a]pyrazin-4(5H)-one | 364.9 |
| 45 | (S)-5-(4-fluorophenyl)-7-methyl-2-((o-tolylamino)methyl)-6,7-dihydropyrazolo[1,5-a]pyrazin-4(5H)-one | 364.9 |
| 46 | (R)-5-(4-fluorophenyl)-2-(((3-fluorophenyl)amino)methyl)-7-methyl-6,7-dihydropyrazolo[1,5-a]pyrazin-4(5H)-one | 368.8 |

-continued

| No. | Name | ES-MS [M + 1]+ |
|---|---|---|
| 47 | (S)-5-(4-fluorophenyl)-2-(((3-fluorophenyl)amino)methyl)-7-methyl-6,7-dihydropyrazolo[1,5-a]pyrazin-4(5H)-one | 368.9 |
| 48 | (R)-2-(((3-chlorophenyl)amino)methyl)-5-(4-fluorophenyl)-7-methyl-6,7-dihydropyrazolo[1,5-a]pyrazin-4(5H)-one | 384.8 |
| 49 | (S)-2-(((3-chlorophenyl)amino)methyl)-5-(4-fluorophenyl)-7-methyl-6,7-dihydropyrazolo[1,5-a]pyrazin-4(5H)-one | 384.8 |
| 50 | (R)-5-(4-fluorophenyl)-7-methyl-2-((m-tolylamino)methyl)-6,7-dihydropyrazolo[1,5-a]pyrazin-4(5H)-one | 364.9 |
| 51 | (S)-5-(4-fluorophenyl)-7-methyl-2-((m-tolylamino)methyl)-6,7-dihydropyrazolo[1,5-a]pyrazin-4(5H)-one | 364.9 |
| 52 | (R)-5-(4-fluorophenyl)-2-(((3-methoxyphenyl)amino)methyl)-7-methyl-6,7-dihydropyrazolo[1,5-a]pyrazin-4(5H)-one | 380.9 |
| 53 | (S)-5-(4-fluorophenyl)-2-(((3-methoxyphenyl)amino)methyl)-7-methyl-6,7-dihydropyrazolo[1,5-a]pyrazin-4(5H)-one | 380.9 |
| 54 | (R)-2-(((3-(difluoromethoxy)phenyl)amino)methyl)-5-(4-fluorophenyl)-7-methyl-6,7-dihydropyrazolo[1,5-a]pyrazin-4(5H)-one | 416.8 |
| 55 | (S)-2-(((3-(difluoromethoxy)phenyl)amino)methyl)-5-(4-fluorophenyl)-7-methyl-6,7-dihydropyrazolo[1,5-a]pyrazin-4(5H)-one | 416.8 |
| 56 | (R)-5-(4-fluorophenyl)-2-(((4-fluorophenyl)amino)methyl)-7-methyl-6,7-dihydropyrazolo[1,5-a]pyrazin-4(5H)-one | 368.9 |
| 57 | (S)-5-(4-fluorophenyl)-2-(((4-fluorophenyl)amino)methyl)-7-methyl-6,7-dihydropyrazolo[1,5-a]pyrazin-4(5H)-one | 368.9 |
| 58 | (R)-5-(4-fluorophenyl)-7-methyl-2-((p-tolylamino)methyl)-6,7-dihydropyrazolo[1,5-a]pyrazin-4(5H)-one | 364.9 |
| 59 | (S)-5-(4-fluorophenyl)-7-methyl-2-((p-tolylamino)methyl)-6,7-dihydropyrazolo[1,5-a]pyrazin-4(5H)-one | 364.9 |
| 60 | (R)-2-(((4-chlorophenyl)amino)methyl)-5-(4-fluorophenyl)-7-methyl-6,7-dihydropyrazolo[1,5-a]pyrazin-4(5H)-one | 384.8 |
| 61 | (S)-2-(((4-chlorophenyl)amino)methyl)-5-(4-fluorophenyl)-7-methyl-6,7-dihydropyrazolo[1,5-a]pyrazin-4(5H)-one | 384.8 |
| 62 | (R)-5-(4-fluorophenyl)-2-(((4-methoxyphenyl)amino)methyl)-7-methyl-6,7-dihydropyrazolo[1,5-a]pyrazin-4(5H)-one | 380.9 |
| 63 | (S)-5-(4-fluorophenyl)-2-(((4-methoxyphenyl)amino)methyl)-7-methyl-6,7-dihydropyrazolo[1,5-a]pyrazin-4(5H)-one | 380.9 |
| 64 | (R)-2-(((4-(difluoromethoxy)phenyl)amino)methyl)-5-(4-fluorophenyl)-7-methyl-6,7-dihydropyrazolo[1,5-a]pyrazin-4(5H)-one | 416.8 |
| 65 | (S)-2-(((4-(difluoromethoxy)phenyl)amino)methyl)-5-(4-fluorophenyl)-7-methyl-6,7-dihydropyrazolo[1,5-a]pyrazin-4(5H)-one | 416.8 |
| 66 | (R)-2-(4-(((5-(4-fluorophenyl)-7-methyl-4-oxo-4,5,6,7-tetrahydropyrazolo[1,5-a]pyrazin-2-yl)methyl)amino)phenyl)acetonitrile | 389.9 |
| 67 | (S)-2-(4-(((5-(4-fluorophenyl)-7-methyl-4-oxo-4,5,6,7-tetrahydropyrazolo[1,5-a]pyrazin-2-yl)methyl)amino)phenyl)acetonitrile | 389.9 |
| 68 | (R)-2-(((2,3-difluorophenyl)amino)methyl)-5-(4-fluorophenyl)-7-methyl-6,7-dihydropyrazolo[1,5-a]pyrazin-4(5H)-one | 386.9 |
| 69 | (S)-2-(((2,3-difluorophenyl)amino)methyl)-5-(4-fluorophenyl)-7-methyl-6,7-dihydropyrazolo[1,5-a]pyrazin-4(5H)-one | 386.8 |
| 70 | (R)-2-(((2,5-difluorophenyl)amino)methyl)-5-(4-fluorophenyl)-7-methyl-6,7-dihydropyrazolo[1,5-a]pyrazin-4(5H)-one | 386.8 |
| 71 | (S)-2-(((2,5-difluorophenyl)amino)methyl)-5-(4-fluorophenyl)-7-methyl-6,7-dihydropyrazolo[1,5-a]pyrazin-4(5H)-one | 386.8 |
| 72 | (R)-2-(((2,6-difluorophenyl)amino)methyl)-5-(4-fluorophenyl)-7-methyl-6,7-dihydropyrazolo[1,5-a]pyrazin-4(5H)-one | 386.8 |
| 73 | (S)-2-(((2,6-difluorophenyl)amino)methyl)-5-(4-fluorophenyl)-7-methyl-6,7-dihydropyrazolo[1,5-a]pyrazin-4(5H)-one | 386.9 |
| 74 | (S)-2-(((3,5-difluorophenyl)amino)methyl)-5-(4-fluorophenyl)-7-methyl-6,7-dihydropyrazolo[1,5-a]pyrazin-4(5H)-one | 386.8 |
| 75 | (R)-2-(((2,4-difluorophenyl)amino)methyl)-5-(4-fluorophenyl)-7-methyl-6,7-dihydropyrazolo[1,5-a]pyrazin-4(5H)-one | 386.8 |
| 76 | (S)-2-(((2,4-difluorophenyl)amino)methyl)-5-(4-fluorophenyl)-7-methyl-6,7-dihydropyrazolo[1,5-a]pyrazin-4(5H)-one | 386.8 |
| 77 | (R)-2-(((3,4-difluorophenyl)amino)methyl)-5-(4-fluorophenyl)-7-methyl-6,7-dihydropyrazolo[1,5-a]pyrazin-4(5H)-one | 386.9 |
| 78 | (S)-2-(((3,4-difluorophenyl)amino)methyl)-5-(4-fluorophenyl)-7-methyl-6,7-dihydropyrazolo[1,5-a]pyrazin-4(5H)-one | 386.9 |
| 79 | (R)-5-(4-fluorophenyl)-7-methyl-2-(((2,4,6-trifluorophenyl)amino)methyl)-6,7-dihydropyrazolo[1,5-a]pyrazin-4(5H)-one | 404.8 |
| 80 | (S)-5-(4-fluorophenyl)-7-methyl-2-(((2,4,6-trifluorophenyl)amino)methyl)-6,7-dihydropyrazolo[1,5-a]pyrazin-4(5H)-one | 404.8 |
| 81 | 5-(4-chlorophenyl)-2-(((4-methoxyphenyl)amino)methyl)-6,7-dihydropyrazolo[1,5-a]pyrazin-4(5H)-one | 383.2 |
| 82 | 5-(4-fluorophenyl)-2-((methyl(phenyl)amino)methyl)-6,7-dihydropyrazolo[1,5-a]pyrazin-4(5H)-one | 351.0 |
| 83 | 5-(4-fluorophenyl)-2-(((2-fluorophenyl)(methyl)amino)methyl)-6,7-dihydropyrazolo[1,5-a]pyrazin-4(5H)-one | 369.0 |
| 84 | 2-(((2-chlorophenyl)(methyl)amino)methyl)-5-(4-fluorophenyl)-6,7-dihydropyrazolo[1,5-a]pyrazin-4(5H)-one | 385.0 |
| 85 | 5-(4-fluorophenyl)-2-(((2-methoxyphenyl)(methyl)amino)methyl)-6,7-dihydropyrazolo[1,5-a]pyrazin-4(5H)-one | 381.0 |
| 86 | 5-(4-fluorophenyl)-2-(((3-fluorophenyl)(methyl)amino)methyl)-6,7-dihydropyrazolo[1,5-a]pyrazin-4(5H)-one | 369.0 |
| 87 | 2-(((3-chlorophenyl)(methyl)amino)methyl)-5-(4-fluorophenyl)-6,7-dihydropyrazolo[1,5-a]pyrazin-4(5H)-one | 385.0 |
| 88 | 5-(4-fluorophenyl)-2-(((3-methoxyphenyl)(methyl)amino)methyl)-6,7-dihydropyrazolo[1,5-a]pyrazin-4(5H)-one | 381.0 |
| 89 | 5-(4-fluorophenyl)-2-(((4-fluorophenyl)(methyl)amino)methyl)-6,7-dihydropyrazolo[1,5-a]pyrazin-4(5H)-one | 369.0 |
| 90 | 2-(((4-chlorophenyl)(methyl)amino)methyl)-5-(4-fluorophenyl)-6,7-dihydropyrazolo[1,5-a]pyrazin-4(5H)-one | 385.0 |
| 91 | 2-(((4-bromophenyl)(methyl)amino)methyl)-5-(4-fluorophenyl)-6,7-dihydropyrazolo[1,5-a]pyrazin-4(5H)-one | 429.0 |
| 92 | 5-(4-fluorophenyl)-2-(((4-methoxyphenyl)(methyl)amino)methyl)-6,7-dihydropyrazolo[1,5-a]pyrazin-4(5H)-one | 381.0 |

-continued

| No. | Name | ES-MS [M + 1]+ |
|---|---|---|
| 93 | 4-(((5-(4-fluorophenyl)-4-oxo-4,5,6,7-tetrahydropyrazolo[1,5-a]pyrazin-2-yl)methyl)(methyl)amino)benzonitrile | 376.0 |
| 94 | 2-(((3,5-difluorophenyl)(methyl)amino)methyl)-5-(4-fluorophenyl)-6,7-dihydropyrazolo[1,5-a]pyrazin-4(5H)-one | 386.8 |

Example 8. 2-(((4-(Difluoromethoxy)-2-fluorophenyl)amino)methyl)-5-(3-fluorophenyl)-6,7-dihydropyrazolo[1,5-c]pyrazin-4(5H)-one (95)

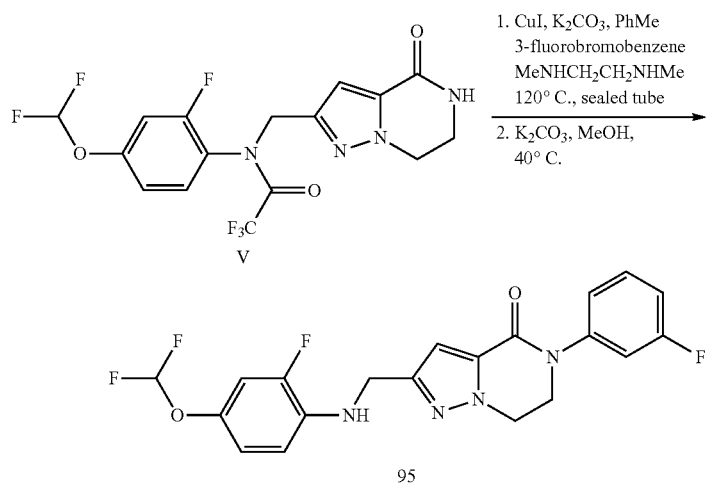

2-(((4-(Difluoromethoxy)-2-fluorophenyl)amino)methyl)-5-(3-fluorophenyl)-6,7-dihydropyrazolo[1,5-a]pyrazin-4(5H)-one (95)

Copper(I) iodide (15.63 mg, 0.082 mmol, 2.05 eq.) was added to a suspension of compound V (16.89 mg, 0.04 mmol, 1.00 eq.), 3-fluorobromobenzene (8.40 uL, 0.082 mmol, 2.05 eq.), potassium carbonate (11.3 mg, 0.082 mmol, 2.05 eq.) and N,N'-dimethylethylenediamine (23.68 uL, 0.22 mmol, 5.05 eq.) in toluene (0.440 mL) in a sealed tube. The reaction mixture was stirred at 120° C. for 16 h. The mixture was then cooled to 40° C., MeOH (1.0 mL) and potassium carbonate (11.3 mg, 0.08 mmol, 2.05 eq.) were added. After 1 h, the mixture was diluted with EtOAc (2.0 mL), filtered through a Celite pad which was rinsed with EtOAc (2×) and concentrated in vacuo. Purification of the residue using reverse phase HPLC provided the title compound (5.10 mg, 29%) as a white powder. $^1$H NMR (400 MHz, CDCl$_3$) δ 7.45-7.39 (m, 1H), 7.17-7.15 (m, 1H), 7.12 (dd, J=2.3, 2.2 Hz, 1H), 7.06-7.00 (m, 1H), 6.93-6.83 (m, 3H), 6.73 (dd, J=9.2, 8.9 Hz, 1H), 6.40 (t, J=74.2 Hz, 1H), 4.55-4.52 (m, 2H), 4.44 (s, 2H), 4.23-4.20 (m, 2H). ES-MS [M+1]+: 423.0.

The following compounds were prepared in an analogous manner. If the starting material has no trifluoracetamide (ie. R$^3$=alkyl), then the second step of the sequence is not required.

| No. | Name | ES-MS [M + 1]+ |
|---|---|---|
| 96 | 5-(4-chlorophenyl)-2-(((4-methoxyphenyl)(methyl)amino)methyl)-6,7-dihydropyrazolo[1,5-a]pyrazin-4(5H)-one | 396.9 |
| 97 | 5-(3,4-difluorophenyl)-2-(((4-methoxyphenyl)(methyl)amino)methyl)-6,7-dihydropyrazolo[1,5-a]pyrazin-4(5H)-one | 398.9 |
| 98 | 5-(3-chlorophenyl)-2-(((4-methoxyphenyl)(methyl)amino)methyl)-6,7-dihydropyrazolo[1,5-a]pyrazin-4(5H)-one | 396.9 |

-continued

| No. | Name | ES-MS [M + 1]+ |
|---|---|---|
| 99 | 2-(((4-methoxyphenyl)(methyl)amino)methyl)-5-(p-tolyl)-6,7-dihydropyrazolo[1,5-a]pyrazin-4(5H)-one | 376.9 |
| 100 | 5-(2-chlorophenyl)-2-(((4-methoxyphenyl)(methyl)amino)methyl)-6,7-dihydropyrazolo[1,5-a]pyrazin-4(5H)-one | 396.9 |
| 101 | 5-(3-fluorophenyl)-2-(((4-methoxyphenyl)(methyl)amino)methyl)-6,7-dihydropyrazolo[1,5-a]pyrazin-4(5H)-one | 380.9 |
| 102 | 2-(((4-methoxyphenyl)(methyl)amino)methyl)-5-(2,4,6-trifluorophenyl)-6,7-dihydropyrazolo[1,5-a]pyrazin-4(5H)-one | 416.8 |
| 103 | 2-(((4-methoxyphenyl)(methyl)amino)methyl)-5-(m-tolyl)-6,7-dihydropyrazolo[1,5-a]pyrazin-4(5H)-one | 376.9 |
| 104 | 5-(3,5-difluorophenyl)-2-(((4-methoxyphenyl)(methyl)amino)methyl)-6,7-dihydropyrazolo[1,5-a]pyrazin-4(5H)-one | 398.9 |
| 105 | 5-(2-fluorophenyl)-2-(((4-methoxyphenyl)(methyl)amino)methyl)-6,7-dihydropyrazolo[1,5-a]pyrazin-4(5H)-one | 380.9 |

| No. | Name | ES-MS [M + 1]+ |
|---|---|---|
| 106 | 5-(2,5-difluorophenyl)-2-(((4-methoxyphenyl)(methyl)amino)methyl-6,7-dihydropyrazolo[1,5-a]pyrazin-4(5H)-one | 398.9 |
| 107 | 5-(2,3-difluorophenyl)-2-(((4-methoxyphenyl)(methyl)amino)methyl-6,7-dihydropyrazolo[1,5-a]pyrazin-4(5H)-one | 398.9 |
| 108 | 5-(2-fluoro-4-methylphenyl)-2-(((4-methoxyphenyl)(methyl)amino)methyl-6,7-dihydropyrazolo[1,5-a]pyrazin-4(5H)-one | 394.9 |
| 109 | 5-(4-fluoro-2-methylphenyl)-2-(((4-methoxyphenyl)(methyl)amino)methyl-6,7-dihydropyrazolo[1,5-a]pyrazin-4(5H)-one | 394.9 |
| 110 | 5-(2,6-difluorophenyl)-2-(((4-methoxyphenyl)(methyl)amino)methyl-6,7-dihydropyrazolo[1,5-a]pyrazin-4(5H)-one | 398.9 |
| 111 | 2-(((4-methoxyphenyl)(methyl)amino)methyl)-5-(o-tolyl)-6,7-dihydropyrazolo[1,5-a]pyrazin-4(5H)-one | 376.9 |
| 112 | 2-(2-(((4-methoxyphenyl)(methyl)amino)methyl)-4-oxo-6,7-dihydropyrazolo[1,5-a]pyrazin-5(4H)-yl)benzonitrile | 387.9 |
| 113 | 5-(3-methoxyphenyl)-2-(((4-methoxyphenyl)(methyl)amino)methyl-6,7-dihydropyrazolo[1,5-a]pyrazin-4(5H)-one | 392.9 |
| 114 | 5-(4-methoxyphenyl)-2-(((4-methoxyphenyl)(methyl)amino)methyl-6,7-dihydropyrazolo[1,5-a]pyrazin-4(5H)-one | 392.9 |
| 115 | 2-(((4-methoxyphenyl)(methyl)amino)methyl)-5-(2-methylthiazol-4-yl)-6,7-dihydropyrazolo[1,5-a]pyrazin-4(5H)-one | 383.9 |
| 116 | 3-(2-(((4-methoxyphenyl)(methyl)amino)methyl)-4-oxo-6,7-dihydropyrazolo[1,5-a]pyrazin-5(4H)-yl)benzonitrile | 387.9 |
| 117 | 2-(((4-methoxyphenyl)(methyl)amino)methyl)-5-(pyridin-2-yl)-6,7-dihydropyrazolo[1,5-a]pyrazin-4(5H)-one | 363.9 |
| 118 | 4-(2-(((4-methoxyphenyl)(methyl)amino)methyl)-4-oxo-6,7-dihydropyrazolo[1,5-a]pyrazin-5(4H)-yl)benzonitrile | 387.9 |
| 119 | 5-(2-methoxyphenyl)-2-(((4-methoxyphenyl)(methyl)amino)methyl-6,7-dihydropyrazolo[1,5-a]pyrazin-4(5H)-one | 392.9 |
| 120 | 5-(4-(methoxymethyl)phenyl)-2-(((4-methoxyphenyl)(methyl)amino)methyl-6,7-dihydropyrazolo[1,5-a]pyrazin-4(5H)-one | 406.9 |
| 121 | 2-(((4-methoxyphenyl)(methyl)amino)methyl)-5-(pyridin-3-yl)-6,7-dihydropyrazolo[1,5-a]pyrazin-4(5H)-one | 363.9 |
| 122 | 5-(5-fluoropyridin-2-yl)-2-(((4-methoxyphenyl)(methyl)amino)methyl-6,7-dihydropyrazolo[1,5-a]pyrazin-4(5H)-one | 381.9 |
| 123 | 5-(4-(difluoromethoxy)phenyl)-2-(((4-methoxyphenyl)(methyl)amino)methyl-6,7-dihydropyrazolo[1,5-a]pyrazin-4(5H)-one | 428.8 |
| 124 | 5-(5-chloropyridin-2-yl)-2-(((4-methoxyphenyl)(methyl)amino)methyl-6,7-dihydropyrazolo[1,5-a]pyrazin-4(5H)-one | 397.8 |
| 125 | 5-(4-chloro-2-fluorophenyl)-2-(((4-methoxyphenyl)(methyl)amino)methyl-6,7-dihydropyrazolo[1,5-a]pyrazin-4(5H)-one | 415.2 |
| 126 | 5-(2-chloro-3-fluorophenyl)-2-(((4-methoxyphenyl)(methyl)amino)methyl-6,7-dihydropyrazolo[1,5-a]pyrazin-4(5H)-one | 415.2 |
| 127 | 5-(5-chloro-2-fluorophenyl)-2-(((4-methoxyphenyl)(methyl)amino)methyl-6,7-dihydropyrazolo[1,5-a]pyrazin-4(5H)-one | 415.2 |
| 128 | 5-(4-chloro-2,6-difluorophenyl)-2-(((4-methoxyphenyl)(methyl)amino)methyl-6,7-dihydropyrazolo[1,5-a]pyrazin-4(5H)-one | 433.2 |
| 129 | 5-(2-chloro-5-fluorophenyl)-2-(((4-methoxyphenyl)(methyl)amino)methyl-6,7-dihydropyrazolo[1,5-a]pyrazin-4(5H)-one | 415.2 |
| 130 | 5-(2-chloro-4-fluorophenyl)-2-(((4-methoxyphenyl)(methyl)amino)methyl-6,7-dihydropyrazolo[1,5-a]pyrazin-4(5H)-one | 415.2 |
| 131 | 5-(3-chloro-5-fluorophenyl)-2-(((4-methoxyphenyl)(methyl)amino)methyl-6,7-dihydropyrazolo[1,5-a]pyrazin-4(5H)-one | 415.2 |
| 132 | 5-(3-fluoro-5-methoxyphenyl)-2-(((4-methoxyphenyl)(methyl)amino)methyl-6,7-dihydropyrazolo[1,5-a]pyrazin-4(5H)-one | 411.2 |
| 133 | 5-(3-chloro-4-fluorophenyl)-2-(((4-methoxyphenyl)(methyl)amino)methyl-6,7-dihydropyrazolo[1,5-a]pyrazin-4(5H)-one | 415.1 |
| 134 | 5-(3-chloro-5-methoxyphenyl)-2-(((4-methoxyphenyl)(methyl)amino)methyl-6,7-dihydropyrazolo[1,5-a]pyrazin-4(5H)-one | 427.2 |
| 135 | 5-(3-chloro-2-fluorophenyl)-2-(((4-methoxyphenyl)(methyl)amino)methyl-6,7-dihydropyrazolo[1,5-a]pyrazin-4(5H)-one | 415.2 |
| 136 | 5-(4-chloro-3-fluorophenyl)-2-(((4-methoxyphenyl)(methyl)amino)methyl-6,7-dihydropyrazolo[1,5-a]pyrazin-4(5H)-one | 415.2 |
| 137 | 2-(((4-(difluoromethoxy)-2-fluorophenyl)amino)methyl)-5-(5-methylthiazol-2-yl)-6,7-dihydropyrazolo[1,5-a]pyrazin-4(5H)-one | 424.2 |
| 138 | 2-(((4-(difluoromethoxy)-2-fluorophenyl)amino)methyl)-5-(6-fluoropyridin-2-yl)-6,7-dihydropyrazolo[1,5-a]pyrazin-4(5H)-one | 422.2 |
| 139 | 5-(4-chloropyridin-2-yl)-2-(((4-(difluoromethoxy)-2-fluorophenyl)amino)methyl)-6,7-dihydropyrazolo[1,5-a]pyrazin-4(5H)-one | 438.0 |
| 140 | 2-(((4-(difluoromethoxy)-2-fluorophenyl)amino)methyl)-5-(2-methylthiazol-4-yl)-6,7-dihydropyrazolo[1,5-a]pyrazin-4(5H)-one | 424.2 |
| 141 | 2-(((4-(difluoromethoxy)-2-fluorophenyl)amino)methyl)-5-(2,4-difluorophenyl)-6,7-dihydropyrazolo[1,5-a]pyrazin-4(5H)-one | 439.2 |
| 142 | 2-(((4-(difluoromethoxy)-2-fluorophenyl)amino)methyl)-5-(3-methoxyphenyl)-6,7-dihydropyrazolo[1,5-a]pyrazin-4(5H)-one | 433.2 |
| 143 | 2-(((4-(difluoromethoxy)-2-fluorophenyl)amino)methyl)-5-(3-fluoropyridin-2-yl)-6,7-dihydropyrazolo[1,5-a]pyrazin-4(5H)-one | 422.2 |

| No. | Name | ES-MS [M + 1]+ |
|---|---|---|
| 144 | 2-(((4-(difluoromethoxy)-2-fluorophenyl)amino)methyl)-5-(5-methylpyridin-2-yl)-6,7-dihydropyrazolo[1,5-a]pyrazin-4(5H)-one | 418.2 |
| 145 | 2-(((4-(difluoromethoxy)-2-fluorophenyl)amino)methyl)-5-(3,4-difluorophenyl)-6,7-dihydropyrazolo[1,5-a]pyrazin-4(5H)-one | 439.0 |
| 146 | 2-(((4-(difluoromethoxy)-2-fluorophenyl)amino)methyl)-5-(5-fluoropyridin-2-yl)-6,7-dihydropyrazolo[1,5-a]pyrazin-4(5H)-one | 422.2 |
| 147 | 2-(((4-(difluoromethoxy)-2-fluorophenyl)amino)methyl)-5-(3-fluoro-5-methoxyphenyl)-6,7-dihydropyrazolo[1,5-a]pyrazin-4(5H)-one | 451.2 |
| 148 | 5-(5-chloropyridin-2-yl)-2-(((4-(difluoromethoxy)-2-fluorophenyl)amino)methyl)-6,7-dihydropyrazolo[1,5-a]pyrazin-4(5H)-one | 438.2 |
| 149 | 5-(4-chloro-2-fluorophenyl)-2-(((4-(difluoromethoxy)-2-fluorophenyl)amino)methyl)-6,7-dihydropyrazolo[1,5-a]pyrazin-4(5H)-one | 455.0 |
| 150 | 5-(3-chlorophenyl)-2-(((4-(difluoromethoxy)-2-fluorophenyl)amino)methyl)-6,7-dihydropyrazolo[1,5-a]pyrazin-4(5H)-one | 437.0 |
| 151 | 2-(((4-(difluoromethoxy)-2-fluorophenyl)amino)methyl)-5-(pyridin-2-yl)-6,7-dihydropyrazolo[1,5-a]pyrazin-4(5H)-one | 404.2 |
| 152 | 2-(((4-(difluoromethoxy)-2-fluorophenyl)amino)methyl)-5-(3,5-difluorophenyl)-6,7-dihydropyrazolo[1,5-a]pyrazin-4(5H)-one | 439.2 |
| 153 | 2-(((4-(difluoromethoxy)-2-fluorophenyl)amino)methyl)-5-(2-fluorophenyl)-6,7-dihydropyrazolo[1,5-a]pyrazin-4(5H)-one | 421.2 |

Example 9. 2-(((3-Chloropyridin-2-yl)amino)methyl)-5-(4-fluorophenyl)-6,7-dihydropyrazolo[1,5-a]pyrazin-4(5H)-one (154)

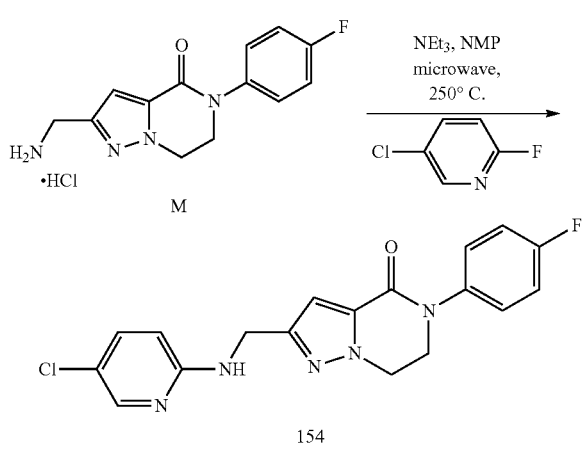

2-(((3-Chloropyridin-2-yl)amino)methyl)-5-(4-fluorophenyl)-6,7-dihydropyrazolo[1,5-a]pyrazin-4(5H)-one (154)

In a microwave vial was combined M (18 mg, 0.062 mmol, 1 eq.), triethylamine (0.172 mL, 1.24 mmol, 20 eq.), 5-chloro-2-fluoropyridine (163 mg, 1.24 mmol, 20 eq.), and NMP (0.60 mL). The reaction was heated under microwave irradiation at 250° C. for 20 minutes. The crude reaction mixture was purified directly on preparative HPLC. Fractions were neutralized with saturated NaHCO$_3$, extracted with EtOAc. dried over Na$_2$SO$_4$, and concentrated under forced air with heat to afford the title compound (5.42 mg, 24% yield) as a white solid. $^1$H NMR (400 MHz, CDCl$_3$) δ 8.04 (d, J=2.5 Hz, 1H), 7.39 (dd, J=8.9, 2.6 Hz, 1H), 7.32-7.28 (m, 2H), 7.11 (t, J=8.3 Hz, 2H), 6.87 (s, 1H), 6.46 (d, J=8.5 Hz, 1H), 5.35 (bs, 1H), 4.50 (d, J=5.6 Hz), 4.51-4.48 (m, 2H), 4.16-4.13 (m, 2H). ES-MS [M+1]$^+$: 356.1.

The following compounds were prepared in an analogous manner:

| No. | Name | ES-MS [M + 1]+ |
|---|---|---|
| 155 | 5-(4-fluorophenyl)-2-(((5-fluoropyridin-2-yl)amino)methyl)-6,7-dihydropyrazolo[1,5-a]pyrazin-4(5H)-one | 356.1 |
| 156 | 5-(4-fluorophenyl)-2-((pyridin-2-ylamino)methyl)-6,7-dihydropyrazolo[1,5-a]pyrazin-4(5H)-one | 338.1 |
| 157 | 5-(4-fluorophenyl)-2-(((6-methylpyridin-2-yl)amino)methyl)-6,7-dihydropyrazolo[1,5-a]pyrazin-4(5H)-one | 352.2 |
| 158 | 2-(((5-chloropyridin-2-yl)amino)methyl)-5-(4-fluorophenyl)-6,7-dihydropyrazolo[1,5-a]pyrazin-4(5H)-one | 372.1 |
| 159 | 5-(4-fluorophenyl)-2-(((5-methylpyridin-2-yl)amino)methyl)-6,7-dihydropyrazolo[1,5-a]pyrazin-4(5H)-one | 351.9 |
| 160 | 5-(4-fluorophenyl)-2-(((3-methylpyridin-2-yl)amino)methyl)-6,7-dihydropyrazolo[1,5-a]pyrazin-4(5H)-one | 351.9 |
| 161 | 5-(4-fluorophenyl)-2-(((4-methylpyridin-2-yl)amino)methyl)-6,7-dihydropyrazolo[1,5-a]pyrazin-4(5H)-one | 351.9 |
| 162 | 5-(4-fluorophenyl)-2-(((3-(trifluoromethyl)pyridin-2-yl)amino)methyl)-6,7-dihydropyrazolo[1,5-a]pyrazin-4(5H)-one | 405.8 |
| 163 | 2-(((6-chloropyridin-2-yl)amino)methyl)-5-(4-fluorophenyl)-6,7-dihydropyrazolo[1,5-a]pyrazin-4(5H)-one | 371.8 |
| 164 | 2-(((4-chloropyridin-2-yl)amino)methyl)-5-(4-fluorophenyl)-6,7-dihydropyrazolo[1,5-a]pyrazin-4(5H)-one | 372.1 |

-continued

| No. | Name | ES-MS [M + 1]⁺ |
|---|---|---|
| 165 | 5-(4-fluorophenyl)-2-(((3-fluoropyridin-2-yl)amino)methyl)-6,7-dihydropyrazolo[1,5-a]pyrazin-4(5H)-one | 356.1 |
| 166 | 5-(4-fluorophenyl)-2-(((6-(trifluoromethyl)pyridin-2-yl)amino)methyl)-6,7-dihydropyrazolo[1,5-a]pyrazin-4(5H)-one | 406.2 |

Example 10. 5-(3,4-Difluorophenyl)-2-(((4-methoxyphenyl)(propyl)amino)methyl)-6,7-dihydropyrazolo[1,5-a]pyrazin-4(5H)-one (167)

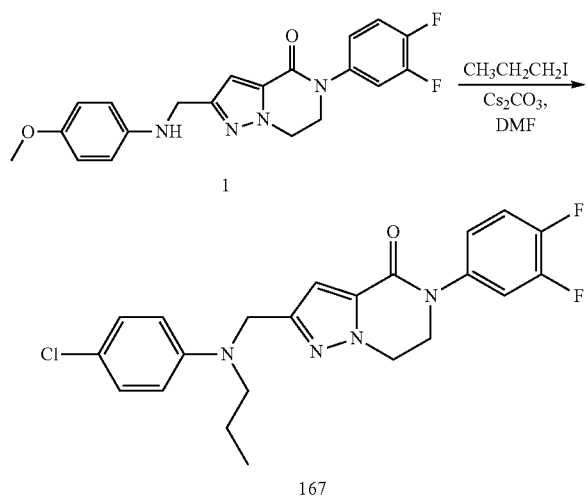

167

5-(3,4-Difluorophenyl)-2-(((4-methoxyphenyl)(propyl)amino)methyl)-6,7-dihydropyrazolo[1,5-a]pyrazin-4(5H)-one (167)

Compound 1 (13.5 mg, 0.04 mmol, 1.00 eq.) was dissolved in DMF (0.23 mL). To this solution Cs₂CO₃ (22.81 mg, 0.07 mmol, 1.75 eq.) and 1-iodopropane (68.31 uL, 0.70 mmol, 20 eq.) were added. The reaction mixture was subjected to microwave irradiation at 120° C. for 15 minutes. The mixture was cooled, diluted with DMSO and filtered through a pad of Celite. Purification using reverse phase HLPC provided the title compound (7.6 mg, 51% yield) as a pale yellow solid. ¹H NMR (400 MHz, CDCl₃) δ 7.27-7.19 (m, 2H), 7.10-7.05 (m, 1H), 6.84-6.78 (m, 5H), 4.53-4.48 (m, 4H), 4.17-4.14 (m, 2H), 3.77 (s, 3H), 3.29 (dd, J=7.6, 7.7 Hz, 2H), 1.63 (sextet, J=7.4 Hz, 2H), 0.95 (t, J=7.4 Hz, 3H). ES-MS [M+1]⁺: 427.2.

The following compound was prepared in an analogous manner:

| No. | Name | ES-MS [M + 1]⁺ |
|---|---|---|
| 168 | 5-(3,4-difluorophenyl)-2-((ethyl(4-methoxyphenyl)amino)methyl)-6,7-dihydropyrazolo[1,5-a]pyrazin-4(5H)-one | 413.2 |

Example 11. 5-(4-Fluorophenyl)-2-(1-((4-methoxyphenyl)amino)ethyl)-6,7-dihydropyrazolo[1,5-a]pyrazin-4(5H)-one (169)

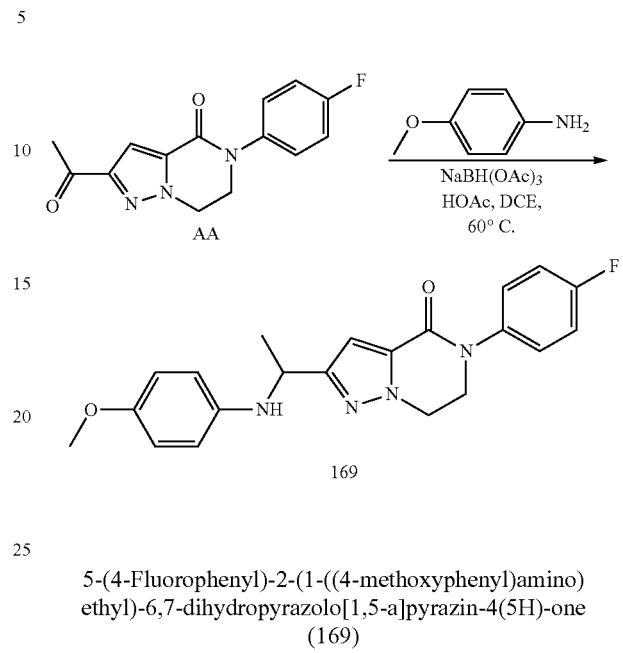

169

5-(4-Fluorophenyl)-2-(1-((4-methoxyphenyl)amino)ethyl)-6,7-dihydropyrazolo[1,5-a]pyrazin-4(5H)-one (169)

P-anisidine (61.6 mg, 0.50 mmol, 10.0 eq.) was added to a solution of compound AA (13.7 mg, 0.05 mmol, 1.00 eq.) in DCE (0.17 mL) and acetic acid (0.25 mL). The mixture was stirred at 60° C. for 30 min and sodium triacetoxyborohydride (15.9 mg, 0.08 mmol, 1.50 eq.) was added. After 10 min, the mixture was diluted with DCM (2.0 mL) and poured into a saturated aqueous NaHCO₃ (2.0 mL). The layers were separated. The aqueous layer was extracted with DCM (3×). The combined organic extracts were washed with brine, dried over Na₂SO₄ and concentrated in vacuo. Purification of the residue using reverse phase HLPC gave the title compound (3.7 mg, 19% yield) as a yellow solid. ¹H NMR (400 MHz, CDCl₃) δ 7.34-7.28 (m, 2H), 7.16-7.12 (m, 2H), 6.90-6.85 (m, 3H), 6.64-6.60 (m, 2H), 4.68-4.63 (m, 1H), 4.53-4.49 (m, 2H), 4.18-4.15 (m, 2H), 2.36 (bs, 1H), 1.59 (d, J=6.7 Hz, 3H). ES-MS [M+1]⁺: 381.1.

The following compounds were prepared in an analogous manner:

| No. | Name | ES-MS [M + 1]⁺ |
|---|---|---|
| 170 | 5-(4-fluorophenyl)-2-(1-(phenylamino)ethyl)-6,7-dihydropyrazolo[1,5-a]pyrazin-4(5H)-one | 351.2 |
| 171 | 5-(4-fluorophenyl)-2-(1-((4-fluorophenyl)amino)ethyl)-6,7-dihydropyrazolo[1,5-a]pyrazin-4(5H)-one | 369.2 |
| 172 | 2-(1-((4-chlorophenyl)amino)ethyl)-5-(4-fluorophenyl)-6,7-dihydropyrazolo[1,5-a]pyrazin-4(5H)-one | 385.1 |

Example 12. Biological Activity

A. mGlu$_3$ Ca$^{2+}$ Flux Assay

G$_{\alpha15}$/TREx cells stably expressing rat mGlu$_3$ were plated in black-walled, clear-bottomed, poly-D-lysine coated 384-well plates in 20 µL of assay medium (DMEM containing 10% dialyzed FBS, 20 mM HEPES, 25 ng/mL tetracycline, 100 units/mL penicillin/streptomycin plus 250 ng/mL Fungizone, and 1 mM sodium pyruvate) at a density of 15K cells/well. The cells were grown overnight at 37° C. in the presence of 5% CO$_2$. The next day, medium was removed and the cells incubated with 20 µL of 2.3 µM Fluo-4, AM prepared as a 2.3 mM stock in DMSO and mixed in a 1:1 ratio with 10% (w/v) pluronic acid F-127 and diluted in assay buffer (Hank's balanced salt solution, 20 mM HEPES, and 2.5 mM probenecid) for 60 minutes at room temperature. Dye was removed, 20 µL of assay buffer was added, and the plate was incubated for 10 minutes at room temperature.

Ca$^{2+}$ flux was measured using the Functional Drug Screening System (FDSS7000, Hamamatsu, Japan). After establishment of a fluorescence baseline for about 3 seconds, the compounds of the present invention were added to the cells, and the response in cells was measured. 2.3 minutes later an EC$_{20}$ concentration of the mGlu$_3$ receptor agonist glutamate was added to the cells, and the response of the cells was measured for 1.9 minutes; an EC$_{80}$ concentration of agonist was added and readings taken for an additional 1.7 minutes. All test compounds were dissolved and diluted to a concentration of 10 mM in 100% DMSO. Compounds were then serially diluted 1:3 in DMSO into 10 point concentration response curves, transferred to daughter plates, and further diluted into assay buffer to a 2× stock. Calcium fluorescence measures were recorded as fold over basal fluorescence; raw data was then normalized to the maximal response to glutamate. Antagonism of the agonist response of the mGlu$_3$ receptor in the present invention was observed as a decrease in response to nearly maximal concentrations of glutamate in the presence of compound compared to the response to glutamate in the absence of compound.

The raw data file containing all time points was used as the data source in the analysis template. This was saved by the FDSS as a tab-delimited text file. Data were normalized using a static ratio function (F/F$_0$) for each measurement of the total 360 values per well divided by each well's initial value. Data were then reduced to peak amplitudes (Max−Initial Min) using a time range that starts approximately 3 seconds prior to the glutamate EC$_{80}$ addition and continues for approximately 90 seconds. This is sufficient time to capture the peak amplitude of the cellular calcium response. Individual amplitudes were expressed as % E$_{Max}$ by multiplying each amplitude by 100 and then dividing the product by the mean of the amplitudes derived from the glutamate EC$_{Max}$-treated wells. EC$_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly.

A compound was designated as a negative allosteric modulator (NAM) if the compound showed a concentration-dependent decrease in the glutamate EC$_{80}$ addition. For NAMs, potency (IC$_{50}$) and maximum response (% Glu Max), i.e. the amplitude of response in the presence of 30 µM test compound as a percentage of the maximal response to glutamate, are reported. For NAMs that show a decrease in the EC$_{80}$ response, but do not hit a plateau, the average of the maximum response at a single concentration (30 µM) was determined (% Glu Max) and potencies were reported as ">10,000 nM". Compounds with no measurable activity are designated as ">30,000 nM" since the top concentration of compound tested in the assay is 30 µM.

B. mGlu$_5$ Ca$^{2+}$ Flux Assay

HEK 293A cells stably expressing rat mGlu$_5$ were plated in black-walled, clear-bottomed, poly-D-lysine coated 384-well plates in 20 µL of assay medium (DMEM containing 10% dialyzed FBS, 20 mM HEPES, 100 units/mL penicillin/streptomycin plus 250 ng/mL Fungizone, and 1 mM sodium pyruvate) at a density of 20K cells/well. The cells were grown overnight at 37° C. in the presence of 5% CO$_2$. The next day, medium was removed and the cells incubated with 20 µL of 2.3 µM Fluo-4, AM prepared as a 2.3 mM stock in DMSO and mixed in a 1:1 ratio with 10% (w/v) pluronic acid F-127 and diluted in assay buffer (Hank's balanced salt solution, 20 mM HEPES, and 2.5 mM probenecid) for 45 minutes at 37° C. Dye was removed, 20 µL of assay buffer was added, and the plate was incubated for 5 minutes at room temperature.

Ca$^{2+}$ flux was measured using the Functional Drug Screening System (FDSS7000, Hamamatsu, Japan). After establishment of a fluorescence baseline for about 3 seconds, the compounds of the present invention were added to the cells, and the response in cells was measured. 2.3 minutes later an EC$_{20}$ concentration of the mGlu$_5$ receptor agonist glutamate was added to the cells, and the response of the cells was measured for 1.9 minutes; an EC$_{80}$ concentration of agonist was added and readings taken for an additional 1.7 minutes. All test compounds were dissolved and diluted to a concentration of 10 mM in 100% DMSO. Compounds were then serially diluted 1:3 in DMSO into 10 point concentration response curves, transferred to daughter plates, and further diluted into assay buffer to a 2× stock. Calcium fluorescence measures were recorded as fold over basal fluorescence; raw data was then normalized to the maximal response to glutamate. Potentiation of the agonist response of the mGlu$_5$ receptor in the present invention was observed as an increase in response to submaximal concentrations of glutamate in the presence of compound compared to the response to glutamate in the absence of compound. Antagonism of the agonist response of the mGlu$_5$ receptor in the present invention was observed as a decrease in response to nearly maximal concentrations of glutamate in the presence of compound compared to the response to glutamate in the absence of compound.

The raw data file containing all time points was used as the data source in the analysis template. This was saved by the FDSS as a tab-delimited text file. Data were normalized using a static ratio function (F/F$_0$) for each measurement of the total 360 values per well divided by each well's initial value. Data were then reduced to peak amplitudes (Max−Initial Min) using a time range that starts approximately 3 seconds prior to the glutamate EC$_{20}$/EC$_{80}$ addition and continues for approximately 90-120 seconds. This is sufficient time to capture the peak amplitude of the cellular calcium response. Individual amplitudes were expressed as % E$_{Max}$ by multiplying each amplitude by 100 and then dividing the product by the mean of the amplitudes derived from the glutamate EC$_{Max}$-treated wells. EC$_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly.

A compound was designated as a positive allosteric modulator (PAM) if the compound showed a concentration-dependent increase in the glutamate $EC_{20}$ addition. For PAMs, potency ($EC_{50}$) and maximum response (% Glu Max), i.e. the amplitude of response in the presence of 30 μM test compound as a percentage of the maximal response to glutamate, are reported. For PAMs that show an increase in the $EC_{20}$ response, but do not hit a plateau, the average of the maximum response at a single concentration (30 μM) was determined (% Glu Max) and potencies were reported as ">10,000 nM". A compound was designated as a negative allosteric modulator (NAM) if the compound showed a concentration-dependent decrease in the glutamate $EC_{80}$ addition. For NAMs, potency ($IC_{50}$) and maximum response (% Glu Max), i.e. the amplitude of response in the presence of 30 μM test compound as a percentage of the maximal response to glutamate, are reported. For NAMs that show a decrease in the $EC_{80}$ response, but do not hit a plateau, the average of the maximum response at a single concentration (30 μM) was determined (% Glu Max) and potencies were reported as ">10,000 nM". Compounds with no measurable activity are designated as ">30,000 nM" since the top concentration of compound tested in the assay is 30 μM.

C. Results and Discussion of Biological Activity Data

The results of these assays are shown in Table 1. The data in Table 1 demonstrates that the disclosed compounds are negative allosteric modulators of mGlu$_3$ and show high affinity for the mGlu$_3$ receptor(s). Data is from a single experiment unless otherwise noted. Data that is an average of two experiments is noted as "n=2" while data that is an average of three or more experiments is presented as the average plus or minus the standard error of the mean.

In addition, Table 1 demonstrates that the compounds have an unexpectedly high affinity for the mGlu$_3$ receptor as compared to the mGlu$_5$ receptor. Preferred compounds demonstrate high selectivity for mGlu$_3$ (>5:1), and many show selectivity of >20:1 for mGlu$_3$ over mGlu$_5$. Compounds with measurable activity at mGlu$_5$ are positive allosteric modulators (PAMs) of that receptor unless otherwise noted as negative allosteric modulators (NAM) or partial antagonists (PAnt). Partial antagonists (PAnt) display concentration-response curves (CRCs) that plateau above 10%.

TABLE 1

| Compound | rat mGlu$_3$ IC$_{50}$ (nM) | rat mGlu$_3$ Glu max (%) | rat mGlu$_5$ EC$_{50}$ or IC$_{50}$ (nM) | rat mGlu$_5$ Glu max (%) | Fold selectivity (mGlu$_3$ vs. mGlu$_5$) |
|---|---|---|---|---|---|
| 1 | 1470 | 4.04 | >30,000 | N/A | >20 |
| 2 | 1320 | 1.99 | 2040 | 98.32 | 1.55 |
| 3 | 944 | 1.73 | 2470 | 95.68 | 2.62 |
| 4 | 2390 | 2.62 | >10,000 | 42.18 | >4.1 |
| 5 | 1270 | 2.08 | 2190 | 65.44 | 1.72 |
| 6 | 3040 | 0.98 | >30,000 | N/A | >9.8 |
| 7 | 1040 | 1.28 | 2210 | 99.00 | 2.13 |
| 8 | 1350 | 2.85 | 5960 | 79.40 | 4.41 |
| 9 | 1210 | 2.95 | 3320 | 82.81 | 2.74 |
| 10 | 1780 | 2.01 | >30,000 | N/A | >16 |
| 11 | 1250 | 1.48 | >30,000 | N/A | >24 |
| 12 | 505 | 1.31 | 7330 | 85.56 | 14.51 |
| 13 | 1150 | 2.22 | 3260 | 56.63 | 2.83 |
| 14 | 1540 | −11.77 | >30,000 | N/A | >19 |
| 15 | N/A | | | N/A | |
| 16 | >30,000 | N/A | >30,000 | N/A | N/A |
| 17 | 2120 | 1.55 | >30,000 | N/A | >14 |
| 18 | 4780 | 1.71 | >30,000 | N/A | >6.2 |
| 19 | >30,000 | N/A | >30,000 | N/A | N/A |
| 20 | 709 (n = 2) | 2.90 (n = 2) | >30,000 | N/A | >42 |
| 21 | >10,000 | 13.32 | >30,000 | N/A | >3 |
| 22 | 1550 | −10.97 | >30,000 | N/A | >19 |
| 23 | >10,000 | 28.92 | >30,000 | N/A | >3 |
| 24 | >30,000 | N/A | >30,000 | N/A | N/A |
| 25 | >10,000 | 66.86 | >30,000 | N/A | >3 |
| 26 | 890 | 1.01 | >30,000 | N/A | >33 |
| 27 | 586 | 2.82 | 2380 | 90.81 | 4.06 |
| 28 | 1250 | 1.76 | 1510 | 80.61 | 1.21 |
| 29 | 508 | 2.45 | 1640 | 87.47 | 3.23 |
| 30 | 738 | 2.71 | 6440 | 101.92 | 8.73 |
| 31 | 462 | 2.02 | 2480 | 75.79 | 5.37 |
| 32 | 1050 | 1.25 | 8830 | 84.10 | 8.41 |
| 33 | 1270 | 1.82 | 1110 | 89.73 | 0.87 |
| 34 | 856 (n = 2) | 3.18 (n = 2) | >30,000 | N/A | >35 |
| 35 | 799 | 1.68 | 4770 | 97.36 | 5.97 |
| 36 | 1670 | 1.91 | >30,000 | N/A | >17 |
| 37 | 334 | 2.57 | >10,000 | 38.38 | >29 |
| 38 | 489 | 2.28 | 1560 | 84.73 | 3.19 |
| 39 | 2880 | 1.95 | >10,000 | 75.73 | >3.4 |
| 40 | 1380 | 5.15 | 4810 | 34.43 | 3.49 |
| 41 | 8110 | −2.27 | 1360 | 81.72 | 0.17 |
| 42 | 871 | 0.89 | >10,000 | 71.42 | >11 |
| 43 | 2540 | 1.61 | 5230 | 90.64 | 2.06 |
| 44 | 2670 | −0.26 | >10,000 | 23.89 | >3.7 |
| 45 | 3340 | 1.32 | >10,000 | 37.12 | >2.9 |
| 46 | 1210 | 0.58 | >10,000 | 24.55 | >8.2 |
| 47 | 1840 | 1.77 | 1070 | 78.29 | 0.58 |
| 48 | 1650 | 1.63 | >10,000 | 88.84 | >6.0 |
| 49 | 1330 | −0.54 | 5920 | 76.51 | 4.45 |
| 50 | 3050 | 0.09 | >30,000 | N/A | >9.8 |
| 51 | 3010 | 3.21 | 7610 | 86.24 | 2.53 |
| 52 | 2720 | 4.06 | >30,000 | N/A | >11 |
| 53 | 10,000 | 8.62 | >30,000 | N/A | >3.0 |
| 54 | 2040 | 3.56 | >10,000 (NAM) | 36.00 | >4.9 |
| 55 | 1670 | 1.85 | >10,000 | 28.82 | >5.9 |
| 56 | 1160 | 2.97 | >30,000 | N/A | >25 |
| 57 | 2320 | 0.96 | 5530 | 56.67 | 2.38 |
| 58 | 1830 | 1.27 | >30,000 | N/A | >16 |
| 59 | 1740 | 3.14 | >10,000 | 48.91 | >5.7 |
| 60 | 1250 | 0.56 | >10,000 | 31.49 | >8.0 |
| 61 | 1310 | 2.22 | 6150 | 80.27 | 4.69 |
| 62 | 2990 | 0.79 | >30,000 | N/A | >10 |
| 63 | 8370 | −0.60 | >30,000 | N/A | >3.5 |
| 64 | 1350 | 2.46 | >30,000 | N/A | >22 |
| 65 | 1340 | 2.16 | >30,000 | N/A | >22 |
| 66 | 1460 | 0.95 | >30,000 | N/A | >20 |
| 67 | 2560 | 1.96 | >30,000 | N/A | >11 |
| 68 | 1230 | 2.68 | >10,000 | 53.20 | >8.1 |
| 69 | 2220 | 2.19 | 5750 | 89.11 | 2.59 |
| 70 | 1140 | 2.67 | >10,000 | 57.49 | >8.7 |
| 71 | 1310 | 1.60 | 9600 | 76.58 | 7.33 |
| 72 | 1920 | 4.10 | >10,000 | 59.88 | >5.2 |
| 73 | 10,000 | 4.07 | >10,000 | 63.85 | >1.0 |
| 74 | 2350 | −2.19 | >10,000 | 59.29 | >4.2 |
| 75 | 771 | 2.66 | 5830 | 85.61 | 7.56 |
| 76 | 1170 | 0.35 | 8190 | 86.07 | 7.00 |
| 77 | 1570 | 3.77 | >30,000 | N/A | >19 |
| 78 | 1170 | 1.23 | >10,000 | 61.60 | >8.5 |
| 79 | 1280 | 1.49 | >10,000 | 39.98 | >7.8 |
| 80 | 4320 | −0.58 | 7750 | 95.82 | 1.79 |
| 81 | 1360 | 15.40 | >30,000 | N/A | >22 |
| 82 | 1220 (n = 2) | 1.01 (n = 2) | >30,000 | N/A | >24 |
| 83 | 876 | −0.98 | >30,000 | N/A | >34 |
| 84 | 1860 | 0.82 | >10,000 (NAM) | 73.44 | >5.3 |
| 85 | 9480 | −7.96 | >30,000 | N/A | >3.1 |
| 86 | 594 | 1.68 | 7760 | 109.92 | 13.06 |
| 87 | 805 | 0.71 | >10,000 | 41.88 | >12 |
| 88 | 1020 | 0.55 | >30,000 | N/A | >29 |
| 89 | 467 | 1.29 | >30,000 | N/A | >64 |

TABLE 1-continued

| Compound | rat mGlu$_3$ IC$_{50}$ (nM) | rat mGlu$_3$ Glu max (%) | rat mGlu$_5$ EC$_{50}$ or IC$_{50}$ (nM) | rat mGlu$_5$ Glu max (%) | Fold selectivity (mGlu$_3$ vs. mGlu$_5$) |
|---|---|---|---|---|---|
| 90 | 885 | 1.40 | 4500 | 87.35 | 5.08 |
| 91 | 592 | 2.53 | >30,000 | N/A | >50 |
| 92 | 986 | 1.39 | >30,000 | N/A | >30 |
| 93 | 1130 | 1.47 | >10,000 | 57.16 | >8.8 |
| 94 | 660 | 1.58 | >10,000 | 29.92 | >15 |
| 95 | 588 | 3.43 | >10,000 | 31.08 | >17 |
| 96 | 585 | 1.61 | >30,000 | N/A | >51 |
| 97 | 1080 ± 240 | 1.74 ± 0.56 (n = 2) | >30,000 | N/A | >27 |
| 98 | 668 | 1.53 | >30,000 | N/A | >44 |
| 99 | 675 | 1.20 | >30,000 | N/A | >44 |
| 100 | 777 | 1.80 | >30,000 | N/A | >38 |
| 101 | 783 | 1.57 | >30,000 | N/A | >38 |
| 102 | 801 | 1.68 | >30,000 | N/A | >37 |
| 103 | 805 | 1.16 | >30,000 | N/A | >37 |
| 104 | 856 | 1.30 | >30,000 | N/A | >35 |
| 105 | 871 | 2.05 | >30,000 | N/A | >34 |
| 106 | 1020 | 0.79 | >30,000 | N/A | >29 |
| 107 | 1030 | 1.67 | >30,000 | N/A | >29 |
| 108 | 1250 | 0.97 | >30,000 | N/A | >24 |
| 109 | 1320 | 2.13 | >30,000 | N/A | >22 |
| 110 | 1640 | 1.75 | >30,000 | N/A | >18 |
| 111 | 2000 | 0.74 | >30,000 | N/A | >15 |
| 112 | 3790 | 1.10 | >30,000 | N/A | >7.9 |
| 113 | 1120 | 0.70 | >30,000 | N/A | >26 |
| 114 | 1370 | 1.70 | >30,000 | N/A | >21 |
| 115 | 1620 | 3.88 | >30,000 | N/A | >18 |
| 116 | 2210 | 1.55 | >30,000 | N/A | >13 |
| 117 | 2730 | 1.59 | >30,000 | N/A | >10 |
| 118 | 1970 | 1.63 | >30,000 | N/A | >15 |
| 119 | 3280 | 1.30 | >30,000 | N/A | >9.1 |
| 120 | 2880 | 1.48 | >30,000 | N/A | >10 |
| 121 | 4690 | 0.66 | >30,000 | N/A | >6.3 |
| 122 | 1140 | 1.40 | >30,000 | N/A | >26 |
| 123 | 1030 | 0.30 | >30,000 | N/A | >29 |
| 124 | 917 (n = 2) | 1.64 (n = 2) | >30,000 (n = 2) | N/A | >32 |
| 125 | 1380 | 1.47 | >30,000 | N/A | >21 |
| 126 | 1600 | 1.50 | >10,000 (NAM) | 56.75 | >6.2 |
| 127 | 1260 | 2.32 | >10,000 (NAM) | 54.64 | >7.9 |
| 128 | 1860 | 1.80 | >30,000 | N/A | >16 |
| 129 | 2020 | 2.02 | >30,000 | N/A | >14 |
| 130 | 1950 | 2.05 | >30,000 | N/A | >15 |
| 131 | 1370 | 1.95 | >30,000 | N/A | >21 |
| 132 | 1340 | 1.50 | >30,000 | N/A | >22 |
| 133 | 1210 | 2.13 | >30,000 | N/A | >24 |
| 134 | 1710 | 1.77 | >30,000 | N/A | >17 |
| 135 | 1210 | 7.26 | >30,000 | N/A | >24 |
| 136 | 1270 | 2.43 | >30,000 | N/A | >23 |
| 137 | >30,000 | N/A | >30,000 | N/A | N/A |
| 138 | 821 | 2.05 | >30,000 | N/A | >36 |
| 139 | 1760 | 2.59 | >30,000 | N/A | >17 |
| 140 | 624 | 2.43 | >30,000 | N/A | >48 |
| 141 | 706 | 1.87 | >30,000 | N/A | >42 |
| 142 | 863 | 1.50 | >30,000 | N/A | >34 |
| 143 | 950 | 1.31 | >30,000 | N/A | >31 |
| 144 | 1740 | 5.68 | >30,000 | N/A | >17 |
| 145 | 800 | 2.55 | >30,000 | N/A | >37 |
| 146 | 578 | 2.03 | >30,000 | N/A | >51 |
| 147 | 1260 | 1.67 | >30,000 | N/A | >23 |
| 148 | 930 | 3.97 | >30,000 | N/A | >32 |
| 149 | >10,000 | 25.78 | >30,000 | N/A | >3 |
| 150 | 1390 | 2.97 | >30,000 | N/A | >21 |
| 151 | 943 | 1.14 | >30,000 | N/A | >31 |
| 152 | 1070 | 2.23 | >30,000 | N/A | >28 |
| 153 | 772 | 2.29 | >30,000 | N/A | >38 |
| 154 | 1340 | 3.27 | >30,000 | N/A | >22 |
| 155 | 1460 | 1.50 | >10,000 (NAM) | 11.29 | >6.8 |
| 156 | 3190 | −1.17 | >10,000 (NAM) | 49.09 | >3.1 |
| 157 | 3210 | −0.19 | >30,000 | N/A | >9.3 |
| 158 | 602 | 1.27 | 2420 (PAnt) | 73.61 | 4.02 |
| 159 | 1770 (n = 2) | 0.86 (n = 2) | >30,000 | N/A | >16 |
| 160 | 4700 (n = 2) | 0.18 (n = 2) | >30,000 | N/A | >6.3 |
| 161 | 3750 (n = 2) | 1.14 (n = 2) | >30,000 | N/A | >8.0 |
| 162 | 3840 (n = 2) | 0.79 (n = 2) | >30,000 | N/A | >7.8 |
| 163 | 1180 (n = 2) | 1.15 (n = 2) | >30,000 | N/A | >25 |
| 164 | 1320 | 2.99 | >10,000 | 35.30 | >7.5 |
| 165 | 2110 | 1.66 | >30,000 | N/A | >14 |
| 166 | 2350 | 2.06 | >10,000 | 50.59 | >4.2 |
| 167 | 3720 | 1.32 | >30,000 | N/A | 8.06 |
| 168 | 2120 | 1.95 | >30,000 | N/A | >14 |
| 169 | 7740 | −6.64 | >30,000 | N/A | >3.8 |
| 170 | 2850 | 0.67 | >30,000 | N/A | >10 |
| 171 | 2150 | 0.39 | >30,000 | N/A | >13 |
| 172 | 1550 | 1.29 | >30,000 | N/A | >19 |

Obtaining selectivity over other mGlu receptors, such as mGlu$_5$, is beneficial because the selective mGlu$_3$ modulator will have only the intended biological effect of modulating the mGlu$_3$ receptor in vivo, without the off-target effects of modulating the mGlu$_5$ receptor. As a result diseases and/or disorders associated exclusively with the mGlu$_3$ receptor may be treated.

Compounds shown in Table 2 where X=O showed dual activity as positive allosteric modulators of mGlu$_5$ and negative allosteric modulators of mGlu$_3$. These compounds showed no selectivity for either receptor, as they are equipotent against the mGlu$_3$ and mGlu$_5$ receptors. However, compounds of formula (I), such as when X=NH (shown in Table 2), displayed a higher affinity for mGlu$_3$ than mGlu$_5$. When X=NMe (shown in Table 2), an even greater difference in affinity for mGlu$_3$ over mGlu$_5$ is observed. In fact, selectivity in this subset of compounds, where X=NMe, ranges from 13:1 to greater than 64:1.

By replacing the oxygen with an amino group, disclosed compounds show an unexpected loss in affinity for the mGlu$_5$ receptor, resulting in the advantageous effect of modulation of the mGlu$_3$ that could not have been predicted. The consequences of this advantageous effect are the possession of compounds that are selective negative allosteric modulators of the mGlu$_3$ receptor, resulting in the ability to treat diseases and/or disorders associated with the mGlu$_3$ receptor, without the risk of off-target effects associated with non-selective modulators. Selective negative allosteric modulators will also help in fully understanding and determining the role of mGlu$_3$ in the pathology of diseases and/or disorders associated with mGlu$_3$.

TABLE 2

| Compound Structure | X = O | | X = NH | | X = NMe | |
|---|---|---|---|---|---|---|
| | mGlu$_3$ IC$_{50}$* (Glu max) | mGlu$_5$ EC$_{50}$* (Glu max) | mGlu$_3$ IC$_{50}$* (Glu max) | mGlu$_5$ EC$_{50}$* (Glu max) | mGlu$_3$ IC$_{50}$* (Glu max) | mGlu$_5$ EC$_{50}$* (Glu max) |
| (structure 1) | 278 (2%) | 44 (79%) | 1320 (2%) | 2040 (98%) | 1220 (1%) | >30,000 (N/A) |
| (structure 2) | 264 (2%) | 147 (61%) | 944 (2%) | 2470 (96%) | 876 (−1%) | >30,000 (N/A) |
| (structure 3) | 132 (1%) | 192 (69%) | 1040 (1%) | 2210 (99%) | 594 (2%) | 7760 (110%) |
| (structure 4) | 108 (1%) | 106 (71%) | 1150 (2%) | N/A | 467 (1%) | >30,000 (N/A) |

*IC$_{50}$ and EC$_{50}$ values are in nM

Selectivity versus other mGlus can also be assessed by evaluating the effect of a single concentration of compound on the glutamate concentration-response curve (CRC) in cell lines expressing the mGlu of interest. Such selectivity assays are described in the literature (Noetzel, M. J. et al. *Mol. Pharmacol.* 2012, 81, 120.) Compounds 26 and 92 were tested at 10 µM in such assays and determined to be inactive at that concentration against mGlu$_1$, mGlu$_2$, mGlu$_4$, mGlu$_6$, mGlu$_7$, and mGlu$_8$.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (I)

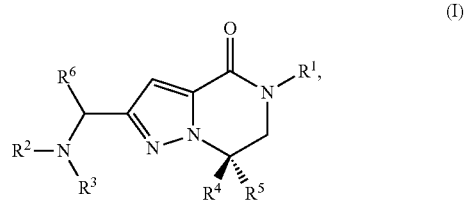

or a pharmaceutically acceptable salt thereof, wherein

R$^1$ is selected from the group consisting of aryl and heteroaryl, each optionally substituted with one to three substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl;

R$^2$ is selected from the group consisting of phenyl and pyridinyl, each optionally substituted with one to five substituents independently selected from halogen, cyano, alkyl, fluoroalkyl, alkyloxy, fluoroalkyloxy, hydroxyalkyl, hydroxyfluoroalkyl, alkoxyalkyl, alkoxyfluoroalkyl, cyanoalkyl, and cyanofluoroalkyl, wherein two of the substituents on adjacent carbons can together form a 5 or 6 membered ring;

$R^3$ is selected from the group consisting of hydrogen, $C_1$-$C_3$ alkyl, and $C_1$-$C_3$ fluoroalkyl;

$R^4$ and $R^5$ are each independently selected from the group consisting of hydrogen and $C_1$-$C_3$ alkyl; and $R^6$ is selected from the group consisting of hydrogen, $C_1$-$C_3$ alkyl, and $C_1$-$C_3$ fluoroalkyl.

2. The compound of claim 1, wherein:
$R^1$ is aryl, optionally substituted with one, two or three halogens;
$R^2$ is phenyl, optionally substituted with one, two, three, four or five substituents independently selected from halogen and alkyloxy; and
$R^6$ is $C_1$-$C_3$ alkyl.

3. The compound of claim 1, wherein
$R^2$ is selected from the group consisting of phenyl and pyridinyl, each optionally substituted with one to five substituents independently selected from halogen, cyano, alkyloxy, fluoroalkyloxy, hydroxyalkyl, hydroxyfluoroalkyl, alkoxyalkyl, alkoxyfluoroalkyl, cyanoalkyl, and cyanofluoroalkyl;
$R^3$ is selected from the group consisting of $C_1$-$C_3$ alkyl and $C_1$-$C_3$ fluoroalkyl; and
$R^6$ is hydrogen.

4. The compound of claim 1, wherein
$R^3$ is hydrogen;
$R^4$ is $C_1$-$C_3$ alkyl;
$R^5$ is hydrogen; and
$R^6$ is hydrogen.

5. The compound of claim 1, wherein
$R^3$ is hydrogen;
$R^4$ is hydrogen;
$R^5$ is hydrogen; and
$R^6$ is hydrogen.

6. The compound of claim 1, wherein
$R^3$ is hydrogen;
$R^4$ is hydrogen;
$R^5$ is hydrogen; and
$R^6$ is selected from the group consisting of $C_1$-$C_3$ alkyl and $C_1$-$C_3$ fluoroalkyl.

7. The compound of claim 1, wherein
$R^2$ is

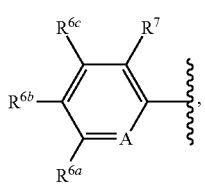

wherein
A is selected from the group consisting of N, CH, and CF;
$R^{6a}$, $R^{6b}$, and $R^{6c}$ are independently selected from the group consisting of hydrogen, fluoro, chloro, bromo, cyano, methyl, methoxy, difluoromethoxy, —$CR^8R^9OH$, —$CR^8R^9OCH_3$, and —$CR^8R^9CN$; wherein $R^8$ and $R^9$ are each independently selected from hydrogen, fluoro, and methyl; and $R^7$ is selected from the group consisting of hydrogen, fluoro, and chloro.

8. The compound of claim 1, wherein
$R^2$ is

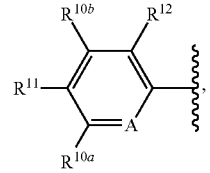

wherein
A is selected from the group consisting of N, CH, and CF;
$R^{10a}$ and $R^{10b}$ are independently selected from the group consisting of hydrogen, fluoro, chloro, cyano, methyl, and methoxy;
$R^{11}$ is selected from the group consisting of hydrogen, fluoro, chloro, cyano, methyl, ethyl, methoxy, difluoromethoxy, —$CR^{13}R^{14}OH$, —$CR^{13}R^{14}OCH_3$, and —$CR^{13}R^{14}CN$; wherein $R^{13}$ and $R^{14}$ are each independently selected from hydrogen, fluoro, and methyl;
$R^{12}$ is selected from the group consisting of hydrogen, fluoro, and chloro; and
$R^4$ is methyl;
provided that $R^2$ is not unsubstituted phenyl or unsubstituted pyridinyl.

9. The compound of claim 1, wherein
$R^2$ is selected from the group consisting of:

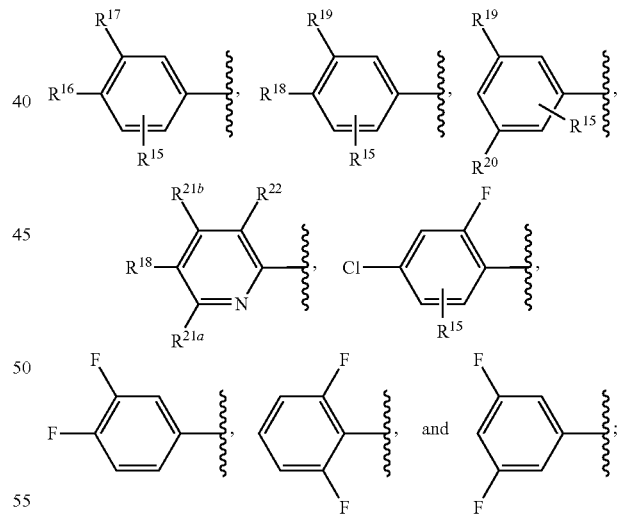

wherein
$R^{15}$ is selected from the group consisting of hydrogen and fluoro;
$R^{16}$ is selected from the group consisting of cyano, methyl, ethyl, methoxy, difluoromethoxy, —$CR^{23}R^{24}OH$, —$CR^{23}R^{24}OCH_3$, and —$CR^{23}R^{24}CN$;
$R^{17}$ is selected from the group consisting of hydrogen, fluoro, cyano, methyl, methoxy, and difluoromethoxy;

R$^{18}$ is selected from the group consisting of hydrogen, fluoro, cyano, methyl, ethyl, methoxy, difluoromethoxy, —CR$^{23}$R$^{24}$OH, —CR$^{23}$R$^{24}$OCH$_3$, and —CR$^{23}$R$^{24}$CN;

R$^{19}$ is selected from the group consisting of cyano, methyl, ethyl, methoxy, difluoromethoxy, —CR$^{23}$R$^{24}$OH, —CR$^{23}$R$^{24}$OCH$_3$, and —CR$^{23}$R$^{24}$CN;

R$^{20}$ is selected from the group consisting of hydrogen, fluoro, chloro, cyano, methyl, ethyl, methoxy, difluoromethoxy, —CR$^{23}$R$^{24}$OH, —CR$^{23}$R$^{24}$OCH$_3$, and —CR$^{23}$R$^{24}$CN;

R$^{21a}$ and R$^{21b}$ are independently selected from the group consisting of hydrogen, fluoro, chloro, cyano, methyl, methoxy, difluoromethoxy, —CR$^{23}$R$^{24}$OH, —CR$^{23}$R$^{24}$OCH$_3$, and —CR$^{23}$R$^{24}$CN; and R$^{22}$ is selected from the group consisting of hydrogen, fluoro, and chloro;

wherein R$^{23}$ and R$^{24}$ are independently selected from the group consisting of hydrogen, fluoro, and methyl;

provided that R$^2$ is not unsubstituted pyridinyl, 3-methylphenyl, or 4-(difluoromethoxy)-3-fluorophenyl.

10. The compound of claim 1, or a pharmaceutically acceptable salt thereof, selected from the group consisting of:

5-(4-fluorophenyl)-2-((methyl(phenyl)amino)methyl)-6,7-dihydropyrazolo[1,5-a]pyrazin-4(5H)-one;

5-(4-fluorophenyl)-2-(((2-fluorophenyl)(methyl)amino)methyl)-6,7-dihydropyrazolo[1,5-a]pyrazin-4(5H)-one;

2-(((2-chlorophenyl)(methyl)amino)methyl)-5-(4-fluorophenyl)-6,7-dihydropyrazolo[1,5-a]pyrazin-4(5H)-one;

5-(4-fluorophenyl)-2-(((2-methoxyphenyl)(methyl)amino)methyl)-6,7-dihydropyrazolo[1,5-a]pyrazin-4(5H)-one;

5-(4-fluorophenyl)-2-(((3-fluorophenyl)(methyl)amino)methyl)-6,7-dihydropyrazolo[1,5-a]pyrazin-4(5H)-one;

2-(((3-chlorophenyl)(methyl)amino)methyl)-5-(4-fluorophenyl)-6,7-dihydropyrazolo[1,5-a]pyrazin-4(5H)-one;

5-(4-fluorophenyl)-2-(((3-methoxyphenyl)(methyl)amino)methyl)-6,7-dihydropyrazolo[1,5-a]pyrazin-4(5H)-one;

5-(4-fluorophenyl)-2-(((4-fluorophenyl)(methyl)amino)methyl)-6,7-dihydropyrazolo[1,5-a]pyrazin-4(5H)-one;

2-(((4-chlorophenyl)(methyl)amino)methyl)-5-(4-fluorophenyl)-6,7-dihydropyrazolo[1,5-a]pyrazin-4(5H)-one;

2-(((4-bromophenyl)(methyl)amino)methyl)-5-(4-fluorophenyl)-6,7-dihydropyrazolo[1,5-a]pyrazin-4(5H)-one;

5-(4-fluorophenyl)-2-(((4-methoxyphenyl)(methyl)amino)methyl)-6,7-dihydropyrazolo[1,5-a]pyrazin-4(5H)-one;

4-(((5-(4-fluorophenyl)-4-oxo-4,5,6,7-tetrahydropyrazolo[1,5-a]pyrazin-2-yl)methyl)(methyl)amino)benzonitrile;

2-(((3,5-difluorophenyl)(methyl)amino)methyl)-5-(4-fluorophenyl)-6,7-dihydropyrazolo[1,5-a]pyrazin-4(5H)-one;

5-(4-chlorophenyl)-2-(((4-methoxyphenyl)(methyl)amino)methyl)-6,7-dihydropyrazolo[1,5-a]pyrazin-4(5H)-one;

5-(3,4-difluorophenyl)-2-(((4-methoxyphenyl)(methyl)amino)methyl)-6,7-dihydropyrazolo[1,5-a]pyrazin-4(5H)-one;

5-(3-chlorophenyl)-2-(((4-methoxyphenyl)(methyl)amino)methyl)-6,7-dihydropyrazolo[1,5-a]pyrazin-4(5H)-one;

2-(((4-methoxyphenyl)(methyl)amino)methyl)-5-(p-tolyl)-6,7-dihydropyrazolo[1,5-a]pyrazin-4(5H)-one;

5-(2-chlorophenyl)-2-(((4-methoxyphenyl)(methyl)amino)methyl)-6,7-dihydropyrazolo[1,5-a]pyrazin-4(5H)-one;

5-(3-fluorophenyl)-2-(((4-methoxyphenyl)(methyl)amino)methyl)-6,7-dihydropyrazolo[1,5-a]pyrazin-4(5H)-one;

2-(((4-methoxyphenyl)(methyl)amino)methyl)-5-(2,4,6-trifluorophenyl)-6,7-dihydropyrazolo[1,5-a]pyrazin-4(5H)-one;

2-(((4-methoxyphenyl)(methyl)amino)methyl)-5-(m-tolyl)-6,7-dihydropyrazolo[1,5-a]pyrazin-4(5H)-one;

5-(3,5-difluorophenyl)-2-(((4-methoxyphenyl)(methyl)amino)methyl)-6,7-dihydropyrazolo[1,5-a]pyrazin-4(5H)-one;

5-(2-fluorophenyl)-2-(((4-methoxyphenyl)(methyl)amino)methyl)-6,7-dihydropyrazolo[1,5-a]pyrazin-4(5H)-one;

5-(2,5-difluorophenyl)-2-(((4-methoxyphenyl)(methyl)amino)methyl)-6,7-dihydropyrazolo[1,5-a]pyrazin-4(5H)-one;

5-(2,3-difluorophenyl)-2-(((4-methoxyphenyl)(methyl)amino)methyl)-6,7-dihydropyrazolo[1,5-a]pyrazin-4(5H)-one;

5-(2-fluoro-4-methylphenyl)-2-(((4-methoxyphenyl)(methyl)amino)methyl)-6,7-dihydropyrazolo[1,5-a]pyrazin-4(5H)-one;

5-(4-fluoro-2-methylphenyl)-2-(((4-methoxyphenyl)(methyl)amino)methyl)-6,7-dihydropyrazolo[1,5-a]pyrazin-4(5H)-one;

5-(2,6-difluorophenyl)-2-(((4-methoxyphenyl)(methyl)amino)methyl)-6,7-dihydropyrazolo[1,5-a]pyrazin-4(5H)-one;

2-(((4-methoxyphenyl)(methyl)amino)methyl)-5-(o-tolyl)-6,7-dihydropyrazolo[1,5-a]pyrazin-4(5H)-one;

2-(2-(((4-methoxyphenyl)(methyl)amino)methyl)-4-oxo-6,7-dihydropyrazolo[1,5-a]pyrazin-5(4H)-yl)benzonitrile;

5-(3-methoxyphenyl)-2-(((4-methoxyphenyl)(methyl)amino)methyl)-6,7-dihydropyrazolo[1,5-a]pyrazin-4(5H)-one;

5-(4-methoxyphenyl)-2-(((4-methoxyphenyl)(methyl)amino)methyl)-6,7-dihydropyrazolo[1,5-a]pyrazin-4(5H)-one;

2-(((4-methoxyphenyl)(methyl)amino)methyl)-5-(2-methylthiazol-4-yl)-6,7-dihydropyrazolo[1,5-a]pyrazin-4(5H)-one;

3-(2-(((4-methoxyphenyl)(methyl)amino)methyl)-4-oxo-6,7-dihydropyrazolo[1,5-a]pyrazin-5(4H)-yl)benzonitrile;

2-(((4-methoxyphenyl)(methyl)amino)methyl)-5-(pyridin-2-yl)-6,7-dihydropyrazolo[1,5-a]pyrazin-4(5H)-one;

4-(2-(((4-methoxyphenyl)(methyl)amino)methyl)-4-oxo-6,7-dihydropyrazolo[1,5-a]pyrazin-5(4H)-yl)benzonitrile;

5-(2-methoxyphenyl)-2-(((4-methoxyphenyl)(methyl)amino)methyl)-6,7-dihydropyrazolo[1,5-a]pyrazin-4(5H)-one;

5-(4-(methoxymethyl)phenyl)-2-(((4-methoxyphenyl)(methyl)amino)methyl)-6,7-dihydropyrazolo[1,5-a]pyrazin-4(5H)-one;
2-(((4-methoxyphenyl)(methyl)amino)methyl)-5-(pyridin-3-yl)-6,7-dihydropyrazolo[1,5-a]pyrazin-4(5H)-one;
5-(5-fluoropyridin-2-yl)-2-(((4-methoxyphenyl)(methyl)amino)methyl)-6,7-dihydropyrazolo[1,5-a]pyrazin-4(5H)-one;
5-(4-(difluoromethoxy)phenyl)-2-(((4-methoxyphenyl)(methyl)amino)methyl)-6,7-dihydropyrazolo[1,5-a]pyrazin-4(5H)-one;
5-(5-chloropyridin-2-yl)-2-(((4-methoxyphenyl)(methyl)amino)methyl)-6,7-dihydropyrazolo[1,5-a]pyrazin-4(5H)-one;
5-(3,4-difluorophenyl)-2-((ethyl(4-methoxyphenyl)amino)methyl)-6,7-dihydropyrazolo[1,5-a]pyrazin-4(5H)-one;
5-(3,4-difluorophenyl)-2-(((4-methoxyphenyl)(propyl)amino)methyl)-6,7-dihydropyrazolo[1,5-a]pyrazin-4(5H)-one;
5-(4-chloro-2-fluorophenyl)-2-(((4-methoxyphenyl)(methyl)amino)methyl)-6,7-dihydropyrazolo[1,5-a]pyrazin-4(5H)-one;
5-(2-chloro-3-fluorophenyl)-2-(((4-methoxyphenyl)(methyl)amino)methyl)-6,7-dihydropyrazolo[1,5-a]pyrazin-4(5H)-one;
5-(5-chloro-2-fluorophenyl)-2-(((4-methoxyphenyl)(methyl)amino)methyl)-6,7-dihydropyrazolo[1,5-a]pyrazin-4(5H)-one;
5-(4-chloro-2,6-difluorophenyl)-2-(((4-methoxyphenyl)(methyl)amino)methyl)-6,7-dihydropyrazolo[1,5-a]pyrazin-4(5H)-one;
5-(2-chloro-5-fluorophenyl)-2-(((4-methoxyphenyl)(methyl)amino)methyl)-6,7-dihydropyrazolo[1,5-a]pyrazin-4(5H)-one;
5-(2-chloro-4-fluorophenyl)-2-(((4-methoxyphenyl)(methyl)amino)methyl)-6,7-dihydropyrazolo[1,5-a]pyrazin-4(5H)-one;
5-(3-chloro-5-fluorophenyl)-2-(((4-methoxyphenyl)(methyl)amino)methyl)-6,7-dihydropyrazolo[1,5-a]pyrazin-4(5H)-one;
5-(3-fluoro-5-methoxyphenyl)-2-(((4-methoxyphenyl)(methyl)amino)methyl)-6,7-dihydropyrazolo[1,5-a]pyrazin-4(5H)-one;
5-(3-chloro-4-fluorophenyl)-2-(((4-methoxyphenyl)(methyl)amino)methyl)-6,7-dihydropyrazolo[1,5-a]pyrazin-4(5H)-one;
5-(3-chloro-5-methoxyphenyl)-2-(((4-methoxyphenyl)(methyl)amino)methyl)-6,7-dihydropyrazolo[1,5-a]pyrazin-4(5H)-one;
5-(3-chloro-2-fluorophenyl)-2-(((4-methoxyphenyl)(methyl)amino)methyl)-6,7-dihydropyrazolo[1,5-a]pyrazin-4(5H)-one; and
5-(4-chloro-3-fluorophenyl)-2-(((4-methoxyphenyl)(methyl)amino)methyl)-6,7-dihydropyrazolo[1,5-a]pyrazin-4(5H)-one.

11. The compound of claim 1, or a pharmaceutically acceptable salt thereof, selected from the group consisting of:
(R)-5-(4-fluorophenyl)-7-methyl-2-((phenylamino)methyl)-6,7-dihydropyrazolo[1,5-a]pyrazin-4(5H)-one;
(R)-5-(4-fluorophenyl)-2-(((2-fluorophenyl)amino)methyl)-7-methyl-6,7-dihydropyrazolo[1,5-a]pyrazin-4(5H)-one;
(R)-5-(4-fluorophenyl)-7-methyl-2-((o-tolylamino)methyl)-6,7-dihydropyrazolo[1,5-a]pyrazin-4(5H)-one;
(R)-5-(4-fluorophenyl)-2-(((3-fluorophenyl)amino)methyl)-7-methyl-6,7-dihydropyrazolo[1,5-a]pyrazin-4(5H)-one;
(R)-2-(((3-chlorophenyl)amino)methyl)-5-(4-fluorophenyl)-7-methyl-6,7-dihydropyrazolo[1,5-a]pyrazin-4(5H)-one;
(R)-5-(4-fluorophenyl)-7-methyl-2-((m-tolylamino)methyl)-6,7-dihydropyrazolo[1,5-a]pyrazin-4(5H)-one;
(R)-5-(4-fluorophenyl)-2-(((3-methoxyphenyl)amino)methyl)-7-methyl-6,7-dihydropyrazolo[1,5-a]pyrazin-4(5H)-one;
(R)-2-(((3-(difluoromethoxy)phenyl)amino)methyl)-5-(4-fluorophenyl)-7-methyl-6,7-dihydropyrazolo[1,5-a]pyrazin-4(5H)-one;
(R)-5-(4-fluorophenyl)-2-(((4-fluorophenyl)amino)methyl)-7-methyl-6,7-dihydropyrazolo[1,5-a]pyrazin-4(5H)-one;
(R)-5-(4-fluorophenyl)-7-methyl-2-((p-tolylamino)methyl)-6,7-dihydropyrazolo[1,5-a]pyrazin-4(5H)-one;
(R)-2-(((4-chlorophenyl)amino)methyl)-5-(4-fluorophenyl)-7-methyl-6,7-dihydropyrazolo[1,5-a]pyrazin-4(5H)-one;
(R)-5-(4-fluorophenyl)-2-(((4-methoxyphenyl)amino)methyl)-7-methyl-6,7-dihydropyrazolo[1,5-a]pyrazin-4(5H)-one;
(R)-2-(((4-(difluoromethoxy)phenyl)amino)methyl)-5-(4-fluorophenyl)-7-methyl-6,7-dihydropyrazolo[1,5-a]pyrazin-4(5H)-one;
(R)-2-(4-(((5-(4-fluorophenyl)-7-methyl-4-oxo-4,5,6,7-tetrahydropyrazolo[1,5-a]pyrazin-2-yl)methyl)amino)phenyl)acetonitrile;
(R)-2-(((2,3-difluorophenyl)amino)methyl)-5-(4-fluorophenyl)-7-methyl-6,7-dihydropyrazolo[1,5-a]pyrazin-4(5H)-one;
(R)-2-(((2,5-difluorophenyl)amino)methyl)-5-(4-fluorophenyl)-7-methyl-6,7-dihydropyrazolo[1,5-a]pyrazin-4(5H)-one;
(R)-2-(((2,6-difluorophenyl)amino)methyl)-5-(4-fluorophenyl)-7-methyl-6,7-dihydropyrazolo[1,5-a]pyrazin-4(5H)-one;
(R)-2-(((2,4-difluorophenyl)amino)methyl)-5-(4-fluorophenyl)-7-methyl-6,7-dihydropyrazolo[1,5-a]pyrazin-4(5H)-one;
(R)-2-(((3,4-difluorophenyl)amino)methyl)-5-(4-fluorophenyl)-7-methyl-6,7-dihydropyrazolo[1,5-a]pyrazin-4(5H)-one; and
(R)-5-(4-fluorophenyl)-7-methyl-2-(((2,4,6-trifluorophenyl)amino)methyl)-6,7-dihydropyrazolo[1,5-a]pyrazin-4(5H)-one.

12. The compound of claim 1, or a pharmaceutically acceptable salt thereof, selected from the group consisting of:
5-(4-fluorophenyl)-2-((phenylamino)methyl)-6,7-dihydropyrazolo[1,5-a]pyrazin-4(5H)-one;
5-(4-fluorophenyl)-2-(((2-fluorophenyl)amino)methyl)-6,7-dihydropyrazolo[1,5-a]pyrazin-4(5H)-one;
5-(4-fluorophenyl)-2-((o-tolylamino)methyl)-6,7-dihydropyrazolo[1,5-a]pyrazin-4(5H)-one;
2-(((2-chlorophenyl)amino)methyl)-5-(4-fluorophenyl)-6,7-dihydropyrazolo[1,5-a]pyrazin-4(5H)-one;

5-(4-fluorophenyl)-2-(((2-methoxyphenyl)amino)
methyl)-6,7-dihydropyrazolo[1,5-a]pyrazin-4(5H)-
one;
5-(4-fluorophenyl)-2-(((2-fluorophenyl)amino)methyl)-
6,7-dihydropyrazolo[1,5-a]pyrazin-4(5H)-one;
5-(4-fluorophenyl)-2-((m-tolylamino)methyl)-6,7-dihy-
dropyrazolo[1,5-a]pyrazin-4(5H)-one;
2-(((3-chlorophenyl)amino)methyl)-5-(4-fluorophenyl)-
6,7-dihydropyrazolo[1,5-a]pyrazin-4(5H)-one;
5-(4-fluorophenyl)-2-(((3-methoxyphenyl)amino)
methyl)-6,7-dihydropyrazolo[1,5-a]pyrazin-4(5H)-
one;
3-(((5-(4-fluorophenyl)-4-oxo-4,5,6,7-tetrahydropyra-
zolo[1,5-a]pyrazin-2-yl)methyl)amino)benzonitrile;
2-(((3-(difluoromethoxy)phenyl)amino)methyl)-5-(4-
fluorophenyl)-6,7-dihydropyrazolo[1,5-a]pyrazin-4
(5H)-one;
5-(4-fluorophenyl)-2-(((4-fluorophenyl)amino)methyl)-
6,7-dihydropyrazolo[1,5-a]pyrazin-4(5H)-one;
5-(4-fluorophenyl)-2-((p-tolylamino)methyl)-6,7-dihy-
dropyrazolo[1,5-a]pyrazin-4(5H)-one;
2-(((4-chlorophenyl)amino)methyl)-5-(4-fluorophenyl)-
6,7-dihydropyrazolo[1,5-a]pyrazin-4(5H)-one;
2-(((4-bromophenyl)amino)methyl)-5-(4-fluorophenyl)-
6,7-dihydropyrazolo[1,5-a]pyrazin-4(5H)-one;
5-(4-fluorophenyl)-2-(((4-methoxyphenyl)amino)
methyl)-6,7-dihydropyrazolo[1,5-a]pyrazin-4(5H)-
one;
4-(((5-(4-fluorophenyl)-4-oxo-4,5,6,7-tetrahydropyra-
zolo[1,5-a]pyrazin-2-yl)methyl)amino)benzonitrile;
5-(4-fluorophenyl)-2-(((4-(trifluoromethyl)phenyl)
amino)methyl)-6,7-dihydropyrazolo[1,5-a]pyrazin-4
(5H)-one;
2-(((4-(difluoromethoxy)phenyl)amino)methyl)-5-(4-
fluorophenyl)-6,7-dihydropyrazolo[1,5-a]pyrazin-4
(5H)-one;
5-(4-fluorophenyl)-2-(((4-(trifluoromethoxy)phenyl)
amino)methyl)-6,7-dihydropyrazolo[1,5-a]pyrazin-4
(5H)-one;
2-(((4-ethylphenyl)amino)methyl)-5-(4-fluorophenyl)-6,
7-dihydropyrazolo[1,5-a]pyrazin-4(5H)-one;
5-(4-fluorophenyl)-2-(((4-isopropylphenyl)amino)
methyl)-6,7-dihydropyrazolo[1,5-a]pyrazin-4(5H)-
one;
2-(((4-(tert-butyl)phenyl)amino)methyl)-5-(4-fluorophe-
nyl)-6,7-dihydropyrazolo[1,5-a]pyrazin-4(5H)-one;
5-(4-fluorophenyl)-2-(((4-(methylsulfonyl)phenyl)
amino)methyl)-6,7-dihydropyrazolo[1,5-a]pyrazin-4
(5H)-one;
2-(4-(((5-(4-fluorophenyl)-4-oxo-4,5,6,7-tetrahydropyra-
zolo[1,5-a]pyrazin-2-yl)methyl)amino)phenyl)acetoni-
trile;
2-(((2,3-difluorophenyl)amino)methyl)-5-(4-fluorophe-
nyl)-6,7-dihydropyrazolo[1,5-a]pyrazin-4(5H)-one;
2-(((2,4-difluorophenyl)amino)methyl)-5-(4-fluorophe-
nyl)-6,7-dihydropyrazolo[1,5-a]pyrazin-4(5H)-one;
2-(((2,5-difluorophenyl)amino)methyl)-5-(4-fluorophe-
nyl)-6,7-dihydropyrazolo[1,5-a]pyrazin-4(5H)-one;
2-(((3,5-difluorophenyl)amino)methyl)-5-(4-fluorophe-
nyl)-6,7-dihydropyrazolo[1,5-a]pyrazin-4(5H)-one;
2-(((3,4-difluorophenyl)amino)methyl)-5-(4-fluorophe-
nyl)-6,7-dihydropyrazolo[1,5-a]pyrazin-4(5H)-one;
2-(((2,6-difluorophenyl)amino)methyl)-5-(4-fluorophe-
nyl)-6,7-dihydropyrazolo[1,5-a]pyrazin-4(5H)-one;
5-(4-fluorophenyl)-2-(((2,4,6-trifluorophenyl)amino)
methyl)-6,7-dihydropyrazolo[1,5-a]pyrazin-4(5H)-
one;
2-(((4-chloro-2-fluorophenyl)amino)methyl)-5-(4-fluoro-
phenyl)-6,7-dihydropyrazolo[1,5-a]pyrazin-4(5H)-
one;
2-(((2-fluoro-4-methylphenyl)amino)methyl)-5-(4-fluo-
rophenyl)-6,7-dihydropyrazolo[1,5-a]pyrazin-4(5H)-
one;
2-(((4-fluoro-3-methylphenyl)amino)methyl)-5-(4-fluo-
rophenyl)-6,7-dihydropyrazolo[1,5-a]pyrazin-4(5H)-
one;
2-(((4-(difluoromethoxy)-2-fluorophenyl)amino)methyl)-
5-(4-fluorophenyl)-6,7-dihydropyrazolo[1,5-a]
pyrazin-4(5H)-one;
2-(((4-(difluoromethoxy)-3-fluorophenyl)amino)methyl)-
5-(4-fluorophenyl)-6,7-dihydropyrazolo[1,5-a]
pyrazin-4(5H)-one;
2-(((2,2-difluorobenzo[d][1,3]dioxol-5-yl)amino)
methyl)-5-(4-fluorophenyl)-6,7-dihydropyrazolo[1,5-
a]pyrazin-4(5H)-one;
5-(4-fluorophenyl)-2-(((5-fluoropyridin-2-yl)amino)
methyl)-6,7-dihydropyrazolo[1,5-a]pyrazin-4(5H)-
one;
5-(4-fluorophenyl)-2-((pyridin-2-ylamino)methyl)-6,7-
dihydropyrazolo[1,5-a]pyrazin-4(5H)-one;
5-(4-fluorophenyl)-2-(((6-methylpyridin-2-yl)amino)
methyl)-6,7-dihydropyrazolo[1,5-a]pyrazin-4(5H)-
one;
2-(((5-chloropyridin-2-yl)amino)methyl)-5-(4-fluorophe-
nyl)-6,7-dihydropyrazolo[1,5-a]pyrazin-4(5H)-one;
5-(4-fluorophenyl)-2-(((5-methylpyridin-2-yl)amino)
methyl)-6,7-dihydropyrazolo[1,5-a]pyrazin-4(5H)-
one;
5-(4-fluorophenyl)-2-(((3-methylpyridin-2-yl)amino)
methyl)-6,7-dihydropyrazolo[1,5-a]pyrazin-4(5H)-
one;
5-(4-fluorophenyl)-2-(((4-methylpyridin-2-yl)amino)
methyl)-6,7-dihydropyrazolo[1,5-a]pyrazin-4(5H)-
one;
5-(4-fluorophenyl)-2-(((3-(trifluoromethyl)pyridin-2-yl)
amino)methyl)-6,7-dihydropyrazolo[1,5-a]pyrazin-4
(5H)-one;
2-(((6-chloropyridin-2-yl)amino)methyl)-5-(4-fluorophe-
nyl)-6,7-dihydropyrazolo[1,5-a]pyrazin-4(5H)-one;
2-(((4-chloropyridin-2-yl)amino)methyl)-5-(4-fluorophe-
nyl)-6,7-dihydropyrazolo[1,5-a]pyrazin-4(5H)-one;
2-(((3-chloropyridin-2-yl)amino)methyl)-5-(4-fluorophe-
nyl)-6,7-dihydropyrazolo[1,5-a]pyrazin-4(5H)-one;
5-(4-fluorophenyl)-2-(((3-fluoropyridin-2-yl)amino)
methyl)-6,7-dihydropyrazolo[1,5-a]pyrazin-4(5H)-
one;
5-(4-fluorophenyl)-2-(((6-(trifluoromethyl)pyridin-2-yl)
amino)methyl)-6,7-dihydropyrazolo[1,5-a]pyrazin-4
(5H)-one;
5-(3,4-difluorophenyl)-2-(((4-methoxyphenyl)amino)
methyl)-6,7-dihydropyrazolo[1,5-a]pyrazin-4(5H)-
one;
5-(4-chlorophenyl)-2-(((4-methoxyphenyl)amino)
methyl)-6,7-dihydropyrazolo[1,5-a]pyrazin-4(5H)-
one;
2-(((4-(difluoromethoxy)-2-fluorophenyl)amino)methyl)-
5-(5-methylthiazol-2-yl)-6,7-dihydropyrazolo[1,5-a]
pyrazin-4(5H)-one;
2-(((4-(difluoromethoxy)-2-fluorophenyl)amino)methyl)-
5-(6-fluoropyridin-2-yl)-6,7-dihydropyrazolo[1,5-a]
pyrazin-4(5H)-one;
5-(4-chloropyridin-2-yl)-2-(((4-(difluoromethoxy)-2-
fluorophenyl)amino)methyl)-6,7-dihydropyrazolo[1,5-
a]pyrazin-4(5H)-one;

2-(((4-(difluoromethoxy)-2-fluorophenyl)amino)methyl)-5-(2-methylthiazol-4-yl)-6,7-dihydropyrazolo[1,5-a]pyrazin-4(5H)-one;

2-(((4-(difluoromethoxy)-2-fluorophenyl)amino)methyl)-5-(2,4-difluorophenyl)-6,7-dihydropyrazolo[1,5-a]pyrazin-4(5H)-one;

2-(((4-(difluoromethoxy)-2-fluorophenyl)amino)methyl)-5-(3-methoxyphenyl)-6,7-dihydropyrazolo[1,5-a]pyrazin-4(5H)-one;

2-(((4-(difluoromethoxy)-2-fluorophenyl)amino)methyl)-5-(3-fluoropyridin-2-yl)-6,7-dihydropyrazolo[1,5-a]pyrazin-4(5H)-one;

2-(((4-(difluoromethoxy)-2-fluorophenyl)amino)methyl)-5-(5-methylpyridin-2-yl)-6,7-dihydropyrazolo[1,5-a]pyrazin-4(5H)-one;

2-(((4-(difluoromethoxy)-2-fluorophenyl)amino)methyl)-5-(3-fluorophenyl)-6,7-dihydropyrazolo[1,5-a]pyrazin-4(5H)-one;

2-(((4-(difluoromethoxy)-2-fluorophenyl)amino)methyl)-5-(3,4-difluorophenyl)-6,7-dihydropyrazolo[1,5-a]pyrazin-4(5H)-one;

2-(((4-(difluoromethoxy)-2-fluorophenyl)amino)methyl)-5-(5-fluoropyridin-2-yl)-6,7-dihydropyrazolo[1,5-a]pyrazin-4(5H)-one;

2-(((4-(difluoromethoxy)-2-fluorophenyl)amino)methyl)-5-(3-fluoro-5-methoxyphenyl)-6,7-dihydropyrazolo[1,5-a]pyrazin-4(5H)-one;

5-(5-chloropyridin-2-yl)-2-(((4-(difluoromethoxy)-2-fluorophenyl)amino)methyl)-6,7-dihydropyrazolo[1,5-a]pyrazin-4(5H)-one;

5-(4-chloro-2-fluorophenyl)-2-(((4-(difluoromethoxy)-2-fluorophenyl)amino)methyl)-6,7-dihydropyrazolo[1,5-a]pyrazin-4(5H)-one;

5-(3-chlorophenyl)-2-(((4-(difluoromethoxy)-2-fluorophenyl)amino)methyl)-6,7-dihydropyrazolo[1,5-a]pyrazin-4(5H)-one;

2-(((4-(difluoromethoxy)-2-fluorophenyl)amino)methyl)-5-(pyridin-2-yl)-6,7-dihydropyrazolo[1,5-a]pyrazin-4(5H)-one;

2-(((4-(difluoromethoxy)-2-fluorophenyl)amino)methyl)-5-(3,5-difluorophenyl)-6,7-dihydropyrazolo[1,5-a]pyrazin-4(5H)-one; and 2-(((4-(difluoromethoxy)-2-fluorophenyl)amino)methyl)-5-(2-fluorophenyl)-6,7-dihydropyrazolo[1,5-a]pyrazin-4(5H)-one.

13. The compound of claim 1, or a pharmaceutically acceptable salt thereof, selected from the group consisting of:

5-(4-fluorophenyl)-2-(1-(phenylamino)ethyl)-6,7-dihydropyrazolo[1,5-a]pyrazin-4(5H)-one;

5-(4-fluorophenyl)-2-(1-((4-fluorophenyl)amino)ethyl)-6,7-dihydropyrazolo[1,5-a]pyrazin-4(5H)-one;

2-(1-((4-chlorophenyl)amino)ethyl)-5-(4-fluorophenyl)-6,7-dihydropyrazolo[1,5-a]pyrazin-4(5H)-one; and 5-(4-fluorophenyl)-2-(1-((4-methoxyphenyl)amino)ethyl)-6,7-dihydropyrazolo[1,5-a]pyrazin-4(5H)-one.

14. A pharmaceutical composition comprising a therapeutically effective amount of a compound of claim 1, or a pharmaceutically acceptable salt thereof, in combination with one or more pharmaceutically acceptable carriers.

15. A method for modulating metabotropic glutamate receptor 3 activity in a subject, the method comprising administering a therapeutically effective amount of a compound of claim 1, or a pharmaceutically acceptable salt thereof, to a subject in need thereof.

16. The method of claim 15, wherein administering the compound of claim 1 to the subject results in inhibition of at least one process governed by the metabotropic glutamate receptor 3 in the subject.

17. The method of claim 15, wherein the subject suffers from at least one disease or disorder selected from depression, Alzheimer's disease, dementia, delirium, amnestic disorders, age-related cognitive decline, schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder.

18. The method of claim 15, wherein the subject suffers from at least one disease or disorder selected from schizophrenia, Alzheimer's disease, and depression.

19. The method of claim 15, wherein the subject suffers from at least one proliferative disease or disorder selected from cancer and glioma.

20. A compound, or a pharmaceutically acceptable salt thereof, selected from the group consisting of:

5-(4-fluorophenyl)-2-((phenylamino)methyl)-6,7-dihydropyrazolo[1,5-a]pyrazin-4(5H)-one;

5-(4-fluorophenyl)-2-(((2-fluorophenyl)amino)methyl)-6,7-dihydropyrazolo[1,5-a]pyrazin-4(5H)-one;

5-(4-fluorophenyl)-2-((o-tolylamino)methyl)-6,7-dihydropyrazolo[1,5-a]pyrazin-4(5H)-one;

2-(((2-chlorophenyl)amino)methyl)-5-(4-fluorophenyl)-6,7-dihydropyrazolo[1,5-a]pyrazin-4(5H)-one;

5-(4-fluorophenyl)-2-(((2-methoxyphenyl)amino)methyl)-6,7-dihydropyrazolo[1,5-a]pyrazin-4(5H)-one;

5-(4-fluorophenyl)-2-(((3-fluorophenyl)amino)methyl)-6,7-dihydropyrazolo[1,5-a]pyrazin-4(5H)-one;

5-(4-fluorophenyl)-2-((m-tolylamino)methyl)-6,7-dihydropyrazolo[1,5-a]pyrazin-4(5H)-one;

2-(((3-chlorophenyl)amino)methyl)-5-(4-fluorophenyl)-6,7-dihydropyrazolo[1,5-a]pyrazin-4(5H)-one;

5-(4-fluorophenyl)-2-(((3-methoxyphenyl)amino)methyl)-6,7-dihydropyrazolo[1,5-a]pyrazin-4(5H)-one;

3-(((5-(4-fluorophenyl)-4-oxo-4,5,6,7-tetrahydropyrazolo[1,5-a]pyrazin-2-yl)methyl)amino)benzonitrile;

2-(((3-(difluoromethoxy)phenyl)amino)methyl)-5-(4-fluorophenyl)-6,7-dihydropyrazolo[1,5-a]pyrazin-4(5H)-one;

5-(4-fluorophenyl)-2-(((4-fluorophenyl)amino)methyl)-6,7-dihydropyrazolo[1,5-a]pyrazin-4(5H)-one;

5-(4-fluorophenyl)-2-((p-tolylamino)methyl)-6,7-dihydropyrazolo[1,5-a]pyrazin-4(5H)-one;

2-(((4-chlorophenyl)amino)methyl)-5-(4-fluorophenyl)-6,7-dihydropyrazolo[1,5-a]pyrazin-4(5H)-one;

2-(((4-bromophenyl)amino)methyl)-5-(4-fluorophenyl)-6,7-dihydropyrazolo[1,5-a]pyrazin-4(5H)-one;

5-(4-fluorophenyl)-2-(((4-methoxyphenyl)amino)methyl)-6,7-dihydropyrazolo[1,5-a]pyrazin-4(5H)-one;

4-(((5-(4-fluorophenyl)-4-oxo-4,5,6,7-tetrahydropyrazolo[1,5-a]pyrazin-2-yl)methyl)amino)benzonitrile;

5-(4-fluorophenyl)-2-(((4-(trifluoromethyl)phenyl)
amino)methyl)-6,7-dihydropyrazolo[1,5-a]pyrazin-4
(5H)-one;
2-(((4-(difluoromethoxy)phenyl)amino)methyl)-5-(4-
fluorophenyl)-6,7-dihydropyrazolo[1,5-a]pyrazin-4
(5H)-one;
5-(4-fluorophenyl)-2-(((4-(trifluoromethoxy)phenyl)
amino)methyl)-6,7-dihydropyrazolo[1,5-a]pyrazin-4
(5H)-one;
2-(((4-ethylphenyl)amino)methyl)-5-(4-fluorophenyl)-6,
7-dihydropyrazolo[1,5-a]pyrazin-4(5H)-one;
5-(4-fluorophenyl)-2-(((4-isopropylphenyl)amino)
methyl)-6,7-dihydropyrazolo[1,5-a]pyrazin-4(5H)-
one;
2-(((4-(tert-butyl)phenyl)amino)methyl)-5-(4-fluorophe-
nyl)-6,7-dihydropyrazolo[1,5-a]pyrazin-4(5H)-one;
5-(4-fluorophenyl)-2-(((4-(methylsulfonyl)phenyl)
amino)methyl)-6,7-dihydropyrazolo[1,5-a]pyrazin-4
(5H)-one;
2-(4-(((5-(4-fluorophenyl)-4-oxo-4,5,6,7-tetrahydropyra-
zolo[1,5-a]pyrazin-2-yl)methyl)amino)phenyl)acetoni-
trile;
2-(((2,3-difluorophenyl)amino)methyl)-5-(4-fluorophe-
nyl)-6,7-dihydropyrazolo[1,5-a]pyrazin-4(5H)-one;
2-(((2,4-difluorophenyl)amino)methyl)-5-(4-fluorophe-
nyl)-6,7-dihydropyrazolo[1,5-a]pyrazin-4(5H)-one;
2-(((2,5-difluorophenyl)amino)methyl)-5-(4-fluorophe-
nyl)-6,7-dihydropyrazolo[1,5-a]pyrazin-4(5H)-one;
2-(((3,5-difluorophenyl)amino)methyl)-5-(4-fluorophe-
nyl)-6,7-dihydropyrazolo[1,5-a]pyrazin-4(5H)-one;
2-(((3,4-difluorophenyl)amino)methyl)-5-(4-fluorophe-
nyl)-6,7-dihydropyrazolo[1,5-a]pyrazin-4(5H)-one;
2-(((2,6-difluorophenyl)amino)methyl)-5-(4-fluorophe-
nyl)-6,7-dihydropyrazolo[1,5-a]pyrazin-4(5H)-one;
5-(4-fluorophenyl)-2-(((2,4,6-trifluorophenyl)amino)
methyl)-6,7-dihydropyrazolo[1,5-a]pyrazin-4(5H)-
one;
2-(((4-chloro-2-fluorophenyl)amino)methyl)-5-(4-fluoro-
phenyl)-6,7-dihydropyrazolo[1,5-a]pyrazin-4(5H)-
one;
2-(((2-fluoro-4-methylphenyl)amino)methyl)-5-(4-fluo-
rophenyl)-6,7-dihydropyrazolo[1,5-a]pyrazin-4(5H)-
one;
2-(((4-fluoro-3-methylphenyl)amino)methyl)-5-(4-fluo-
rophenyl)-6,7-dihydropyrazolo[1,5-a]pyrazin-4(5H)-
one;
2-(((4-(difluoromethoxy)-2-fluorophenyl)amino)methyl)-
5-(4-fluorophenyl)-6,7-dihydropyrazolo[1,5-a]
pyrazin-4(5H)-one;
2-(((4-(difluoromethoxy)-3-fluorophenyl)amino)methyl)-
5-(4-fluorophenyl)-6,7-dihydropyrazolo[1,5-a]
pyrazin-4(5H)-one;
2-(((2,2-difluorobenzo[d][1,3]dioxol-5-yl)amino)
methyl)-5-(4-fluorophenyl)-6,7-dihydropyrazolo[1,5-
a]pyrazin-4(5H)-one;
5-(4-fluorophenyl)-2-((methyl(phenyl)amino)methyl)-6,
7-dihydropyrazolo[1,5-a]pyrazin-4(5H)-one;
5-(4-fluorophenyl)-2-(((2-fluorophenyl)(methyl)amino)
methyl)-6,7-dihydropyrazolo[1,5-a]pyrazin-4(5H)-one;
2-(((2-chlorophenyl)(methyl)amino)methyl)-5-(4-fluoro-
phenyl)-6,7-dihydropyrazolo[1,5-a]pyrazin-4(5H)-
one;
5-(4-fluorophenyl)-2-(((2-methoxyphenyl)(methyl)
amino)methyl)-6,7-dihydropyrazolo[1,5-a]pyrazin-4
(5H)-one;
5-(4-fluorophenyl)-2-(((3-fluorophenyl)(methyl)amino)
methyl)-6,7-dihydropyrazolo[1,5-a]pyrazin-4(5H)-
one;
2-(((3-chlorophenyl)(methyl)amino)methyl)-5-(4-fluoro-
phenyl)-6,7-dihydropyrazolo[1,5-a]pyrazin-4(5H)-
one;
5-(4-fluorophenyl)-2-(((3-methoxyphenyl)(methyl)
amino)methyl)-6,7-dihydropyrazolo[1,5-a]pyrazin-4
(5H)-one;
5-(4-fluorophenyl)-2-(((4-fluorophenyl)(methyl)amino)
methyl)-6,7-dihydropyrazolo[1,5-a]pyrazin-4(5H)-
one;
2-(((4-chlorophenyl)(methyl)amino)methyl)-5-(4-fluoro-
phenyl)-6,7-dihydropyrazolo[1,5-a]pyrazin-4(5H)-
one;
2-(((4-bromophenyl)(methyl)amino)methyl)-5-(4-fluoro-
phenyl)-6,7-dihydropyrazolo[1,5-a]pyrazin-4(5H)-
one;
5-(4-fluorophenyl)-2-(((4-methoxyphenyl)(methyl)
amino)methyl)-6,7-dihydropyrazolo[1,5-a]pyrazin-4
(5H)-one;
4-(((5-(4-fluorophenyl)-4-oxo-4,5,6,7-tetrahydropyra-
zolo[1,5-a]pyrazin-2-yl)methyl)(methyl)amino)benzo-
nitrile;
(R)-5-(4-fluorophenyl)-7-methyl-2-((phenylamino)
methyl)-6,7-dihydropyrazolo[1,5-a]pyrazin-4(5H)-
one;
(S)-5-(4-fluorophenyl)-7-methyl-2-((phenylamino)
methyl)-6,7-dihydropyrazolo[1,5-a]pyrazin-4(5H)-
one;
(R)-5-(4-fluorophenyl)-2-(((2-fluorophenyl)amino)
methyl)-7-methyl-6,7-dihydropyrazolo[1,5-a]pyrazin-
4(5H)-one;
(S)-5-(4-fluorophenyl)-2-(((2-fluorophenyl)amino)
methyl)-7-methyl-6,7-dihydropyrazolo[1,5-a]pyrazin-
4(5H)-one;
(R)-5-(4-fluorophenyl)-7-methyl-2-((o-tolylamino)
methyl)-6,7-dihydropyrazolo[1,5-a]pyrazin-4(5H)-
one;
(S)-5-(4-fluorophenyl)-7-methyl-2-((o-tolylamino)
methyl)-6,7-dihydropyrazolo[1,5-a]pyrazin-4(5H)-
one;
(R)-5-(4-fluorophenyl)-2-(((3-fluorophenyl)amino)
methyl)-7-methyl-6,7-dihydropyrazolo[1,5-a]pyrazin-
4(5H)-one;
(S)-5-(4-fluorophenyl)-2-(((3-fluorophenyl)amino)
methyl)-7-methyl-6,7-dihydropyrazolo[1,5-a]pyrazin-
4(5H)-one;
(R)-2-(((3-chlorophenyl)amino)methyl)-5-(4-fluorophe-
nyl)-7-methyl-6,7-dihydropyrazolo[1,5-a]pyrazin-4
(5H)-one;
(S)-2-(((3-chlorophenyl)amino)methyl)-5-(4-fluorophe-
nyl)-7-methyl-6,7-dihydropyrazolo[1,5-a]pyrazin-4
(5H)-one;
(R)-5-(4-fluorophenyl)-7-methyl-2-((m-tolylamino)
methyl)-6,7-dihydropyrazolo[1,5-a]pyrazin-4(5H)-
one;
(S)-5-(4-fluorophenyl)-7-methyl-2-((m-tolylamino)
methyl)-6,7-dihydropyrazolo[1,5-a]pyrazin-4(5H)-
one;
(R)-5-(4-fluorophenyl)-2-(((3-methoxyphenyl)amino)
methyl)-7-methyl-6,7-dihydropyrazolo[1,5-a]pyrazin-
4(5H)-one;
(S)-5-(4-fluorophenyl)-2-(((3-methoxyphenyl)amino)
methyl)-7-methyl-6,7-dihydropyrazolo[1,5-a]pyrazin-
4(5H)-one;

(R)-2-(((3-(difluoromethoxy)phenyl)amino)methyl)-5-(4-fluorophenyl)-7-methyl-6,7-dihydropyrazolo[1,5-a]pyrazin-4(5H)-one;

(S)-2-(((3-(difluoromethoxy)phenyl)amino)methyl)-5-(4-fluorophenyl)-7-methyl-6,7-dihydropyrazolo[1,5-a]pyrazin-4(5H)-one;

(R)-5-(4-fluorophenyl)-2-(((4-fluorophenyl)amino)methyl)-7-methyl-6,7-dihydropyrazolo[1,5-a]pyrazin-4(5H)-one;

(S)-5-(4-fluorophenyl)-2-(((4-fluorophenyl)amino)methyl)-7-methyl-6,7-dihydropyrazolo[1,5-a]pyrazin-4(5H)-one;

(R)-5-(4-fluorophenyl)-7-methyl-2-((p-tolylamino)methyl)-6,7-dihydropyrazolo[1,5-a]pyrazin-4(5H)-one;

(S)-5-(4-fluorophenyl)-7-methyl-2-((p-tolylamino)methyl)-6,7-dihydropyrazolo[1,5-a]pyrazin-4(5H)-one;

(R)-2-(((4-chlorophenyl)amino)methyl)-5-(4-fluorophenyl)-7-methyl-6,7-dihydropyrazolo[1,5-a]pyrazin-4(5H)-one;

(S)-2-(((4-chlorophenyl)amino)methyl)-5-(4-fluorophenyl)-7-methyl-6,7-dihydropyrazolo[1,5-a]pyrazin-4(5H)-one;

(R)-5-(4-fluorophenyl)-2-(((4-methoxyphenyl)amino)methyl)-7-methyl-6,7-dihydropyrazolo[1,5-a]pyrazin-4(5H)-one;

(S)-5-(4-fluorophenyl)-2-(((4-methoxyphenyl)amino)methyl)-7-methyl-6,7-dihydropyrazolo[1,5-a]pyrazin-4(5H)-one;

(R)-2-(((4-(difluoromethoxy)phenyl)amino)methyl)-5-(4-fluorophenyl)-7-methyl-6,7-dihydropyrazolo[1,5-a]pyrazin-4(5H)-one;

(S)-2-(((4-(difluoromethoxy)phenyl)amino)methyl)-5-(4-fluorophenyl)-7-methyl-6,7-dihydropyrazolo[1,5-a]pyrazin-4(5H)-one;

(R)-2-(4-(((5-(4-fluorophenyl)-7-methyl-4-oxo-4,5,6,7-tetrahydropyrazolo[1,5-a]pyrazin-2-yl)methyl)amino)phenyl)acetonitrile;

(S)-2-(4-(((5-(4-fluorophenyl)-7-methyl-4-oxo-4,5,6,7-tetrahydropyrazolo[1,5-a]pyrazin-2-yl)methyl)amino)phenyl)acetonitrile;

(R)-2-(((2,3-difluorophenyl)amino)methyl)-5-(4-fluorophenyl)-7-methyl-6,7-dihydropyrazolo[1,5-a]pyrazin-4(5H)-one;

(S)-2-(((2,3-difluorophenyl)amino)methyl)-5-(4-fluorophenyl)-7-methyl-6,7-dihydropyrazolo[1,5-a]pyrazin-4(5H)-one;

(R)-2-(((2,5-difluorophenyl)amino)methyl)-5-(4-fluorophenyl)-7-methyl-6,7-dihydropyrazolo[1,5-a]pyrazin-4(5H)-one;

(S)-2-(((2,5-difluorophenyl)amino)methyl)-5-(4-fluorophenyl)-7-methyl-6,7-dihydropyrazolo[1,5-a]pyrazin-4(5H)-one;

(R)-2-(((2,6-difluorophenyl)amino)methyl)-5-(4-fluorophenyl)-7-methyl-6,7-dihydropyrazolo[1,5-a]pyrazin-4(5H)-one;

(S)-2-(((2,6-difluorophenyl)amino)methyl)-5-(4-fluorophenyl)-7-methyl-6,7-dihydropyrazolo[1,5-a]pyrazin-4(5H)-one;

(S)-2-(((3,5-difluorophenyl)amino)methyl)-5-(4-fluorophenyl)-7-methyl-6,7-dihydropyrazolo[1,5-a]pyrazin-4(5H)-one;

(R)-2-(((2,4-difluorophenyl)amino)methyl)-5-(4-fluorophenyl)-7-methyl-6,7-dihydropyrazolo[1,5-a]pyrazin-4(5H)-one;

(S)-2-(((2,4-difluorophenyl)amino)methyl)-5-(4-fluorophenyl)-7-methyl-6,7-dihydropyrazolo[1,5-a]pyrazin-4(5H)-one;

(R)-2-(((3,4-difluorophenyl)amino)methyl)-5-(4-fluorophenyl)-7-methyl-6,7-dihydropyrazolo[1,5-a]pyrazin-4(5H)-one;

(S)-2-(((3,4-difluorophenyl)amino)methyl)-5-(4-fluorophenyl)-7-methyl-6,7-dihydropyrazolo[1,5-a]pyrazin-4(5H)-one;

(R)-5-(4-fluorophenyl)-7-methyl-2-(((2,4,6-trifluorophenyl)amino)methyl)-6,7-dihydropyrazolo[1,5-a]pyrazin-4(5H)-one;

(S)-5-(4-fluorophenyl)-7-methyl-2-(((2,4,6-trifluorophenyl)amino)methyl)-6,7-dihydropyrazolo[1,5-a]pyrazin-4(5H)-one;

5-(4-fluorophenyl)-2-(((5-fluoropyridin-2-yl)amino)methyl)-6,7-dihydropyrazolo[1,5-a]pyrazin-4(5H)-one;

5-(4-fluorophenyl)-2-((pyridin-2-ylamino)methyl)-6,7-dihydropyrazolo[1,5-a]pyrazin-4(5H)-one;

5-(4-fluorophenyl)-2-(((6-methylpyridin-2-yl)amino)methyl)-6,7-dihydropyrazolo[1,5-a]pyrazin-4(5H)-one;

2-(((5-chloropyridin-2-yl)amino)methyl)-5-(4-fluorophenyl)-6,7-dihydropyrazolo[1,5-a]pyrazin-4(5H)-one;

5-(4-fluorophenyl)-2-(((5-methylpyridin-2-yl)amino)methyl)-6,7-dihydropyrazolo[1,5-a]pyrazin-4(5H)-one;

5-(4-fluorophenyl)-2-(((3-methylpyridin-2-yl)amino)methyl)-6,7-dihydropyrazolo[1,5-a]pyrazin-4(5H)-one;

5-(4-fluorophenyl)-2-(((4-methylpyridin-2-yl)amino)methyl)-6,7-dihydropyrazolo[1,5-a]pyrazin-4(5H)-one;

5-(4-fluorophenyl)-2-(((3-(trifluoromethyl)pyridin-2-yl)amino)methyl)-6,7-dihydropyrazolo[1,5-a]pyrazin-4(5H)-one;

2-(((6-chloropyridin-2-yl)amino)methyl)-5-(4-fluorophenyl)-6,7-dihydropyrazolo[1,5-a]pyrazin-4(5H)-one;

2-(((3,5-difluorophenyl)(methyl)amino)methyl)-5-(4-fluorophenyl)-6,7-dihydropyrazolo[1,5-a]pyrazin-4(5H)-one;

2-(((4-chloropyridin-2-yl)amino)methyl)-5-(4-fluorophenyl)-6,7-dihydropyrazolo[1,5-a]pyrazin-4(5H)-one;

2-(((3-chloropyridin-2-yl)amino)methyl)-5-(4-fluorophenyl)-6,7-dihydropyrazolo[1,5-a]pyrazin-4(5H)-one;

5-(4-fluorophenyl)-2-(((3-fluoropyridin-2-yl)amino)methyl)-6,7-dihydropyrazolo[1,5-a]pyrazin-4(5H)-one;

5-(4-fluorophenyl)-2-(((6-(trifluoromethyl)pyridin-2-yl)amino)methyl)-6,7-dihydropyrazolo[1,5-a]pyrazin-4(5H)-one;

5-(4-chlorophenyl)-2-(((4-methoxyphenyl)(methyl)amino)methyl)-6,7-dihydropyrazolo[1,5-a]pyrazin-4(5H)-one;

5-(3,4-difluorophenyl)-2-(((4-methoxyphenyl)(methyl)amino)methyl)-6,7-dihydropyrazolo[1,5-a]pyrazin-4(5H)-one;

5-(3-chlorophenyl)-2-(((4-methoxyphenyl)(methyl)amino)methyl)-6,7-dihydropyrazolo[1,5-a]pyrazin-4(5H)-one;

2-(((4-methoxyphenyl)(methyl)amino)methyl)-5-(p-tolyl)-6,7-dihydropyrazolo[1,5-a]pyrazin-4(5H)-one;

5-(2-chlorophenyl)-2-(((4-methoxyphenyl)(methyl)amino)methyl)-6,7-dihydropyrazolo[1,5-a]pyrazin-4(5H)-one;

5-(3-fluorophenyl)-2-(((4-methoxyphenyl)(methyl)amino)methyl)-6,7-dihydropyrazolo[1,5-a]pyrazin-4(5H)-one;
2-(((4-methoxyphenyl)(methyl)amino)methyl)-5-(2,4,6-trifluorophenyl)-6,7-dihydropyrazolo[1,5-a]pyrazin-4(5H)-one;
2-(((4-methoxyphenyl)(methyl)amino)methyl)-5-(m-tolyl)-6,7-dihydropyrazolo[1,5-a]pyrazin-4(5H)-one;
5-(3,5-difluorophenyl)-2-(((4-methoxyphenyl)(methyl)amino)methyl)-6,7-dihydropyrazolo[1,5-a]pyrazin-4(5H)-one;
5-(2-fluorophenyl)-2-(((4-methoxyphenyl)(methyl)amino)methyl)-6,7-dihydropyrazolo[1,5-a]pyrazin-4(5H)-one;
5-(2,5-difluorophenyl)-2-(((4-methoxyphenyl)(methyl)amino)methyl)-6,7-dihydropyrazolo[1,5-a]pyrazin-4(5H)-one;
5-(2,3-difluorophenyl)-2-(((4-methoxyphenyl)(methyl)amino)methyl)-6,7-dihydropyrazolo[1,5-a]pyrazin-4(5H)-one;
5-(2-fluoro-4-methylphenyl)-2-(((4-methoxyphenyl)(methyl)amino)methyl)-6,7-dihydropyrazolo[1,5-a]pyrazin-4(5H)-one;
5-(4-fluoro-2-methylphenyl)-2-(((4-methoxyphenyl)(methyl)amino)methyl)-6,7-dihydropyrazolo[1,5-a]pyrazin-4(5H)-one;
5-(2,6-difluorophenyl)-2-(((4-methoxyphenyl)(methyl)amino)methyl)-6,7-dihydropyrazolo[1,5-a]pyrazin-4(5H)-one;
2-(((4-methoxyphenyl)(methyl)amino)methyl)-5-(o-tolyl)-6,7-dihydropyrazolo[1,5-a]pyrazin-4(5H)-one;
2-(2-(((4-methoxyphenyl)(methyl)amino)methyl)-4-oxo-6,7-dihydropyrazolo[1,5-a]pyrazin-5(4H)-yl)benzonitrile;
5-(3-methoxyphenyl)-2-(((4-methoxyphenyl)(methyl)amino)methyl)-6,7-dihydropyrazolo[1,5-a]pyrazin-4(5H)-one;
5-(4-methoxyphenyl)-2-(((4-methoxyphenyl)(methyl)amino)methyl)-6,7-dihydropyrazolo[1,5-a]pyrazin-4(5H)-one;
2-(((4-methoxyphenyl)(methyl)amino)methyl)-5-(2-methylthiazol-4-yl)-6,7-dihydropyrazolo[1,5-a]pyrazin-4(5H)-one;
3-(2-(((4-methoxyphenyl)(methyl)amino)methyl)-4-oxo-6,7-dihydropyrazolo[1,5-a]pyrazin-5(4H)-yl)benzonitrile;
2-(((4-methoxyphenyl)(methyl)amino)methyl)-5-(pyridin-2-yl)-6,7-dihydropyrazolo[1,5-a]pyrazin-4(5H)-one;
4-(2-(((4-methoxyphenyl)(methyl)amino)methyl)-4-oxo-6,7-dihydropyrazolo[1,5-a]pyrazin-5(4H)-yl)benzonitrile;
5-(2-methoxyphenyl)-2-(((4-methoxyphenyl)(methyl)amino)methyl)-6,7-dihydropyrazolo[1,5-a]pyrazin-4(5H)-one;
5-(4-(methoxymethyl)phenyl)-2-(((4-methoxyphenyl)(methyl)amino)methyl)-6,7-dihydropyrazolo[1,5-a]pyrazin-4(5H)-one;
2-(((4-methoxyphenyl)(methyl)amino)methyl)-5-(pyridin-3-yl)-6,7-dihydropyrazolo[1,5-a]pyrazin-4(5H)-one;
5-(5-fluoropyridin-2-yl)-2-(((4-methoxyphenyl)(methyl)amino)methyl)-6,7-dihydropyrazolo[1,5-a]pyrazin-4(5H)-one;
5-(4-(difluoromethoxy)phenyl)-2-(((4-methoxyphenyl)(methyl)amino)methyl)-6,7-dihydropyrazolo[1,5-a]pyrazin-4(5H)-one;
5-(5-chloropyridin-2-yl)-2-(((4-methoxyphenyl)(methyl)amino)methyl)-6,7-dihydropyrazolo[1,5-a]pyrazin-4(5H)-one;
5-(4-fluorophenyl)-2-(1-(phenylamino)ethyl)-6,7-dihydropyrazolo[1,5-a]pyrazin-4(5H)-one;
5-(4-fluorophenyl)-2-(1-((4-fluorophenyl)amino)ethyl)-6,7-dihydropyrazolo[1,5-a]pyrazin-4(5H)-one;
2-(1-((4-chlorophenyl)amino)ethyl)-5-(4-fluorophenyl)-6,7-dihydropyrazolo[1,5-a]pyrazin-4(5H)-one;
5-(4-fluorophenyl)-2-(1-((4-methoxyphenyl)amino)ethyl)-6,7-dihydropyrazolo[1,5-a]pyrazin-4(5H)-one;
5-(3,4-difluorophenyl)-2-((ethyl(4-methoxyphenyl)amino)methyl)-6,7-dihydropyrazolo[1,5-a]pyrazin-4(5H)-one;
5-(3,4-difluorophenyl)-2-(((4-methoxyphenyl)(propyl)amino)methyl)-6,7-dihydropyrazolo[1,5-a]pyrazin-4(5H)-one;
5-(3,4-difluorophenyl)-2-(((4-methoxyphenyl)amino)methyl)-6,7-dihydropyrazolo[1,5-a]pyrazin-4(5H)-one;
5-(4-chlorophenyl)-2-(((4-methoxyphenyl)amino)methyl)-6,7-dihydropyrazolo[1,5-a]pyrazin-4(5H)-one;
5-(4-chloro-2-fluorophenyl)-2-(((4-methoxyphenyl)(methyl)amino)methyl)-6,7-dihydropyrazolo[1,5-a]pyrazin-4(5H)-one;
5-(2-chloro-3-fluorophenyl)-2-(((4-methoxyphenyl)(methyl)amino)methyl)-6,7-dihydropyrazolo[1,5-a]pyrazin-4(5H)-one;
5-(5-chloro-2-fluorophenyl)-2-(((4-methoxyphenyl)(methyl)amino)methyl)-6,7-dihydropyrazolo[1,5-a]pyrazin-4(5H)-one;
5-(4-chloro-2,6-difluorophenyl)-2-(((4-methoxyphenyl)(methyl)amino)methyl)-6,7-dihydropyrazolo[1,5-a]pyrazin-4(5H)-one;
5-(2-chloro-5-fluorophenyl)-2-(((4-methoxyphenyl)(methyl)amino)methyl)-6,7-dihydropyrazolo[1,5-a]pyrazin-4(5H)-one;
5-(2-chloro-4-fluorophenyl)-2-(((4-methoxyphenyl)(methyl)amino)methyl)-6,7-dihydropyrazolo[1,5-a]pyrazin-4(5H)-one;
5-(3-chloro-5-fluorophenyl)-2-(((4-methoxyphenyl)(methyl)amino)methyl)-6,7-dihydropyrazolo[1,5-a]pyrazin-4(5H)-one;
5-(3-fluoro-5-methoxyphenyl)-2-(((4-methoxyphenyl)(methyl)amino)methyl)-6,7-dihydropyrazolo[1,5-a]pyrazin-4(5H)-one;
5-(3-chloro-4-fluorophenyl)-2-(((4-methoxyphenyl)(methyl)amino)methyl)-6,7-dihydropyrazolo[1,5-a]pyrazin-4(5H)-one;
5-(3-chloro-5-methoxyphenyl)-2-(((4-methoxyphenyl)(methyl)amino)methyl)-6,7-dihydropyrazolo[1,5-a]pyrazin-4(5H)-one;
5-(3-chloro-2-fluorophenyl)-2-(((4-methoxyphenyl)(methyl)amino)methyl)-6,7-dihydropyrazolo[1,5-a]pyrazin-4(5H)-one;
5-(4-chloro-3-fluorophenyl)-2-(((4-methoxyphenyl)(methyl)amino)methyl)-6,7-dihydropyrazolo[1,5-a]pyrazin-4(5H)-one;
2-(((4-(difluoromethoxy)-2-fluorophenyl)amino)methyl)-5-(5-methylthiazol-2-yl)-6,7-dihydropyrazolo[1,5-a]pyrazin-4(5H)-one;
2-(((4-(difluoromethoxy)-2-fluorophenyl)amino)methyl)-5-(6-fluoropyridin-2-yl)-6,7-dihydropyrazolo[1,5-a]pyrazin-4(5H)-one;

5-(4-chloropyridin-2-yl)-2-(((4-(difluoromethoxy)-2-fluorophenyl)amino)methyl)-6,7-dihydropyrazolo[1,5-a]pyrazin-4(5H)-one;

2-(((4-(difluoromethoxy)-2-fluorophenyl)amino)methyl)-5-(2-methylthiazol-4-yl)-6,7-dihydropyrazolo[1,5-a]pyrazin-4(5H)-one;

2-(((4-(difluoromethoxy)-2-fluorophenyl)amino)methyl)-5-(2,4-difluorophenyl)-6,7-dihydropyrazolo[1,5-a]pyrazin-4(5H)-one;

2-(((4-(difluoromethoxy)-2-fluorophenyl)amino)methyl)-5-(3-methoxyphenyl)-6,7-dihydropyrazolo[1,5-a]pyrazin-4(5H)-one;

2-(((4-(difluoromethoxy)-2-fluorophenyl)amino)methyl)-5-(3-fluoropyridin-2-yl)-6,7-dihydropyrazolo[1,5-a]pyrazin-4(5H)-one;

2-(((4-(difluoromethoxy)-2-fluorophenyl)amino)methyl)-5-(5-methylpyridin-2-yl)-6,7-dihydropyrazolo[1,5-a]pyrazin-4(5H)-one;

2-(((4-(difluoromethoxy)-2-fluorophenyl)amino)methyl)-5-(3-fluorophenyl)-6,7-dihydropyrazolo[1,5-a]pyrazin-4(5H)-one;

2-(((4-(difluoromethoxy)-2-fluorophenyl)amino)methyl)-5-(3,4-difluorophenyl)-6,7-dihydropyrazolo[1,5-a]pyrazin-4(5H)-one;

2-(((4-(difluoromethoxy)-2-fluorophenyl)amino)methyl)-5-(5-fluoropyridin-2-yl)-6,7-dihydropyrazolo[1,5-a]pyrazin-4(5H)-one;

2-(((4-(difluoromethoxy)-2-fluorophenyl)amino)methyl)-5-(3-fluoro-5-methoxyphenyl)-6,7-dihydropyrazolo[1,5-a]pyrazin-4(5H)-one;

5-(5-chloropyridin-2-yl)-2-(((4-(difluoromethoxy)-2-fluorophenyl)amino)methyl)-6,7-dihydropyrazolo[1,5-a]pyrazin-4(5H)-one;

5-(4-chloro-2-fluorophenyl)-2-(((4-(difluoromethoxy)-2-fluorophenyl)amino)methyl)-6,7-dihydropyrazolo[1,5-a]pyrazin-4(5H)-one;

5-(3-chlorophenyl)-2-(((4-(difluoromethoxy)-2-fluorophenyl)amino)methyl)-6,7-dihydropyrazolo[1,5-a]pyrazin-4(5H)-one;

2-(((4-(difluoromethoxy)-2-fluorophenyl)amino)methyl)-5-(pyridin-2-yl)-6,7-dihydropyrazolo[1,5-a]pyrazin-4(5H)-one;

2-(((4-(difluoromethoxy)-2-fluorophenyl)amino)methyl)-5-(3,5-difluorophenyl)-6,7-dihydropyrazolo[1,5-a]pyrazin-4(5H)-one; and 2-(((4-(difluoromethoxy)-2-fluorophenyl)amino)methyl)-5-(2-fluorophenyl)-6,7-dihydropyrazolo[1,5-a]pyrazin-4(5H)-one.

\* \* \* \* \*

UNITED STATES PATENT AND TRADEMARK OFFICE
CERTIFICATE OF CORRECTION

PATENT NO. : 9,676,782 B2
APPLICATION NO. : 14/738222
DATED : June 13, 2017
INVENTOR(S) : P. Jeffrey Conn et al.

It is certified that error appears in the above-identified patent and that said Letters Patent is hereby corrected as shown below:

In the Specification

Column 1, Line 18:
Replace the following paragraph:
[[This invention was made with government support under Grant number 1 R01 MH99269-01 awarded by the National Institute of Mental Health (NIMH). The government has certain rights in the invention.]]

With the paragraph:
--This invention was made with government support under Grant Nos. MH084659, and MH099269, awarded by the National Institutes of Health. The government has certain rights in the invention.--

Signed and Sealed this
Eleventh Day of July, 2023

Katherine Kelly Vidal
*Director of the United States Patent and Trademark Office*